US012653993B2

(12) United States Patent
Ben Menachem et al.

(10) Patent No.: US 12,653,993 B2
(45) Date of Patent: Jun. 16, 2026

(54) DEVICES AND METHODS FOR REGIO-SPECIFIC DRUG RELEASE AT ILEOCECAL REGION

(71) Applicant: GIT Therapeutics Ltd., Rosh Haain (IL)

(72) Inventors: Avshalom Ben Menachem, Tel Aviv (IL); Ilan Zalit, Tel Aviv (IL)

(73) Assignee: GIT THERAPEUTICS LTD., Rosh Haain (IL)

( * ) Notice: Subject to any disclaimer, the term of this patent is extended or adjusted under 35 U.S.C. 154(b) by 953 days.

(21) Appl. No.: 17/638,664

(22) PCT Filed: Aug. 30, 2020

(86) PCT No.: PCT/IL2020/050941
§ 371 (c)(1),
(2) Date: Feb. 25, 2022

(87) PCT Pub. No.: WO2021/038572
PCT Pub. Date: Mar. 4, 2021

(65) Prior Publication Data
US 2022/0331570 A1     Oct. 20, 2022

(30) Foreign Application Priority Data

Aug. 29, 2019    (EP) ..................................... 19194378

(51) Int. Cl.
*A61M 31/00*          (2006.01)

(52) U.S. Cl.
CPC ... *A61M 31/002* (2013.01); *A61M 2210/1042* (2013.01)

(58) Field of Classification Search
CPC ................... A61M 31/002; A61M 2210/1042
See application file for complete search history.

(56) References Cited

FOREIGN PATENT DOCUMENTS

WO      2018111329 A1    6/2018
WO      2018119477 A1    6/2018

*Primary Examiner* — Bradley J Osinski
(74) *Attorney, Agent, or Firm* — Momentum IP; Marc Van Dyke

(57)          ABSTRACT

A device for temporary residence at an ileocecal valve of a subject in a trapping configuration is described. The device includes a trapping assembly for blocking a cooperating ingestible object while allowing chyme flow when the device is positioned at the ileocecal valve. The device can transition from the trapping configuration into an emptying configuration in which the device is passes through the ileocecal valve. Oral dosage forms cooperating with the device for local dispensing of a therapeutic agent at the ileocecal valve region are also described.

20 Claims, 18 Drawing Sheets

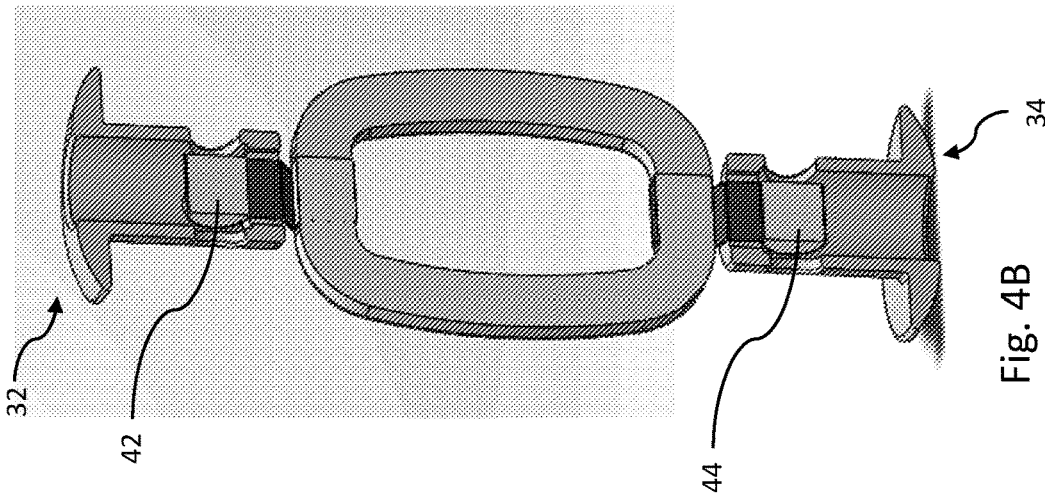
Fig. 4B
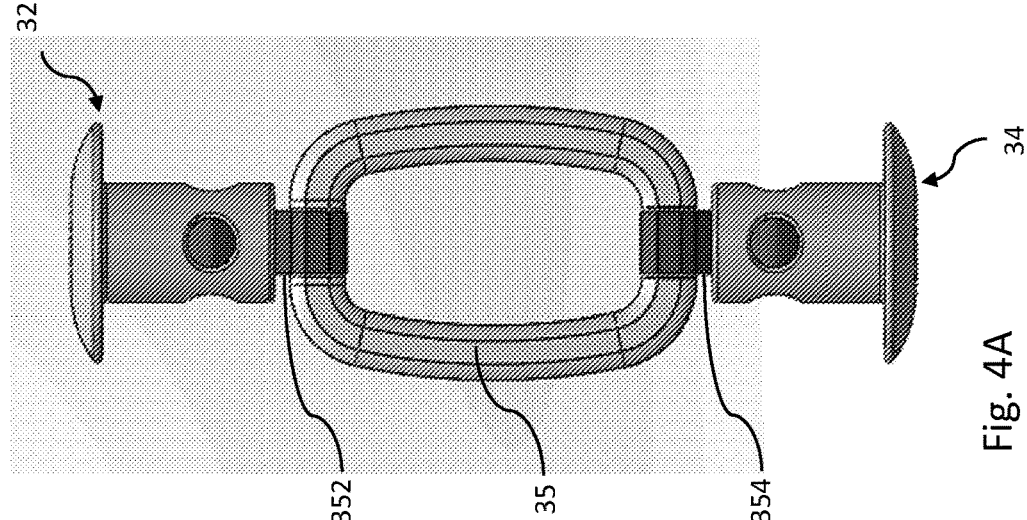
Fig. 4A
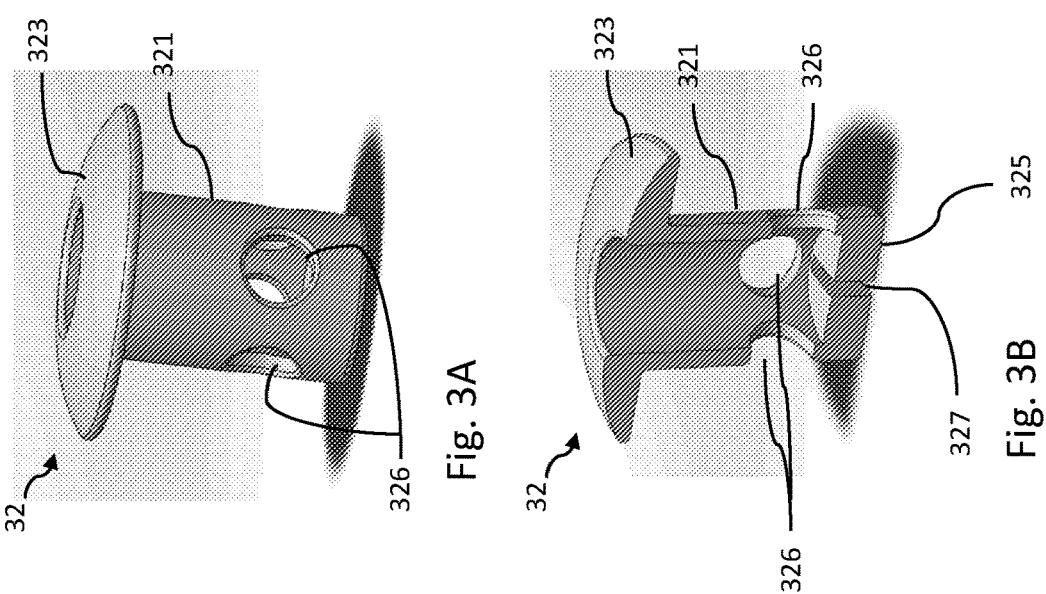
Fig. 3A
Fig. 3B

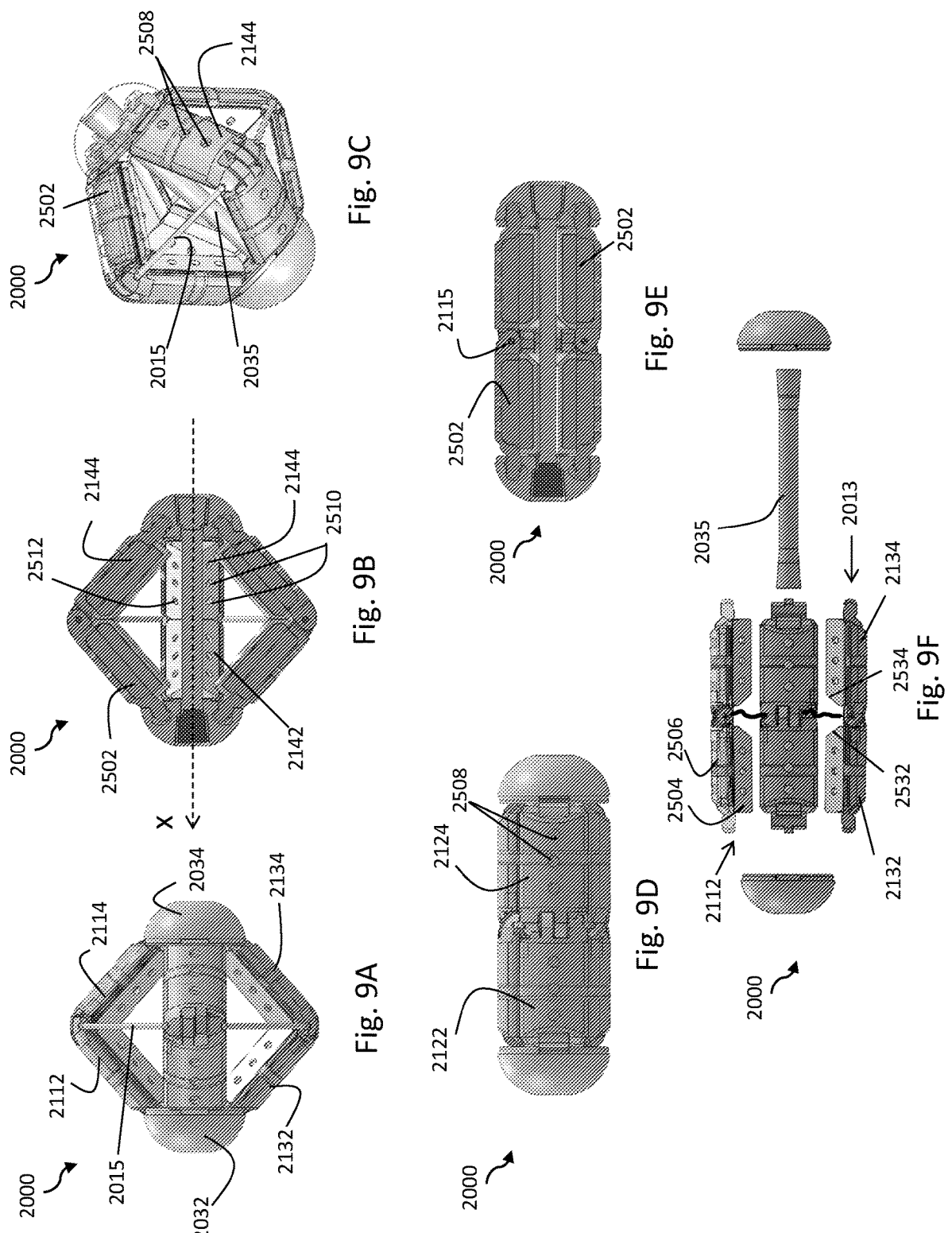

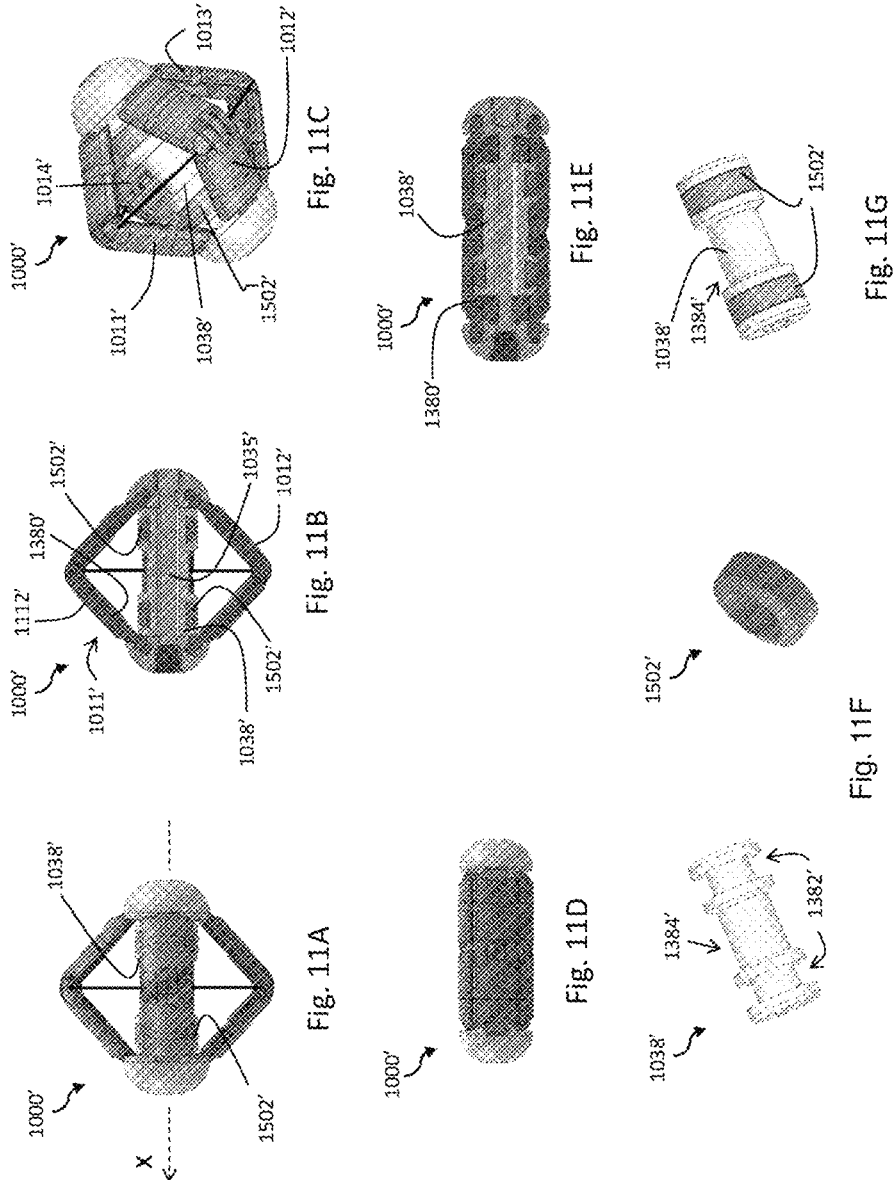

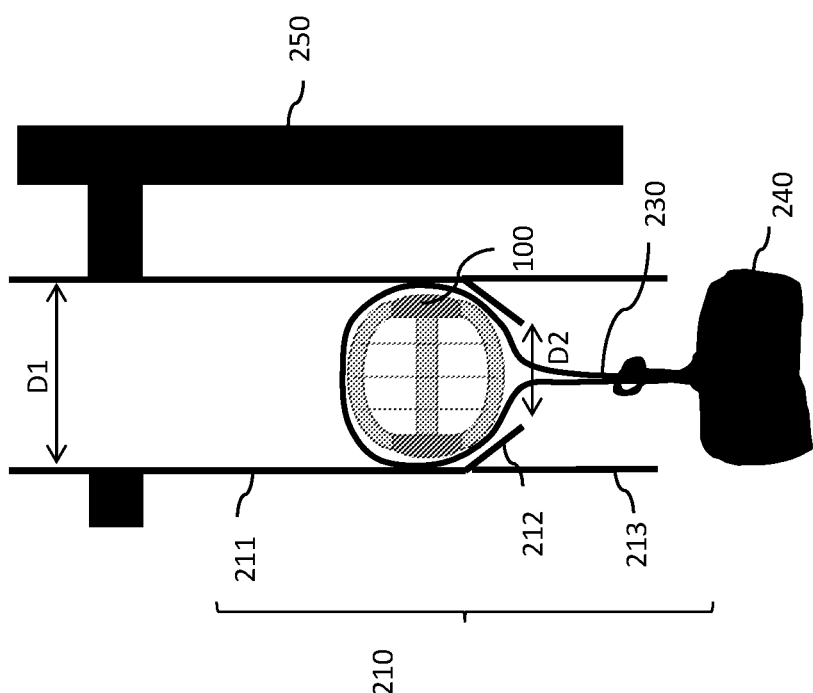
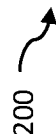
Fig. 12

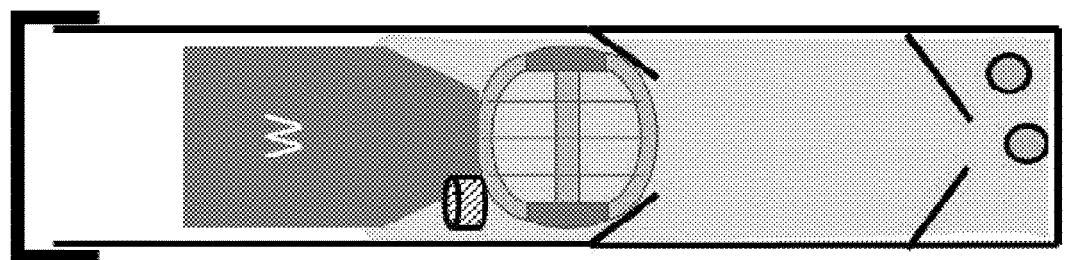
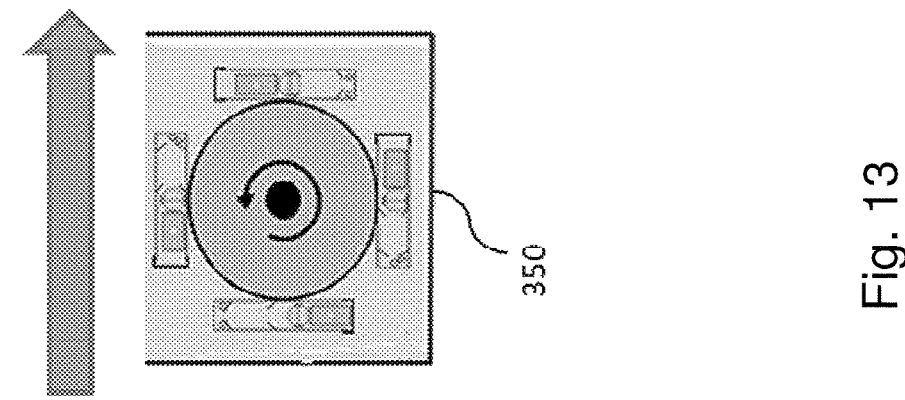
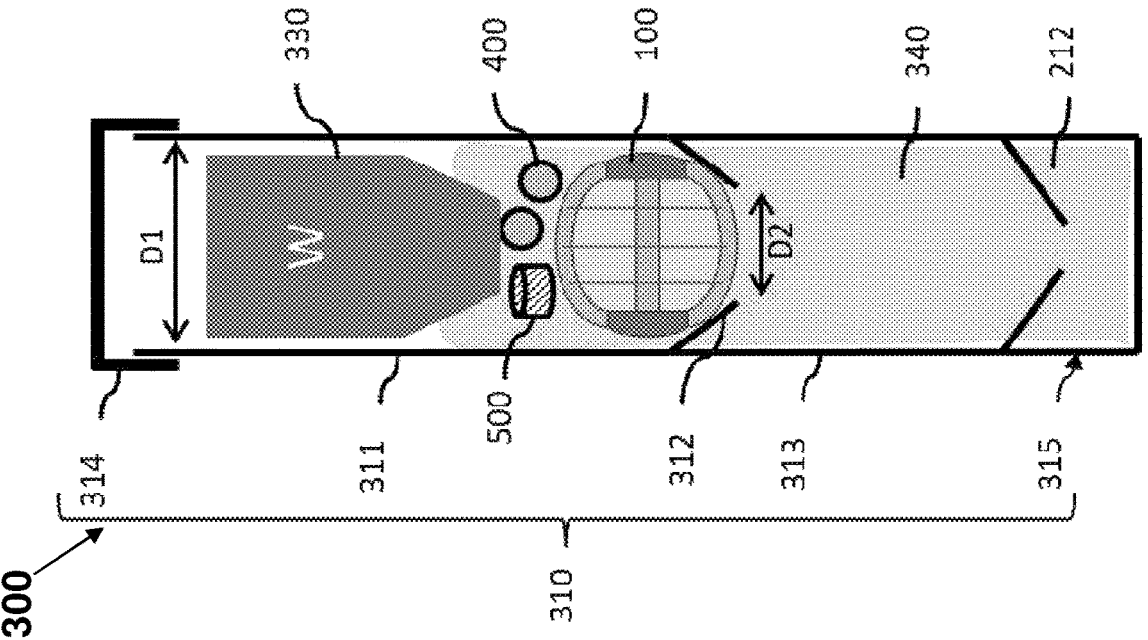
Fig. 13

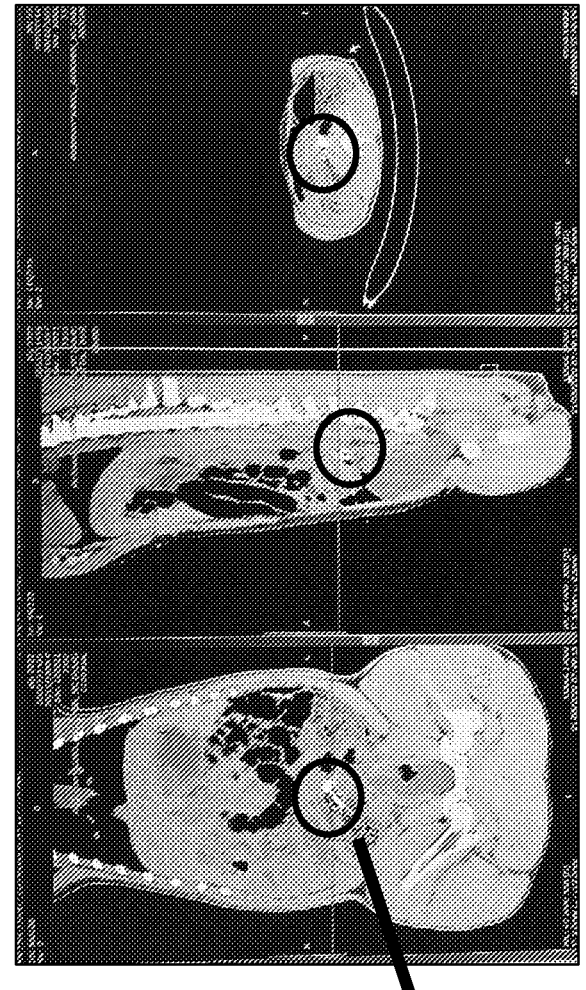
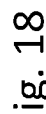
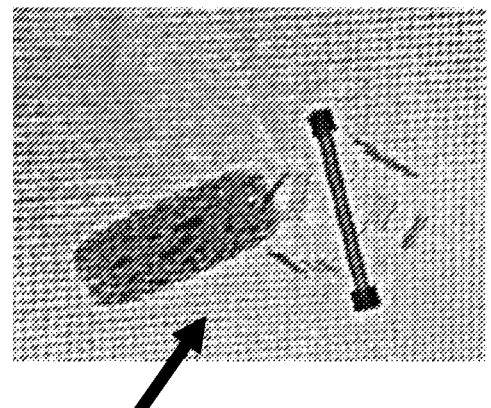
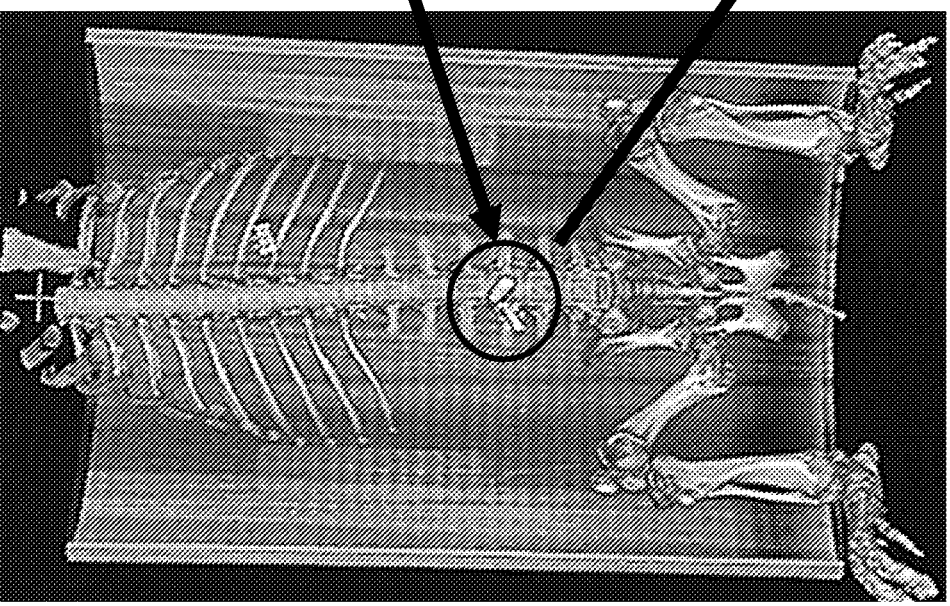
Fig. 18

DEVICES AND METHODS FOR REGIO-SPECIFIC DRUG RELEASE AT ILEOCECAL REGION

CROSS-REFERENCE TO RELATED APPLICATIONS

This application is a National Stage of International Patent App. No. PCT/IL2020/050941, filed Aug. 30, 2020, which claims priority to European Patent App. No. 19194378.6, filed Aug. 29, 2019, the disclosures of which are incorporated by reference in their entireties.

TECHNOLOGICAL FIELD

The present disclosure relates generally to the field of regio-specific release of a substance at a site of a gastrointestinal (GI) tract. More specifically, the present disclosure relates to devices and methods for dispensing locally therapeutic substances at an ileocecal valve (ICV) region of a human body.

BACKGROUND

The gastrointestinal (GI) tract generally provides a therapeutic medium for an individual's body. At times, therapeutic drugs may need to be dispensed to specified locations within the small intestine or large intestine to cure or alleviate the symptoms of some medical conditions. For example, therapeutic drugs dispensed directly within the small intestine or large intestine would not be digested or otherwise compromised in the stomach, and thus allow a higher dose to reach a specific location within the intestine. However, dispensing therapeutic drugs locally i.e., for example directly within the small intestine or large intestine inside a human body (e.g., the cecum, the ascending colon) can be difficult and requires a device or mechanism (e.g., special formulation) to reach and release the therapeutic drug at the desired location. Such a device or mechanism also would need to be operated in a safe manner, in that the device or mechanism needs to physically enter the human body.

Dispensing therapeutic drugs directly within the small intestine or large intestine inside a human body may be useful for enabling treatment of a disease by releasing a medication at the disease site (also referred to as topical treatment) and/or for improving action of medications which have an improved absorption at a specific site (also referred to as site specific or local absorption).

As for topical treatment, an effective way to provide topical dispensing (i.e., local release) to the GI tract (and/or to a particular portion or section of the GI tract, for example a lower part of the small intestine, the ileocecal junction and the ascending colon) of a therapeutic drug to treat the diseased tissue in the GI tract would be desirable.

In practice, however, there are several challenges to such an approach. Methods typically employed to deliver drugs locally all have their own drawbacks.

For example, the usefulness of formulations relying on pH-mediated release (including but not limited to enteric coated formulations, for example Asacol® delayed released tablet) may be limited by the high inter- and intra-patient variability of pH and microflora. The utility may be further limited in patient populations having highly variable GI motility (e.g., patients with ulcerative colitis (UC)), contributing to unpredictable transit times (times for transitioning from one portion of the GI tract to an adjacent portion). (e.g., see Brunner M. et al., "*Gastrointestinal transit, release and plasma pharmacokinetics of a new oral budesonide formulation*," Br. J. Clin. Pharmacol. (2006) 61(1), pp. 31-38). Moreover, pH is dysregulated in ulcerative colitis patients, making pH-dependent drug delivery technologies less predictable.

As for site specific absorption, an effective way to provide improved systemic therapeutic exposure may be in many cases achieved by a system being capable to release drug in a continuous manner (e.g., OROS® technology). However, GI transit and change in conditions along different GI segments (viscosity, permeability, metabolic enzyme, pH etc.) may limit the platform's capability to provide the optimal systemic exposure.

More specifically, Osmotic-controlled Release Oral delivery Systems (OROS® are aimed at releasing at a constant rate a drug for an extended period of time in the GI tract. However, as the OROS® platform moves along the GI tract and releases the drug, it transits through different GI segments having different GI conditions (e.g., dissolution and permeability characteristics). Consequently, although the drug may be released in zero order, the resulting absorption and exposure in the system may be less than optimal. For example, for a drug that can be absorbed only in the small intestine, an OROS® system designed for a 12 hr constant rate of release, may have only 4-6 hr of exposure in the small intestine, because the average drug transit through the small intestine (absorption window) is about 4-6 hr. Thus, the platform's capability to provide improved systemic exposure is limited.

Therefore, there remains a significant unmet medical need for local dispensing of therapeutic drugs in particular with the aim of:

a. Topical treatment: improved treatment regimens for gastrointestinal diseases, such as inflammatory bowel disease (IBD) (e.g., see Harris M. S. et al., "Review article: delivery and efficacy of topical 5-aminosalicylic acid (mesalamine) therapy in the treatment of ulcerative colitis", Aliment Pharmacol. Ther. 2011; 33: 996-1009), including a need for regimens which can dispense therapeutics to specific locations within the GI tract (and particularly at the ileocecal region: the lower part of the small intestine, the ileocecal junction and the ascending colon), thereby reducing or avoiding the drawbacks of other forms of administration;

b. Improved systemic therapeutic exposure i.e., achieving systemic plasma concentrations having minimal fluctuations enabling better efficacy and safety.

GENERAL DESCRIPTION

The present disclosure notably provides methods and (trapping) devices for specifically releasing a therapeutic substance at the lower part of the small intestine, the ileocecal junction and the ascending colon which alleviate at least in part the limitations of the prior art techniques.

Colonic release has great benefits for some therapeutic agents when used in various medical conditions:

a. Treatment of Inflammatory Bowel Disease (IBD) such as Ulcerative Colitis (UC). Indeed, the ileocecal junction and ascending colon are inflammation sites (especially in Pancolitis). An effective disease treatment may be achieved when effective local and/or topical exposure of the drug in the inflamed tissue is obtained (i.e., high local concentration and long exposure duration).

b. Treatment of colonic cancer or colonic infections.

c. Improved systemic therapeutic exposure by local absorption and improved bioavailability i.e., achieving systemic plasma concentrations having minimal fluctuations enabling better efficacy and safety.

d. New administration site for drug delivery.

Therefore, the present disclosure provides a device for temporary residence at an ileocecal valve of a subject, the device having a trapping configuration, wherein in the trapping configuration, the device is configured to be retained at the ileocecal valve of the subject when the device is positioned at the ileocecal valve; comprises a trapping assembly configured for blocking a cooperating ingestible object while allowing chyme flow, when the device is positioned at the ileocecal valve; and the device is further configured to transfer from the trapping configuration into an emptying configuration in which the device is configured to pass through the ileocecal valve.

In some examples, the trapping assembly comprises at least three flexible arms. Each arm has a first end and a second end. The biasing assembly comprises a first and second coupling heads, wherein the first end of each flexible arm is coupled to the first coupling head and the second end of each flexible arm is coupled to the second coupling head; a resiliently deformable member configured to force the coupling heads together to bend the arms thereby biasing the device in the trapping configuration.

The present disclosure also provides a device for temporary residence at an ileocecal valve of a subject. The device comprises at least three flexible arms, each arm having a first end and a second end. The device also comprises a first and second coupling heads. The first end of each arm is coupled to the first coupling head and the second end of each arm is coupled to the second coupling head. The device also comprises a resiliently deformable member configured to force the coupling heads together to bend the arms thereby biasing the device in a trapping configuration. In the trapping configuration, the device is configured, when the device is positioned at the ileocecal valve, to be retained at the ileocecal valve of the subject, and to block a cooperating ingestible object while allowing chyme flow. The device is further configured to transfer from the trapping configuration into an emptying configuration. The device is thereby configured to pass through the ileocecal valve in the emptying configuration.

Exemplary features of any of the devices (referred to as "the device" in the following) are now discussed.

In some embodiments, the device has a closed configuration and is deformable from the closed configuration into the expanded configuration. The device may be further configured to be reversibly deformable from the trapping configuration into the closed configuration. In examples of such embodiments, the device in the closed configuration has a compact shape.

In some embodiments, the dimensions of the device in the closed configuration are such that it can be ingested and preferably fitted in a cylinder of length of about 35 mm or less and/or of diameter of about 12 mm or less, preferably in a cylinder of length equal to or less than 32 mm, 31 mm, 30 mm or 29 mm and/or of diameter equal to or less than 11, 10.5 mm or 10.2 mm, preferably a cylinder of length equal to or less that 31 mm and/or of diameter equal to or less than 11 mm, more preferably in a cylinder of length equal to 29 mm and of diameter equal to 10.2 mm.

In some embodiments, the device is configured to transfer from the trapping configuration into the emptying configuration upon the resiliently deformable member stopping to force the coupling heads together.

In some embodiments, the resiliently deformable member is arranged between the at least three arms.

In some embodiments, each arm is arranged longitudinally alongside each other.

In some embodiments, the device (e.g. the trapping assembly) further comprises one or more circumferential belts circling around the at least three flexible arms, and/or one or more circumferential threads circumferentially linking the at least three flexible arms.

In some embodiments, in a closed configuration, the resiliently deformable member is stretched, and the arms are substantially straight. In the expanded configuration, the arms are bent, and the resiliently deformable member may be stretched, but less than in the closed configuration. In other words, an extension of the resiliently deformable member may be larger in the closed configuration than in the expanded configuration and the arms may be substantially straight in the closed configuration. For example, the resiliently deformable member may be further configured to be reversibly stretched, thereby straightening the at least three arms to reversibly deform the device from the trapping configuration into a closed configuration, the at least three arms being substantially straight in the closed configuration.

In some embodiments, the resiliently deformable member is releasably secured to at least one of the first and second coupling heads. For example, the resiliently deformable member is configured to be released from the at least one of the first and second coupling heads when the device in the trapping configuration is exposed to a predetermined activation signal. This may cause the device to transfer from the trapping configuration into the emptying configuration.

In some embodiments, the first end of each flexible arm is coupled to the first coupling head releasably, and the second end of each flexible arm is coupled to the second coupling head releasably.

In some embodiments, in the trapping configuration, said first and second ends are each inserted in a respective cavity of the first and second coupling heads, the resiliently deformable member maintaining said first and second end each secured inside the respective cavity.

In some embodiments, said first and second ends are each rotatable in the respective cavity.

In some embodiments, when the device transfers from the trapping configuration into the emptying configuration, said first and second ends are each dimensioned to move out of the respective cavity (i.e., the dimensioning enables such moving out), the device being thereby configured for the disassembling of the at least three flexible arms from the first and second coupling heads. In particular, the detachment of the arms from the head may be possible when the device is in the emptying configuration, and still the detachment of the arms from the head cavities may be induced by GI motility. For example, the transfer into the emptying configuration may move the arm ends out of abutment with abutment surfaces in the cavities, thereby enabling the ends to move out of the cavities.

In some embodiments, the device further comprises a support tube, the resiliently deformable member being arranged inside the support tube.

In some embodiments, the device further carries a load of an active pharmaceutical ingredient inside or on the support tube, for example in an interstice formed between the support tube and the resiliently deformable member.

In some embodiments, the load of the active pharmaceutical ingredient is carried inside or on the support tube in a solid, semi-solid, powder, gel, and/or liquid form.

In some embodiments, the support tube has apertures formed thereon, the apertures providing exposure to the inside of the support tube.

In some embodiments, the support tube has one or more peripheral grooves each lodging a ring-shaped form containing the active pharmaceutical ingredient.

In some embodiments, wherein at least one arm (e.g., each arm) is articulated and/or composed of a set of arm sections, wherein said arm sections (e.g., of each arm) are preferably rigid.

In some embodiments, at least one (e.g., each) arm section comprises one or more integrally formed components.

In some embodiments, the one or more integrally formed components of said at least one arm section comprise one or more integrally formed components made of a rigid material, one or more integrally formed components made of a semi-rigid material, and/or one or more integrally formed components made of a flexible material.

In some embodiments, each integrally formed component of said at least one arm section is 3D printed or injection molded.

In some embodiments, at least two (e.g., the set of) arm sections of at least one (e.g., each) flexible arm are coupled end to end with a pivot-type coupling.

In some embodiments, the pivot-type coupling comprises transversal hinge holes of the arm sections of the at least two arm sections and a hinge connector passing through the transversal hinge holes.

In some embodiments, each flexible arm consists of two arm sections, each arm section being coupled at one end to the first or second coupling head and at the other end to the other arm section.

In some embodiments, each arm section is substantially of a same length, the device having a generally bipyramidal shape in the trapping configuration, preferably a generally octahedral shape.

In some embodiments, at least one arm section comprises an exposed cavity.

In some embodiments, the at least one arm section comprises two components attached one to another and forming the exposed cavity therebetween.

In some embodiments, the two arm section components are snapped one to another.

In some embodiments, the at least one arm section comprises a peripheral wall, the peripheral wall having apertures formed thereon, the apertures providing exposure of the exposed cavity.

In some embodiments, the exposed cavity contains an active pharmaceutical ingredient.

In some embodiments, the active pharmaceutical ingredient is contained in the exposed cavity in a solid, semi-solid, powder, gel, and/or liquid form.

In some embodiments, at least one (e.g., each) flexible arm is made of an elastic material, the resiliently deformable member being configured to bend the arms in a rounded shape.

In some embodiments, at least one (e.g., each) flexible arm comprises an integrally formed component made of the elastic material, the resiliently deformable member being configured to bend the integrally formed component in a rounded shape. In examples, the elastic material is silicone.

In some embodiments, the resiliently deformable member is elastic (i.e., the resiliently deformable member is an elastic member). In examples, the resiliently deformable member is made of silicone.

In some embodiments, the resiliently deformable member is a spring. In examples, the spring is made of metal, preferably stainless steel or Nitinol.

In some embodiments, the arms are at least partially made of a material that gradually erodes in the intestine, so as to facilitate emptying.

In some embodiments, the arms are coated with a material resistant at standard stomach environmental conditions and/or enabling the device to reach the ICV region substantially intact.

In some embodiments, the device further comprises an opening assembly configured to transfer the device from the closed configuration into the trapping configuration.

In some embodiments, the opening assembly comprises a biasing assembly configured to bias the device in the trapping configuration so that it tends to resiliently return from the closed configuration into the trapping configuration.

In some embodiments, the device further comprises a locking element arranged to temporary maintain the device in the closed configuration for facilitating administration.

In some embodiments, the locking element is configured to release the device in the trapping configuration in the small intestine when the device is positioned in the small intestine. For example, the device may be ingestible, and the locking element may be configured to release the device into the trapping configuration when reaching the small intestine environmental conditions (i.e., after exiting the stomach). In other examples, the device may be configured to be administered by upper endoscopy and to be released directly in the small intestine.

In some embodiments, the locking element is at least partially made of a material degrading at standard small intestine environmental conditions and resistant at standard stomach environmental conditions.

In some embodiments, the locking element is at least partially coated with or made of an enteric polymer.

In some embodiments, the locking element is an (e.g., ingestible) container and the device is contained in the container in the closed configuration.

In some embodiments, the device comprises, additionally to the locking element, a container and the device is contained in the container in the closed configuration.

In some embodiments, the device in the trapping configuration is configured to be capable of transiting through the small intestine to the ileocecal valve by standard gastrointestinal motility without damaging the small intestine.

In some embodiments, the dimensions of the device in the trapping configuration are such that it can be fitted in a sphere of a diameter of about 35 mm or less, and preferably of about 30 mm or 25 mm or less, so as to allow transiting through the small intestine of the subject.

In some embodiments, the device further comprises an external padding structure.

In some embodiments, a volume occupied by the device in the trapping configuration is larger than a sphere of a diameter of about 17 mm, and optionally larger than a sphere of a diameter of about 20 mm. In such embodiments, an external hull of the device in the expanded configuration may stick out of a sphere of a diameter of about 17 mm and optionally a sphere of a diameter of about 20 mm.

In some embodiments, the trapping assembly comprises a meshed structure having one or more openings configured for preventing the cooperating object from passing therethrough.

In some embodiments, the ingestible cooperating object is an oral dosage form having predetermined minimal external dimensions (when the oral dosage form reaches the ICV).

In some embodiments, the trapping assembly is configured for blocking rigid spherical objects having a diameter above a trapping threshold diameter.

In some embodiments, the trapping threshold diameter is in the range of about 7 to 12 mm, preferably about 9 mm.

In some embodiments, the first and second coupling heads each function as a hook and may be referred to as first and second "coupling hooks".

In some embodiments, the device further comprises a container to temporarily at least partially enclose the device in the closed configuration, wherein the container is resistant to standard gastric environmental conditions and configured to degrade in small intestine environmental conditions. For example, the container may be a capsule. Alternatively or additionally, the container may be at least partially coated with or made of an enteric polymer.

In some embodiments, the device further comprises a labelling element enabling detection of the device in a subject by external imaging means, wherein the imaging means is optionally X-ray imaging.

In some embodiments, an external envelope of the device in the trapping configuration is configured to contact the subject tissue and the external envelope of the device is configured to avoid damaging the subject tissue. For example, the external envelope of the device is flexible and/or blunt to avoid damaging the subject tissue.

In some embodiments, the device carries a load of an active pharmaceutical ingredient, and the device is further configured for releasing at least partially the active pharmaceutical ingredient (while allowing chyme flow), when the device is positioned at the ileocecal valve and in the trapping configuration.

In some embodiments, the device comprises an inner space in the closed configuration formed between components of the device (e.g., around the resiliently deformable member between the at least three arms and the coupling heads), the inner space containing at least part of the load of the active pharmaceutical ingredient.

In some embodiments, the device comprises at least one portion or component which comprises an exposed cavity, the exposed cavity containing at least part of the load of the active pharmaceutical ingredient.

In some embodiments, the at least one portion or component comprises a peripheral wall, the peripheral wall having apertures formed thereon, the apertures providing exposure of the exposed cavity.

In some embodiments, the device comprises an exposed recess, the exposed recess lodging at least part of the load of the active pharmaceutical ingredient.

In some embodiments, the device comprises a coating on an exposed surface, the coating containing at least part of the load of the active pharmaceutical ingredient.

In some embodiments, the load of the active pharmaceutical ingredient is carried in a solid, semi-solid, powder, gel, and/or liquid form.

In some embodiments, the load of the active pharmaceutical ingredient is contained in an embedded dosage form which occupies at least 5% of the volume of a convex hull of the device in the closed configuration, preferably at least 10%, at least 15%, or at least 25% of the volume of a convex hull of the device in the closed configuration.

In some embodiments, each coupling head comprises one or more rigid and/or integrally formed components, each coupling head preferably being rigid and integrally formed.

In some embodiments, the device has in the trapping configuration a convex hull presenting a (e.g., Hakon Wadell) sphericity above 0.8, and/or a ratio between a maximal (e.g., planar) circumference and a minimal (e.g., planar) circumference below 1.5.

In some embodiments, the resiliently deformable member is secured to both the first and second coupling heads, and the resiliently deformable member is configured, for each respective activation signal from a predetermined set of one or more activation signals, to be released from at least one respective coupling head from the first and second coupling heads, when the device in the trapping configuration is exposed to the respective activation signal, thereby causing the device to transfer from the trapping configuration into the emptying configuration.

In some embodiments, the device further comprises a trigger assembly configured to cause the device to transfer from the trapping configuration into the emptying configuration upon activation.

In some embodiments, the trigger assembly is configured to activate when the device in the trapping configuration is exposed to an activation signal.

In some embodiments, the activation signal comprises exposure to standard ileocecal region environmental conditions for a predetermined residence time period. In examples, the predetermined residence time period is one day, two days, three days or more and/or twelve weeks or less, for example one month, one week, two weeks, three weeks, one day, two days or three days (i.e., the expanded device is designed to be retained in the ICV for said residence time period before being transferred into the emptying configuration).

In some embodiments, the activation signal comprises exposure of the device in the trapping configuration to at least one activation environmental condition.

In some embodiments, the activation environmental condition comprises a surrounding environment reaching a predetermined pH threshold, for example reaching below pH 5.

In some embodiments, the activation signal comprises an electromagnetic or magnetic or ultrasound signal.

In some embodiments, the trigger assembly comprises one or more support elements configured to temporarily maintain the device in the trapping configuration.

In some embodiments, the one or more support elements are configured to be disabled upon activation of the trigger assembly thereby causing the device to transfer into the emptying configuration.

In some embodiments, the one or more support elements are configured to be disabled when the device in the trapping configuration is exposed to the activation signal.

In some embodiments, the one or more support elements are configured to be disabled by degradation when the device in the trapping configuration is exposed to the activation signal.

In some embodiments, the one or more support elements are configured to be disabled when a surrounding pH reaches a predetermined pH threshold.

In some embodiments, the one or more support elements are at least partially made of a pH dependent polymer configured to dissolve when the surrounding pH reaches the predetermined pH threshold, preferably when the surrounding pH reaches below pH 5.

In some embodiments, the one or more support elements are configured to be disabled when a predetermined time period elapsed subsequent to positioning of the device at the ileocecal valve.

In some embodiments, the one or more support elements are at least partially made of a material configured to degrade at standard ileocecal valve environmental conditions.

In some embodiments, the one or more support elements comprise a material configured to degrade when the surrounding pH is between 6.8 and 7.5.

In some embodiments, the device may comprise one or more first support elements at least partially made of a pH dependent polymer configured to dissolve when the surrounding pH reaches the predetermined pH threshold, preferably when the surrounding pH reaches below pH 5, and additionally one or more second support elements which comprise a material configured to degrade when the surrounding pH is between 6.8 and 7.5. In some embodiments, the one or more first support elements are configured to degrade faster than the one or more second support elements.

In some embodiments, at least one (e.g., each) of the one or more support elements is an integrally formed component presenting a diameter (i.e., length of longest straight segment from a point of object to another point of object) shorter than a half (preferably shorter than a fourth) of a diameter of the device in the expanded configuration. In examples where the device is configured to transfer from the expanded configuration into the emptying configuration by disassembling into at least two disassembled subcomponents, such support element may present a diameter shorter than a half (preferably shorter than a fourth) of a diameter of each disassembled subcomponent (e.g., at the time when the disassembling occurs in case the disassembled subcomponent is not rigid). Such a support element may enable localized degradation until emptying of the device, thus little affecting (at least not substantially) structural rigidity, shape, and/or size of the device while in the expanded configuration. In examples where the device carries/embeds a load of API, the integrally formed component may be separate or distinct from at least part (e.g., all) of said load of API.

In some embodiments, the one or more support elements are configured to form one or more structural weak points of the device to enable a collapse of the device into the emptying configuration after the device is exposed to the activation signal. In some embodiments, the one or more support elements comprise at least one given support element configured to form a structural weak point of the device to enable a collapse of the device into the emptying configuration after the device is exposed to a given activation signal. The one or more structural weak points may enable (preferably sudden) disassembly of the device into at least two disassembled subcomponents. This may contribute to improving a (preferably rapid) transfer from the expanded configuration into the emptying configuration. This also participates in enabling the device to maintain structural integrity until the device transfers into the emptying configuration thereby improving device efficiency until collapse. Furthermore, the components of the device which play a significant role in the main functionalities of the device such as ICV retention and/or API release may generally be configured to not be affected by the activation signal. For example, these components (e.g., arms and/or biasing assembly) may not be made of a material configured to degrade at (i.e., may be made of a material configured to resist to) the environmental conditions of the ICV in embodiments in which the activation signal is exposure to standard ileocecal region environmental conditions for a predetermined residence time period.

In some embodiments, the trigger assembly may be configured such that the device in the expanded configuration maintains structural integrity (i.e., any one or more of shape, size and/or structural rigidity) until transfer in the emptying configuration is effected (i.e., achieved).

In some embodiments, the one or more support elements are configured to be disabled in less than 7 days, 3 days, 1 day or ½ day after said the device is exposed to the activation signal (preferably said activation signal comprising the exposure to ICV environmental conditions).

In some embodiments, the device is configured to transfer from the trapping configuration into the emptying configuration by changing shape.

In some embodiments, the device is configured to transfer from the trapping configuration into the emptying configuration by changing size.

In some embodiments, the device is configured to transfer from the trapping configuration into the emptying configuration by decrease of structural rigidity.

In some embodiments, the device is configured to transfer from the trapping configuration into the emptying configuration by disassembling into at least two disassembled subcomponents.

In some embodiments, the device in the closed configuration can pass through the ileocecal valve of the subject when positioned at the ileocecal valve.

In some embodiments, an external envelope of the device in the emptying configuration and an external envelope of the device in the closed configuration are of same dimensions.

In some embodiments, the closed configuration of the device is the same as the emptying configuration of the device.

In some embodiments, the trigger assembly and the opening assembly form a single transferring assembly configured to transfer the device from the closed configuration into the trapping configuration and to transfer the device from the trapping configuration into the emptying configuration upon activation.

In some embodiments, the one or more support elements are configured to cooperate with the biasing assembly so that, when the one or more support elements are disabled, the biasing of the biasing assembly is prevented and the device thereby transfers into the emptying configuration.

In some embodiments, in the trapping configuration, any one or more of a shape of the device and/or a size of the device and/or a structural rigidity of the device prevent passage of the device through the ileocecal valve, when the device is positioned at the ileocecal valve.

In some embodiments, the device further comprises a trigger assembly configured, when the device in the trapping configuration is exposed to the respective activation signal, to release the resiliently deformable member from the at least one respective coupling head, thereby causing the device to transfer from the trapping configuration into the emptying configuration.

In some embodiments, the predetermined set of one or more activation signals includes a signal which comprises exposure to standard ileocecal region environmental conditions for a predetermined residence time period. In examples, the predetermined residence time period is one day, two days, three days or more and/or twelve weeks or less, for example one month, one week, two weeks, three weeks, one day, two days or three days (i.e., the expanded device is designed to be retained in the ICV for said residence time period before being transferred into the emptying configuration).

In some embodiments, the predetermined set of one or more activation signals includes a signal which comprises exposure of the device in the trapping configuration to at least one activation environmental condition. For example, the signal which comprises exposure of the device in the trapping configuration to at least one activation environmental condition comprises a surrounding environment reaching a predetermined pH threshold, for example reaching below pH 5.

In some embodiments, the predetermined set of one or more activation signals includes a signal which comprises an electromagnetic or magnetic or ultrasound signal.

In some embodiments, the trigger assembly comprises one or more support elements configured to temporarily secure the resiliently deformable member to the at least one respective coupling head, and thereby temporarily maintain the device in the trapping configuration.

In some embodiments, for each respective activation signal from the predetermined set of one or more activation signals, at least one respective support element from the one or more support elements is configured to be disabled upon the device in the trapping configuration being exposed to the respective activation signal, thereby causing release of the resiliently deformable member from the at least one of the first and second coupling heads, thus further causing the device to transfer into the emptying configuration.

In some embodiments, the at least one respective support element is configured to be disabled by degradation when the device in the trapping configuration is exposed to the respective activation signal.

In some embodiments, before degradation, the at least one respective support element securely attaches the at least one respective coupling head to the resiliently deformable member, and upon degradation, the resiliently deformable member retracts and detaches from the at least one respective coupling head.

In some embodiments, the one or more support elements comprise at least one given support element configured to be disabled when a surrounding pH reaches a predetermined pH threshold, thus causing the device to transfer into the emptying configuration.

In some embodiments, the at least one given support element, configured to be disabled when a surrounding pH reaches a predetermined pH threshold, is at least partially made of a pH dependent polymer configured to dissolve when the surrounding pH reaches the predetermined pH threshold, preferably when the surrounding pH reaches below pH 5.

In some embodiments, the one or more support elements comprise at least one given support element configured to be disabled when a predetermined time period elapsed subsequent to positioning of the device at the ileocecal valve, thus causing the device to transfer into the emptying configuration.

In some embodiments, the at least one given support element, configured to be disabled when a predetermined time period elapsed subsequent to positioning of the device at the ileocecal valve, is at least partially made of a material configured to degrade at standard ileocecal valve environmental conditions.

In some embodiments, the at least one given support element, configured to be disabled when a predetermined time period elapsed subsequent to positioning of the device at the ileocecal valve, comprises a material configured to degrade when the surrounding pH is between 6.8 and 7.5.

In some embodiments, the one or more support elements comprise several support elements each configured to be disabled upon the device in the trapping configuration being exposed to a different activation signal, thus causing the device to transfer into the emptying configuration.

In some embodiments, the one or more support elements comprise at least one given support element configured to be disabled in less than 7 days, 3 days, 1 day or ½ day after said the device is exposed to the activation signal (preferably said activation signal comprising the exposure to ICV environmental conditions).

In some embodiments, the coupling heads may come close one to another in the trapping configuration thanks to retraction of the resiliently deformable member (i.e., the resiliently deformable member forces the coupling heads to transit/move towards each other during transfer/deformation/transit of the device from the closed configuration into the expanded configuration, such that the coupling heads are closer one to another in the expanded configuration than in the closed configuration).

The present disclosure also provides an (emptying) oral dosage form for administering to a subject, the oral dosage form being intended for use in cooperation with a device according to the present disclosure when said device is positioned at the ileocecal valve of the subject in the trapping configuration, wherein the dosage form comprises: an effective amount of an emptying agent; a coating inhibiting release of the emptying agent in the gastric environment and enabling release of the emptying agent in the ileocecal valve region; and external dimensions enabling the dosage form to be blocked by said device when reaching the ileocecal valve region; wherein the amount of the emptying agent is sufficient to cause the ileocecal valve environment to reach the at least one activation environmental condition thereby causing the device to transfer into the emptying configuration.

In some embodiments, release of a predetermined (optionally substantial, e.g., 20%, 30%, 40%, 50%, 60% or more) amount of the emptying agent downsizes the dosage form so that it is capable of passing through the trapping assembly of the device.

In some embodiments, the emptying agent comprises an amount of an acid sufficient to bring an ileocecal valve environmental pH below a pH threshold.

In some embodiments, the dosage form is a tablet having an oval or elliptical or capsule shape having a length of about 10 mm to 30 mm and a diameter of about 7 mm to 12 mm.

In some embodiments, the acid comprises short chain organic acid such as citric acid or tartaric acid.

In some embodiments, the coating comprises an enteric polymer or time dependent eroded polymer.

In some embodiments, the pH threshold is 5.0.

The present disclosure also provides an (therapeutic) oral dosage form for administering to a subject suffering from a condition which may benefit from local dispensing at the ileocecal valve region an active pharmaceutical ingredient (API), the oral dosage form being intended for use in cooperation with the device according to the present disclosure when said device is positioned at the ileocecal valve of the subject in the trapping configuration, wherein the dosage form comprises: an amount of an API effective to treat said condition; a coating for inhibiting release of said API in the gastric environment and enabling release of said API in the ileocecal valve region; external dimensions for enabling the dosage form to be blocked by said device when reaching the ileocecal valve region.

In some embodiments, the coating is such that less than 5% of the API is released in the stomach, optionally less than 2%.

In some embodiments, release of a predetermined (optionally substantial, e.g., 20%, 30%, 40%, 50%, 60% or more) amount of the API downsizes the dosage form so that it is capable of passing through the trapping assembly of the device.

In some embodiments, the dosage form comprises a controlled release formulation wherein less than 50% of the API is released from the dosage form after exiting the stomach and before reaching the ileocecal valve.

In some embodiments, the condition is an inflammatory bowel disease (IBD), optionally ulcerative colitis (US) or Crohn's disease.

The present disclosure also provides a method of treating a condition which benefits from local dispensing of an active pharmaceutical ingredient at the ileocecal valve of a subject suffering from said condition, comprising administering to said subject the device according to the present disclosure and subsequently administering the therapeutic oral dosage form according to the present disclosure, thereby treating said condition in said subject.

In some embodiments, the oral dosage form is administered to the subject while the device is positioned at the ileocecal valve in the trapping configuration.

In some embodiments, the oral dosage form is administered to the subject under fasted conditions.

In some embodiments, the oral dosage form is administered to the subject at least 2 hours, at least 3 hours, at least 4 hours, at least 5 hours, at least 6 hours, at least 7 hours, at least 8 hours, at least 12 hours, at least 24 hours, or at least 48 hours after administration of the device.

In some embodiments, the oral dosage form is administered to the subject about 5 hours to 10 hours after administration of the device.

In some embodiments, the dosage form is administered to the subject according to need.

In some embodiments, one or more subsequent dosage forms are administered to the subject at constant intervals.

In some embodiments, the one or more subsequent dosage forms are administered to the subject twice a day, every day, every 2 days, every 3 days, every 4 days, every 5 days, every 6 days, every 7 days, or at constant intervals of more than 7 days.

In some embodiments, the condition is Inflammatory Bowel Disease (IBD).

In some embodiments, the IBD is ulcerative colitis.

In some embodiments, the IBD is Crohn's disease.

In some embodiments, the treatment alleviates at least one IBD symptom in the subject.

In some embodiments, the at least one IBD symptom is selected from weight loss, macroscopic colonic damage, colonic ulceration, intestinal and/or peritoneal adhesion, diarrhea, bowel wall thickening, nauseas, vomiting, abdominal cramps, abdominal pain, intestinal bleeding, intestinal inflammation, gastrointestinal tract inflammation, rectal bleeding, tiredness, anemia, fistulae, perforations, obstruction of the bowel or a combination thereof.

In some embodiments, the treatment induces or maintains clinical remission in the subject.

In some embodiments, the oral dosage form comprises Ester levodopa or a pharmaceutically acceptable salt thereof.

In some embodiments, the oral dosage form comprises mesalamine or a pharmaceutically acceptable salt thereof.

In some embodiments, the oral dosage form comprises glatiramer acetate.

In some embodiments, the method comprises subsequently administering one or more subsequent devices according to need or at constant intervals.

The present disclosure also provides a kit comprising any device as previously disclosed, one or more cooperating therapeutic oral dosage forms as previously disclosed and/or one or more cooperating emptying oral dosage forms as previously disclosed.

The present disclosure also provides a kit comprising a device for temporary residence at an ileocecal valve of a subject suffering from a condition which may benefit from local dispensing at an ileocecal valve region of an active pharmaceutical ingredient (API) and a cooperating therapeutic oral dosage form, the device having a trapping configuration, wherein in the trapping configuration, the device is configured to be retained at the ileocecal valve of the subject when the device is positioned at the ileocecal valve; a trapping assembly configured for blocking the cooperating therapeutic oral dosage form while allowing chyme flow, when the device is positioned at the ileocecal valve; and the device is further configured to be capable of transferring from the trapping configuration into an emptying configuration in which the device is configured to pass through the ileocecal valve; the cooperating therapeutic oral dosage form comprising an amount of the API effective to treat said condition; a coating for inhibiting release of said API in the gastric environment and enabling release of said API in the ileocecal valve region; a structure enabling the cooperating therapeutic oral dosage form to be blocked by said device when reaching the ileocecal valve region until the API is effectively released.

In some embodiments, the kit (e.g., further) comprises, alternatively or additionally to the cooperating therapeutic oral dosage form, a cooperating emptying oral dosage form and the trapping assembly is (e.g., further) configured for blocking the cooperating emptying oral dosage form while allowing chyme flow, when the device is positioned at the ileocecal valve; the cooperating emptying oral dosage form comprising an effective amount of an emptying agent; a coating inhibiting release of the emptying agent in the gastric environment and enabling release of the emptying agent in the ileocecal valve region; and a structure enabling the emptying oral dosage form to be blocked by said device when reaching the ileocecal valve region until the emptying agent is effectively released; wherein the device and the cooperating emptying dosage form are configured so that release of the emptying agent causes the device to transfer into the emptying configuration.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A-3B show a perspective view and a cross section view of a hook element for use in a biasing assembly of the device shown in FIG. 1.

FIGS. 4A-4B show a front view and a cross section view of a trigger assembly cooperating with a biasing assembly for use in a device according to embodiments of the present disclosure.

FIGS. 9A-9F illustrate another example of a device according to embodiments of the present disclosure.

FIGS. 11A-11G illustrates another example of a device according to embodiments of the present disclosure.

FIG. 12 shows a device useful in a method of determining in vitro ICV retention capability of a device in accordance with embodiments of the present disclosure.

FIG. 13 shows a device useful in a method of determining in vitro a capability of a device of trapping a predetermined cooperating object while allowing chyme flow.

FIGS. 16-18 illustrate an in vivo study on a pig.

DETAILED DESCRIPTION OF EMBODIMENTS

Figure 1B:
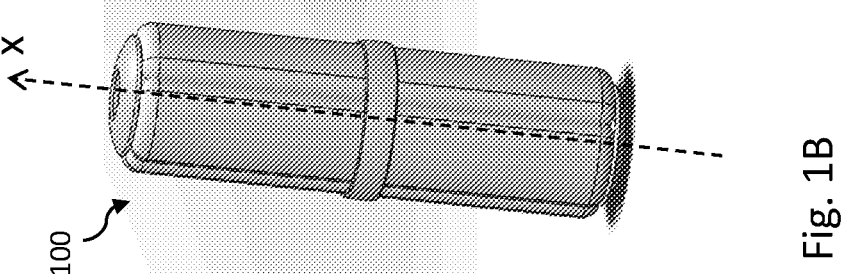
FIGS. 1A-1B illustrate perspective views of a device according to embodiments of the present disclosure respectively in a trapping configuration and in a closed configuration.

Described herein are some examples of (trapping) devices and methods useful for local drug release at the ICV region of a patient (human, or particularly adult human or young human).

In the following detailed description, numerous specific details are set forth in order to provide a thorough understanding of the subject matter. However, it will be understood by those skilled in the art that some examples of the subject matter may be practiced without these specific details. In other instances, well-known methods, procedures and components have not been described in detail so as not to obscure the description.

As used herein, the phrase "for example," "such as", "for instance" and variants thereof describe non-limiting examples of the subject matter.

Reference in the specification to "one example", "some examples", "another example", "other examples, "one instance", "some instances", "another instance", "other instances", "one case", "some cases", "another case", "other cases" or variants thereof means that a particular described feature, structure or characteristic is included in at least one example of the subject matter, but the appearance of the same term does not necessarily refer to the same example.

It should be appreciated that certain features, structures and/or characteristics disclosed herein, which are, for clarity, described in the context of separate examples, may also be provided in combination in a single example. Conversely, various features, structures and/or characteristics disclosed herein, which are, for brevity, described in the context of a single example, may also be provided separately or in any suitable sub-combination.

As used herein, the terms "about" and "at or about" mean that the amount or value in question can be the value designated some other value approximately or about the same. It is generally understood, as used herein, that it may be the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

In the present application, the following terms and their derivatives may be understood in light of the below explanations:

As used herein, the terms "local dispensing" and "local release" and their derivatives may be used to refer to a regio-specific release/dispensing of a substance at a predefined location in the GI tract, in particular at the ileocecal region.

The term "swallowable" may be used to refer to an object having dimensions enabling oral administration to a human subject. The term oral administration may refer to ingesting the object. A swallowable object may be characterized as an object being capable of being fitted in a cylinder, wherein a length of the cylinder is, for example, about 35 mm or less and a diameter of the cylinder is, for example, about 12 mm or less.

As used herein, the term "ileocecal region", "ICV region" or "ileocecal valve region" may be used to refer to a region substantially consisting of the lower part of the small intestine (terminal ileum), the ileocecal valve, the cecum and the ascending colon.

As used herein "structural rigidity" may refer to the ability of an object to maintain its shape while being exposed to an external load.

The term "environmental conditions" may refer to biological, physical and/or chemical conditions of an environment i.e., a medium or milieu in which the device is positioned or intended to be positioned. The environmental conditions may include for example, temperature, pH, atmospheric pressure, gravity, electromagnetic field, vibration, glucose concentration, oxygen concentration, enzyme concentration, etc. In a predetermined part of the GI tract, for example the ICV region, standard environmental conditions may refer to average physiological conditions observed in said part of the GI tract. For example, standard pH conditions for different parts of the human GI tract are summarized in the table below:

| GI segment | pH along the gastrointestinal tract (1) | | |
| --- | --- | --- | --- |
| | median | 25th percentile | 75th percentile |
| stomach | 1.5 | 1.1 | 1.8 |
| duodenum | 6.4 | 5.7 | 6.9 |

17

-continued

| | pH along the gastrointestinal tract (1) | | |
|---|---|---|---|
| GI segment | median | 25th percentile | 75th percentile |
| proximal small intestine | 6.6 | 6.2 | 7.1 |
| mid small intestine | 7.1 | 6.6 | 7.4 |
| distal small intestine (including ICV) | 7.3 | 7.0 | 7.5 |
| cecum | 5.7 | 5.2 | 6.3 |
| ascending colon | 5.6 | 5.1 | 6.5 |
| transverse colon | 5.8 | 5.3 | 6.4 |
| descending colon | 6.6 | 6.3 | 7.0 |
| Rectum | 6.6 | 5.8 | 7.1 |

As used herein "degradability" may refer to the ability of a device to lose structural rigidity under certain physiologic conditions. The degradation products may be excretable and/or absorbable by the body.

As used herein, the term "closed configuration" of a device may be the state of the device prior to administration where the device has a size that is suitable for swallowing or for oral manipulation with an endoscope or suitable for administration by colonoscope (lower endoscopy). The closed configuration may also be referred to as a swallowing or swallowable configuration, collapsed configuration, compact configuration, compressed configuration, deflated configuration, folded configuration or the like.

As used herein, the "trapping configuration" of the device may be the state of the device when it resides at the ileocecal valve. In some embodiments, the device may be orally administered, for example via ingestion or via upper endoscopy, and the device may be delivered in the trapping configuration in the small intestine and thereafter self-transits to the ICV due to GI motility. The trapping configuration of the device notably prevents passage of the device through the ileocecal valve and enables chyme flow therethrough. The trapping configuration may also be referred to as a configuration expanded, opened, inflated, unfolded or the like.

The term "dosage form" as used in the present disclosure refers to solid dosage forms which may include an active pharmaceutical ingredient. Some dosage forms according to the present disclosure may include an API (and optionally one or more pharmaceutically acceptable excipients) and may be referred to as a therapeutic dosage form. In some embodiments, the dosage form includes an API useful in treating a disease or disorder for which dispensing of the API at the ICV is beneficial.

Some dosage forms according to the present disclosure may not include an API but may, for example, instead include an emptying agent for modifying the ICV standard environmental conditions to cause the device according to some embodiments of the present disclosure to transfer from the trapping configuration into the emptying configuration. Such a dosage form may optionally include one or more pharmaceutically acceptable excipient. The latter dosage forms may be referred to as "emptying dosage forms". In some embodiments, the emptying agent is a pharmaceutically acceptable ingredient in an amount effective to cause transfer of the device into the emptying configuration. In some embodiments the emptying agent is an acidic ingredient including citric acid, tartaric acid and the like. The dosage forms (comprising API or emptying agent) may include, for example, tablets, pellets or capsules. Tablets may have common tablet shapes such as round, standard convex, compound cup, oval, bullet, triangle, diamond, etc. Capsules may carry a solid (e.g., tablet, particles, granulates) or liquid load. Dosage forms generally have dimensions such as to fit into a cylinder having a length from 10 mm to 30 mm and a diameter from 7 mm to 12 mm. In some embodiments, the dosage form comprises a mixture of active ingredient(s) (API or emptying agent) and inactive excipients including one or more of filler, binder, lubricant, diluent, preservative and the like. In some embodiments, the dosage form comprises at least one coating, preferably a pH dependent coating that enables delivery of a substantially intact dosage form to the ICV region. Substantially intact may refer to the dosage form being at least capable of being blocked by the trapping device when reaching the ICV. Substantially intact may also refer to the dosage form having undergone less than 50%, less than 40%, less than 30%, 20%, less than 15% less than 10% or less than 5% downsizing before reaching the ICV and/or to the dosage form having released less than 50%, less than 40%, less than 30%, 20%, less than 15% less than 10% or less than 5% of the API or of the emptying agent before reaching the ICV. In some embodiments the dosage form includes an external coating comprising one or more enteric polymer. In some embodiments the dosage form includes one or more pH dependent coating. In some embodiments, the dosage form includes a time dependent coating such as HPMC and or ethyl cellulose and optionally a pore forming agent. In some embodiments, the dosage form is configured to begin to downsize and/or release API or the emptying agent in the ICV region between 72 hours and 4 hours post administration. In some embodiments, the dosage form is configured to downsize and or release API in the ICV region 72 hours after administration, 60 hours after administration, 48 hours after administration, 36 hours after administration, 30 hours after administration, 24 hours after administration, 18 hours after administration, 15 hours after administration, 12 hours after administration, 11 hours after administration, 10 hours after administration, 9 hours after administration, 8 hours after administration, 7 hours after administration, 6 hours after administration, 5 hours after administration or 4 hours after administration.

The term "external envelope" may be used to refer to a hull separating internal and external portions of the device. For example, the external envelope of the device may comprise an outer surface of the device.

The term "pharmaceutically acceptable" refers to a material that is not biologically or otherwise unacceptable when used for the purposes of the present disclosure. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration. The materials used for manufacturing the device in accordance with the present disclosure may be pharmaceutically acceptable.

The term "pH dependent polymer" may refer generally to a polymer whose degradability or dissolubility changes depending on the pH of a surrounding solution. For example, in some embodiments of the present disclosure a trigger assembly may include one or more support elements which may be at least partially made of a pH dependent polymer so that the one or more support elements do not degrade at a standard ICV environmental conditions (i.e., ICV standard pH of about 6.8-7.5) while do degrade at an acidic pH (e.g., pH of about 5.0 or 4.0 or 3.0). A type of pH dependent polymer is an enteric polymer. An enteric polymer may be understood as polymer that do not readily dissolve or degrade under the typical pH and other physical conditions of a human stomach, but that do dissolve or degrade at pH and other physical conditions of the intestinal tract of a human, i.e., the conditions that exist following passage from the stomach through the pylorus (i.e., pH>5). For example, in some embodiments of the present disclosure the device may comprise a container in which the device can be fitted in the closed configuration and the container may be at least partially made of an enteric polymer so that the container dissolves after passage in the stomach and the device can be released in the small intestine. In some embodiments, as described below, the trigger assembly may include one or more support elements at least partially made of an enteric polymer or of a pH dependent polymer. When the singular form of "pH dependent polymer" is used, this can refer to one enteric polymer, a mixture of two or more enteric polymers, or a mixture of polymers of which at least one is a pH dependent polymer, as long as the resulting mixture is pH dependent in nature.

Local release of therapeutic agents to the ICV and ascending colon may have therapeutic benefit when used in various medical conditions. Non limiting examples include:

a. Treatment of Inflammatory Bowel Disease (IBD) including Ulcerative Colitis (UC) and Crohn's disease (CD). The ileocecal junction and ascending colon are inflammation sites (especially in pancolitis). Effective treatment may be achieved when local and/or topical exposure of the drug in the inflamed tissue is obtained (i.e., high local concentration and long exposure duration). Examples of useful APIs include steroids (budesonide), mesalamine, 6-mercapto-purine, etc.

b. Treatment of colon disease, including colon cancer and colonic microbial diseases. Examples of colonic cancer drugs include including angiogenesis inhibitors, check point inhibitors, metabolite inhibitors etc. Drugs currently approved in the US for treating colon cancer, include Irinotecan Hydrochloride, Capecitabine, Oxaliplatin, Erbitux, Fluorouracil, Leucovorin Calcium, Irinotecan Hydrochloride, Trifluridine, Tipiracil Hydrochloride, Oxaliplatin, Regorafenib, Capecitabine, Ziv-Aflibercept. Colon infections may be caused, for example, by parasites, bacteria, viruses, fungi. Useful anti-microbials include amoxycillin neomycin, rifaximin, anthracyclines, bleomycins, mitomycin, dactinomycin, and plicamycin. A health care professional may identify a relevant antibiotic for a particular disease, from for example, the WHO publication "Critically important antimicrobials for human medicine", (ISBN: 978-92-4-151552-8; 6th revision).

c. Improvement of absorption and bioavailability of therapeutic agents; for example, achieving therapeutic systemic plasma concentrations having minimal fluctuations to better enable efficacy and safety. For example, Vitamin B (optionally given with absorption enhancer) which is known to be absorbed mainly in the ileocecal junction. Another example is GLP-1 receptor agonists given with absorption enhancer such as SNAC to be released and absorbed in the targeted site (ICV). Further examples include esterified levodopa (eLD), to improve the systemic exposure compared to LD. Actually, experiments have shown that when eLD is given in a standard oral dosage form (targeted to the upper GI tract) although eLD has a better solubility and passive permeability profile, no significant improvement in systemic exposure is achieved. This is likely due to extensive pre-systemic metabolism of eLD into LD. Therefore, local release of eLD in using devices and methods of the present disclosure to the ICV region, which has lower esterase activity than the upper GI tract, may enable better systemic exposure and optimize the therapeutic advantage of eLD (Laizure et al, Pharmacother. 2013; 33(2): 210-222; Itoh et al, J Pharma Sci, 99:1, 2010; Fix et at, Pharmaceutical Res, 6:6 1989). Additionally, targeting the ICV region may have significant advantage over the current oral LD treatment. Actually, in the proximal intestine, LD absorption is carried out by an amino acid transporter, which is in competition with food originating amino acids. By contrast, in the terminal ileum the absorption of eLD is mostly passive and no interference is expected, leading to a more stable exposure of drug. Further examples also include Vitamin B12 which is known to be poorly absorbed in the small intestine and known to be absorbed mainly in the ileocecal region. Drugs that can benefit from prolonged retention and release in the ICV region include other esterified drugs including Tenofovir disoproxil, Adefovir dipivoxil, Prasugrel and the like. Tenofovir disoproxil is given as ester prodrug since it has much better absorption compared to the drug itself. Still, the bioavailability of the prodrug is only about 30% due to extensive intestinal esterase degradation. By targeting Tenofovir disoproxil to ICV region having lower esterase activity (Van Gelder, et al. (2000). Species-dependent and site-specific intestinal metabolism of ester prodrugs. Int J of Pharmac. 205. 93-100.) a more consistent absorption and bioavailability may be achieved.

d. Changing the administration site of known drugs. In general, there are examples of drugs, that upon changing the administration site were found to be beneficial for different, new indications. For example, Copaxone® (glatiramer acetate), which is normally given subcutaneously for the treatment of multiple sclerosis has been shown to be effective in treating UC when given topically (see Yunliang Yao et al., "Glatiramer acetate ameliorates inflammatory bowel disease in mice through the induction of Qa-1-restricted CD8+ regulatory cells", Eu Jl Immunol, 43:1, pg 125-136). The present disclosure, which introduces a new site of drug deposition and or absorption holds a potential for treating a variety of indications using APIs not necessarily intended for that particular use (e.g., administration at the ICV or upper colon).

In some embodiments, the API is a small molecule. In some embodiments, the API is a prodrug. In some embodiments, the API is a pharmaceutically acceptable salt of an API. In some embodiments, the API comprises amino acid or nucleotides. In some embodiments, the therapeutic agent may be a combination of two or more therapeutic agents. A non-limiting list of APIs includes anti-retroviral agents; CYP3A inhibitors; CYP3A inducers; protease inhibitors; adrenergic agonists; anti-cholinergics; mast cell stabilizers; xanthines; leukotriene antagonists; glucocorticoids treatments; local or general anesthetics; non-steroidal anti-inflammatory agents (NSAIDs, e.g., naproxen); antibacterial agents; anti-fungal agents; sepsis treatments; steroidals; local or general anesthetics; monoamine oxidase inhibitors; hypothalamic phospholipids; endothelin converting enzyme (ECE) inhibitors; opioids; thromboxane receptor antagonists; potassium channel openers; thrombin inhibitors; growth factor inhibitors (e.g., modifiers of EGF, PDGF activity); anti-cytokines (e.g., anti-TNF activity); anti-platelet agents (e.g., aspirin); anticoagulants; heparins; renin inhibitors; neutral endopeptidase (NEP) inhibitors; vasopeptidase inhibitors (dual NEP-ACE inhibitors; HMG CoA reductase inhibitors (e.g., statins); squalene synthetase inhibitors; fibrates; bile acid sequestrants; anti-atherosclerotic agents; MTP Inhibitors; calcium channel blockers; potassium channel activators; alpha-muscarinic agents; beta-muscarinic agents; antiarrhythmic agents; diuretics; thrombolytic agents; anti-diabetic agents; mineralocorticoid receptor antagonists; aP2 inhibitors; phosphodiesterase inhibitors; protein tyrosine kinase inhibitors; antiproliferatives; immunosuppressants; antimetabolites; antibiotics; enzymes; farnesyl-protein transferase inhibitors; hormonal agents (e.g., cortisone); microtubule-disrupter agents; plant-derived products (e.g., taxanes); topoisomerase inhibitors; prenyl-protein transferase inhibitors; cyclosporins. Listings of additional examples of known therapeutic agents can be found, for example, in the United States Pharmacopeia (USP), Physician's Desk Reference (Thomson Publishing), and/or The Merck Manual of Diagnosis and Therapy, 20th ed. (2018) Robert S. Porter, ed., Merck Publishing Group, or, in the case of animals, The Merck Veterinary Manual, 11th ed., Susan E. Aiello and Michael A. Moses eds., Merck Publishing Group, 2016; and "Approved Drug Products with Therapeutic Equivalence and Evaluations," published by the United States Food and Drug Administration (F.D.A.) (the "Orange Book").

Further provided herein is a method of treating a condition which may benefit from local dispensing of an API at the ICV of a subject suffering from the condition. The treatment includes orally administering to the subject a trapping device as described herein and subsequently administering an oral dosage form that is configured to cooperate with the device comprising the API, thereby treating said condition in said subject.

"Treating" as used herein encompasses, e.g., inducing inhibition, regression, clinical remission or stasis or inhibiting, reducing the severity of, eliminating or substantially eliminating, or ameliorating a symptom of the disease or disorder, e.g., IBD including Crohn's disease, UC etc.

"Inhibition" of disease progression or disease complication in a subject means preventing or reducing the disease progression and/or disease complication in the subject.

A "symptom" associated with a disease or disorder disclosed herein includes any clinical or laboratory manifestation associated with the disease or disorder and is not limited to what the subject can feel or observe. A non-limiting example includes the following symptoms for IBD: weight loss, macroscopic colonic damage, colonic ulceration, intestinal and/or peritoneal adhesion, diarrhea, bowel wall thickening, nauseas, vomiting, abdominal cramps, abdominal pain, intestinal bleeding, intestinal inflammation, gastrointestinal tract inflammation, rectal bleeding, tiredness, anemia, fistulae, perforations, obstruction of the bowel or any combination thereof. Symptoms of other conditions are known in the art and are identified by a medical practitioner.

The device according to the present disclosure may have any physical configuration that is compatible with certain basic functionalities.

First, it is configured for being administered to a human. For example, the device can be deformed (e.g., folded) from a trapping configuration into a closed configuration and locked by a locking element (e.g., a capsule) so as to be sized and shaped for oral administration i.e., ingestion. The locking element may substantially maintain the device integrity prior to entry into the stomach and until it reaches the small intestine. The locking element may dissolve after (e.g., within 1 hour) exposure to small intestine environmental conditions. The device may also, in some embodiments, be configured to be positioned by endoscopy—i.e., upper endoscopy or colonoscopy—at the ileocecal valve in the trapping configuration. In some embodiments, the device in the collapsed configuration may be manipulated with the endoscope and released in the small intestine, in the ICV region or at the ICV in the trapping configuration. In some endoscopically administered embodiments, the device may be inflatable between a collapsed/deflated configuration and the trapping configuration. The device may be positioned at the ICV in the collapsed configuration and inflated in the trapping configuration thereafter. In some upper endoscopy administered embodiments as well as in some orally administered (ingested) embodiments, the device may be administered to the subject under fasted conditions.

Second, in orally administered/ingestible embodiments, the device is configured for being capable of transiting through the GI until the ileocecal valve. For example, the device may be contained in a capsule made of an enteric polymer which does not dissolve in standard stomach environmental conditions (fasted and/or fed) but dissolves in standard small intestine environmental conditions. Further, the device in the trapping configuration may be configured to enable chyme flow in the small intestine while transiting to the ileocecal valve. Furthermore, the device may also be configured to position at or in proximity of the ileocecal valve due to the subject GI motility.

Third, the device in the trapping configuration is configured for retention at (i.e., directly before, proximal to) the ileocecal valve (i.e., not to pass through the ileocecal valve) in standard GI motility conditions. For example, the device in the trapping configuration may be sized and/or shaped and/or have a structural rigidity that prevents passage through the ileocecal valve of a standard subject under standard GI motility conditions.

Fourth, the device is configured for being capable of transferring into an emptying configuration which allows passage through the ileocecal valve, and optional excretion through the subject's body. For example, the device may include a trigger assembly causing the device to transfer into the emptying configuration when activated. The trigger assembly may be configured to be activated when the device in the trapping configuration is exposed to an activation signal such as being exposed to standard ileocecal region environmental conditions for a predetermined residence time period or such as a surrounding environment reaching a predetermined set of environmental conditions (e.g., a pH threshold). The device may be configured to include one or more structural weak points which may cause the device to swiftly fall apart into the emptying configuration when the trigger assembly is activated.

Fifth, the device in the trapping configuration is configured to allow chyme flow through the ileocecal valve while blocking (trapping) cooperating rigid objects (e.g., dosage forms) having predetermined external dimensions. Trapping of dosage forms by the device may enable dispensing locally a drug in the ileocecal region. In general, cooperating objects may have one or more of the following features:

i. Be configured for ingestion i.e., made of pharmaceutically acceptable material(s) and have swallowable dimensions.

ii. Have a hull substantially occupying a volume larger than a cylinder of a length of 7 mm and a diameter of 8 mm.

iii. Have a hull substantially occupying a volume larger than a sphere of 7 or 8 mm diameter;

iv. Embed an active agent (therapeutic agent or an emptying agent). The therapeutic agent or emptying agent being configured to be (exclusively or at least mainly) released at the ICV.

v. Be capable of downsizing so as to pass through the trapping device after the embedded therapeutic agent or emptying agent is significantly released.

Optionally, the device may carry a load of an active pharmaceutical ingredient, and further be configured for releasing at least partially the active pharmaceutical ingredient while allowing chyme flow when the device is positioned at the ileocecal valve and in the trapping configuration.

The expression "carrying a load of an active pharmaceutical ingredient" as used in the present disclosure refers to the fact that the device securely contains a quantity of said API in the state of the device prior to administration (e.g., the closed configuration). By "securely", it is meant that prior to administration (e.g., the closed configuration), the device securely contains a quantity of said API located inside a convex hull of the device, and said API is not extractible unless deforming the outer shape of device, due to physical barriers formed all around the API by components and/or material. In other words, the device may carry an embedded dosage form including an API i.e. a therapeutic dosage form. Thus, the device may be enabled to be administered and securely carry/transport with itself a certain amount of the API to the ICV. Then, when the device is in the trapping configuration and positioned at the ICV, the device may be configured for releasing at least part (e.g., all of) said (initially carried) load of the API. Indeed, the device may be configured for the API to be exposed to chyme flow so as to release the API, at least when the device is in the trapping configuration during transit in the small intestine and or when positioned at the ICV. The release may optionally be over a certain period of time, e.g., longer than one minute, ten minutes, thirty minutes, one hour, two hours, five hours, twelve hours, one day, or one week. In other words, the API load may be configured to erode, diffuse or dissolve from within the device.

The device may present a structural rigidity substantially independent of the load of the API. The device may notably maintain its expanded shape while the API is being released, and in particular even if the API has been fully released. In particular, the device may be configured such that, when administered to a subject but without any load of API, the device is structurally rigid enough to be retained at the ileocecal valve of the subject. As such, the load of the API may be unsupportive of the device's structure.

The device may carry a load of the API in any manner, and optionally in several different manners. The device may embed at least part of the load of the API inside (e.g., enclosed in) or on (e.g., mounted onto or attached to) one of its components. Said at least part of the load may remain embedded in the device. In other words, said at least part of the load may be securely attached to the device even in the expanded configuration, such that said at least part of the load is not extractible (apart from release of the API) unless exerting a force above a predetermined threshold. Alternatively or additionally, at least part of the carried load may be detachable from the device when the device deforms into the expanded configuration.

The device may for example comprise an inner (available) space in the closed configuration. The inner space may contain (e.g., lodged therein and/or unattached) at least part of the load of the active pharmaceutical ingredient. The inner space may be an interstice left (i.e. present) between or flanked by components of the device. Such examples optimize space left between components of the device by using it for API loading. In examples, the device may comprise at least two flexible arms, each arm having a first end and a second end, a first and second coupling heads, wherein the first end of each arm is coupled to the first coupling head and the second end of each arm is coupled to the second coupling head, and a resiliently deformable member configured to force the coupling heads together to bend the arms thereby biasing the device in the expanded configuration. In such examples, the inner space may be formed in the closed configuration around the resiliently deformable member and between the arms and the coupling heads. In options, the device may further comprise a support tube, the resiliently deformable member being arranged inside the support tube. In such options, the inner space may comprise an interstice formed between the support tube and the resiliently deformable member. In examples of such options, the support tube may have apertures (on its peripheral wall) which provide exposure (i.e., fluid communication with the physiological environment surrounding the device) to the cavity. This allows fine control of the API release. In particular, the apertures may present a design which provides a predetermined release rate. Alternatively or additionally, the exposure apertures may be coated, for example with an enteric coating, so as to expose the contained API load only when desired, for example when the device reaches the ICV region. Alternatively, the exposure apertures may be uncoated.

Alternatively or additionally, at least one material portion or at least one component of the device may comprise an exposed cavity (i.e., a substantially void space inside a portion of material and having a peripheral wall substantially enclosing the space). In such a case, the exposed cavity may contain (e.g., enclosed therein and/or unattached) at least part of the load of the active pharmaceutical ingredient. The cavity is open to the device environment, at least when the device is in the expanded configuration. Thus, the load of the API may flow/erode from the cavity when the device is in the expanded configuration. The cavity may be formed within a peripheral wall having apertures which provide exposure of the exposed cavity. Such examples allow simple manufacturing and fine control of the API release. In particular, the apertures may present a design which provides a predetermined release rate. Alternatively or additionally, the exposure apertures may be coated, so as to expose the contained API load only when desired, or on the contrary uncoated. In examples, the device may comprise at least two flexible arms, and one or more (e.g., all) of the arms may comprise such cavity (e.g., within one or more—e.g., each—arm section when the arm is articulated and/or composed of a set arm sections).

Alternatively or additionally, at least one material portion or at least one component of the device may comprise an exposed recess. In such a case, the exposed recess may lodge (i.e., be filled with) at least part of the load of the active pharmaceutical ingredient (e.g., press-fitted in the recess, or formed by molding inside the recess). Such examples allow simple manufacturing. In examples where the device comprises a support tube, the support tube may have one or more peripheral groove recesses. Each peripheral groove may lodge the API, for example a ring-shaped (e.g., solid) form containing the API. Alternatively or additionally, the arms may comprise exposed recesses. Each exposed recess may be coated at its opening, so as to expose the contained API load only when desired, or on the contrary uncoated.

Alternatively or additionally, at least one material portion or at least one component of the device may comprise a coating on an exposed surface, the coating containing at least part of the load of the active pharmaceutical ingredient. For example, each arm section and/or a support tube may be coated with any mixture containing the API.

The load of the API may present any texture, shape, and/or composition. For example, the API may be contained in a solid form, in a semi-solid form, as powder, as a gel texture, and/or in a liquid. In addition, the API may be contained in one texture, shape, and/or composition at one location, and in another texture, shape, and/or composition at another location. Furthermore, the device may carry several APIs, for example cooperating together to treat a medical condition. The load of the API may contain one or more pharmaceutically acceptable excipients. The one or more excipients may be inactive and/or include one or more of filler, binder, lubricant, diluent, preservative, control release agent, disintegrant and the like. Solid forms of the API may include one or more tablets, and/or pellets. The carried tablets (e.g., pills) may have common tablet shapes such as round, standard convex, compound cup, oval, bullet, triangle, diamond, etc., so as to fit the cavity, recess, groove, inner space designed to accommodate the tablet.

The device may be unable to release the API (at all) when the device is in the closed configuration. The device may further be optionally unable to release the API unless the device is in the trapping configuration. For example, in some embodiments of the present disclosure the device may comprise a container in which the device can be fitted in the closed configuration, and the container may form a physical barrier preventing release of the API carried by the device prior to the container dissolving and the device thereby transferring from the closed configuration into the expanded configuration. In some embodiments, the device includes an API useful in treating a disease or disorder for which dispensing of the API at the ICV is beneficial.

The device may carry any quantity of the API. For example, the load of the active pharmaceutical ingredient (e.g., possibly including excipients) may occupy at least 5%, 10%, 15%, 20%, or 25% of the volume of a convex hull of the device in the closed configuration. In other words, the API may be contained in an embedded dosage form or formulation, and the device may offer in the closed configuration enough free space such that at least 5%, 10%, 15%, 20%, or 25% of the volume of its convex hull is occupied by (accommodated with) the form/formulation. The type and quantity of API load may be determined by a healthcare professional.

The load of API carried by the device may be distinct and separate from the support elements (e.g., timers). Each support element may be integrally formed, and the load of the API may be elsewhere. In examples, the support elements may be located inside the coupling heads, while the carried load of the API may be located between the coupling heads and the arms (i.e., outside the coupling heads). Optionally, the support element may comprise none of the API. In variations, the device may comprise one or more integrally formed blocks both forming a support element and carrying at least part of the load of the API. While releasing the API, the blocks erode to a point of degradation, thus triggering emptying of the device.

Figure 1A:
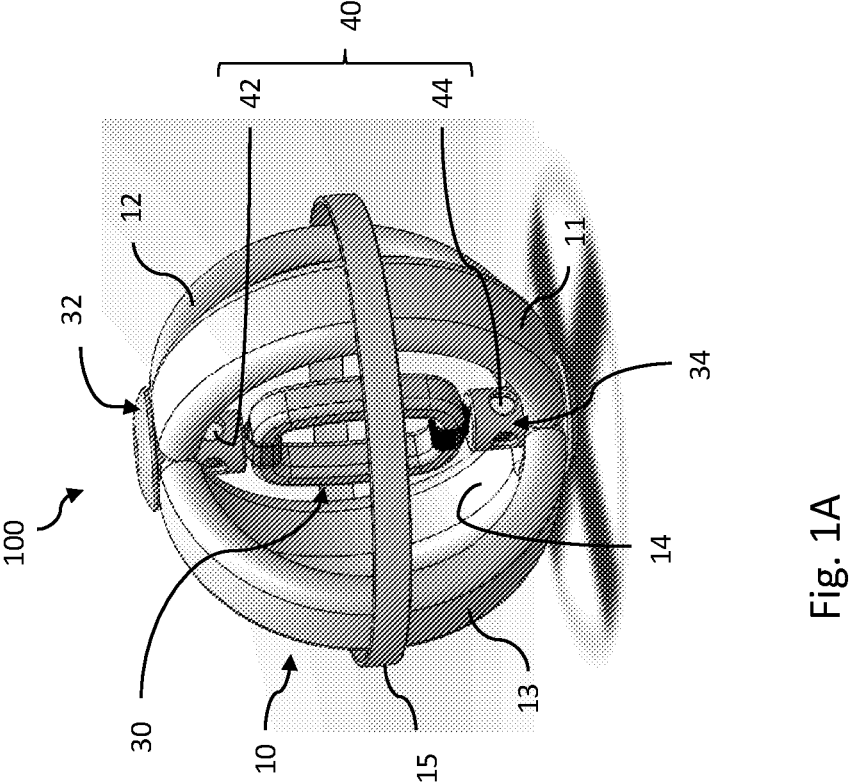

FIGS. 1A and 1B show an example of a device 100 according to the present disclosure respectively in a trapping (open) configuration and in a swallowing (closed) configuration.

The device 100 is intended to be orally administered—in the closed configuration—to a patient for temporary residence—in the trapping configuration—at an ileocecal valve of said patient. In some embodiments, the device in the closed configuration may be capable of passing through the ileocecal valve of the patient. In some embodiments, the external envelope of the device in the closed configuration has dimensions enabling passage through the ileocecal valve and the device in the emptying configuration has an external envelope similar to the device in the closed configuration (see FIG. 5A). Basically, the device in the closed configuration may be capable of being fitted into a cylinder of about 35 mm length or smaller and of about 12 mm diameter or smaller.

In the trapping configuration, the device 100 is configured to be retained at the ileocecal valve and resist standard GI motility. In other words, the device 100 may be configured to not pass through the ileocecal valve of the patient when it is positioned at the ileocecal valve. The device 100 may include a flexible frame. The device 100 in the trapping configuration may have an uncompact shape while the device in the closed configuration may have a compact shape. The device 100 in the trapping configuration may have a spherical or ovoid, tetrahedral, cuboidal or semi spherical outer shape. In some embodiments, the dimensions of the device in the trapping configuration may be such that the device cannot pass through an orifice of about 17 mm diameter and preferably of about 20 mm. Generally, the device 100 may have a shape and/or a size and/or a structural rigidity enabling the device to be retained at the ileocecal valve. The capability of the device 100 to be retained at the ICV may be defined in accordance with methods described in details herein below with reference to FIG. 12.

The device 100 includes a trapping assembly 10 configured for blocking cooperating objects while allowing chyme flow when the device is positioned in the trapping configuration at the ICV. The cooperating objects may be ingested objects e.g., dosage forms. Particularly, the device in the trapping configuration may be configured to block objects having dosage form dimensions. For example, the device in the trapping configuration may be configured to block cylindrical or other commonly shaped tablet dosage forms. Particularly, the device in the trapping configuration may be configured to block spherical beads of a diameter larger than a trapping threshold diameter of e.g., 7 mm, 8 mm, 9 mm, 10 mm, 11 mm or 12 mm. In the following, the predetermined dimensions of the ingested objects may refer to the dimensions of said ingested objects when reaching the ileocecal valve region i.e., after transit through the GI tract. In some embodiments, the capability of the device 100 to block cooperating objects (such as dosage forms with specific dimensions when reaching the ileocecal valve region after GI transit) while allowing chyme flow may be defined in accordance with methods described in details herein below with reference to FIGS. 12 and 13. In some embodiments, the device 100 may be configured so as to allow passage of spherical beads of a diameter lower than a passage threshold diameter of e.g., 3 mm, 4 mm, 5 mm or 6 mm. In some embodiments, the frame of the device is configured to form the trapping assembly.

The device 100 is further configured to transfer into an emptying configuration in which it can pass through the ICV under standard GI motility conditions. In some embodiments, the capability of the device 100 to pass through the ICV in the emptying configuration may be defined in accordance with methods described in details herein below with reference to FIG. 12.

The device 100 may be reversibly deformable from the trapping configuration of FIG. 1A into the closed configuration of FIG. 1B.

The device 100 may comprise a body 10, an opening assembly in the form of a biasing assembly 30 and a trigger assembly 40.

The body 10 may be formed of several (e.g., four) flexible arms 11-14 joined to each other by both ends. The body may form the frame of the device 100. The biasing assembly 30 may be configured to bend the flexible arms 11-14 in a rounded shape. When not bent (i.e., when the biasing of the biasing assembly is overcome), the arms 11-14 may substantially extend in the direction of a longitudinal axis X. When not bent (i.e., when the biasing assembly 30 is disabled), the arms 11-14 may be disposed to form a hollow tube. The arms 11-14 may be made of silicone. In some embodiments, the body 10 may be made from a hollow tube of silicone comprising four longitudinal slits.

The device 100 may further comprise a circumferential belt 15 disposed around the four flexible arms. The circumferential belt 15 may be disposed in a plane substantially perpendicular to the longitudinal axis X. The circumferential belt 15 may be made of an elastic material so as to allow the flexible arms 11-14 to open into the trapping configuration without substantial restriction. For example, the arms and the circumferential belt may be made of silicone of different thicknesses or different grade (e.g., different shore A). For example, the flexible arms may be made of silicone shore 80 A and the peripheral belt may be made of silicone shore 50 A. Generally, the device may be configured for remaining in the closed configuration for a shelf lifetime period of about 2 to 52 weeks and maintain its functionalities. The device may be made of a material with low creep (i.e., low tendency to have gradual permanent deformation under the influence of persistent mechanical stresses, e.g., the small intestine wall pressure). The circumferential belt 15 may alternatively be made of a material that is flexible but not elastic.

The circumferential belt 15 may have a structural function, for example stabilize the platform formed by the device 100 when open in the expanded configuration. This improves ICV retention.

Figures 2A, 2B:
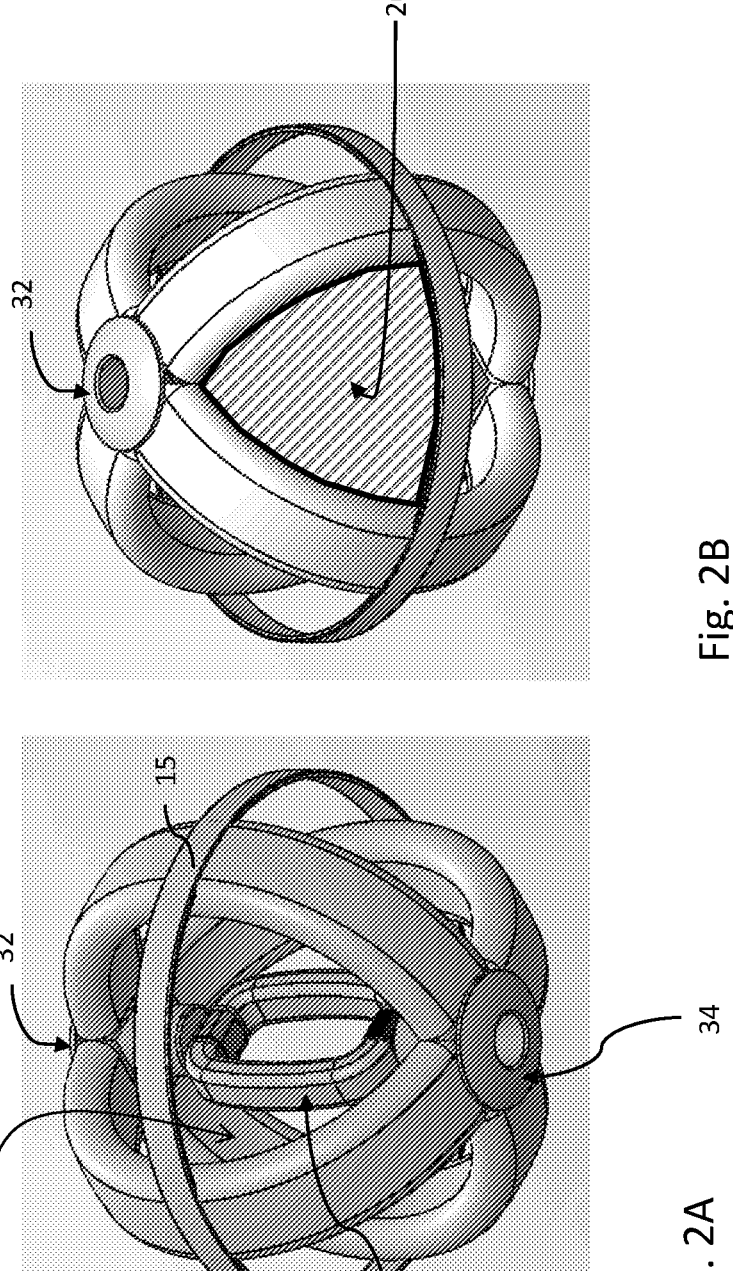
FIGS. 2A-2B show perspective views of the device shown in FIG. 1 in the trapping configuration.

When the device 100 is in the open (trapping) configuration, the body 10 and the circumferential belt 15 may form a tridimensional meshed structure. The openings 20 (see FIG. 2B in which one of opening 20 is illustrated by a dashed surface) formed between the flexible arms 11-14 and the circumferential belt 15 in the open configuration may define a mesh of said meshed structure. The openings 20 may be configured to enable trapping of cooperating objects. In other words, the device 100 may be configured so that in the trapping configuration, the openings 20 formed between the arms 11-14 and the circumferential belt 15 are dimensioned so as to trap cooperating objects.

The biasing assembly 30 may be configured to resiliently hold (bias) the device 100 in the trapping configuration. In other words, the biasing assembly 30 may be configured to cause the device to tend to resiliently return from the closed configuration into the trapping configuration.

The biasing assembly 30 may comprise two coupling hooks 32, 34 and an elastic member 35. A first end of each flexible arm may be coupled to the first coupling hooks 32 and a second end of each flexible arm may be coupled to the second coupling hook 34. More details regarding the arrangement of the coupling hooks 32, 34 and the elastic member 35 are given hereinafter with reference to FIGS. 4A-4B.

The trigger assembly 40 is configured to cause the device 100 to transfer from the trapping configuration into the emptying configuration upon activation. The trigger assembly 40 comprises two support elements 42, 44 configured to temporary maintain the device into the trapping configuration. The support elements 42, 44 are configured to be disabled when the device in the trapping configuration is exposed to a predetermined activation signal. The support elements 42, 44 are configured to cooperate with the biasing assembly 30 so that, when the support elements 42, 44 are disabled, the biasing assembly 30 is irreversibly disabled and the device 100 transfers into the emptying configuration. The trigger assembly 40 may be configured to cause additional degrading of the device such as for example, disassembling into two or more subcomponents, additional decline of shape, size and/or structural rigidity.

For example, the support elements 42, 44 may be configured to be disabled after the device 100 is exposed to standard ICV region environmental conditions for a predetermined residence time period, for example of one day, two days, three days or more and/or twelve weeks or less (e.g., any time period from 1 to 12 weeks, such as one month, one week, two weeks, three weeks, or even one day or two days). In other words, the trigger assembly 30 may activate after the device is positioned at the ICV for a predetermined time period or after a predetermined time period elapsed subsequent to swallowing of the device. In some embodiments, support elements configured to be disabled after the device is exposed to standard ICV region environmental conditions for a predetermined residence time period may be made of a combination of a material degrading at standard ICV environmental conditions (such as Eudragit EPO) and a control release delay material (such as a polymer carrier).

The support elements 42, 44 may also or alternatively be configured to be disabled after the device is exposed to a predetermined set of activation environmental conditions. For example, the support elements 42, 44 may be configured to be disabled when a surrounding environment reaches (e.g., below) a predetermined pH threshold (e.g., pH 3, 4 or 5). For this purpose, the support elements 42, 44 may be erodible elements at least partially made of a material configured to dissolve (or degrade) when the surrounding pH reaches the predetermined pH threshold. In some embodiments the support elements 42, 44 may be at least partially made of a material dissolving at (i.e., when the pH reaches) the predetermined pH threshold. For example, the support elements may be made of an acid-soluble polymer. For example, the support elements 42, 44 may be at least partially made of a material soluble at pH below 5 such as Eudragit® E PO).

In some embodiments, the support elements 42, 44 may have a pin shape. Pin-shaped support elements 42, 44 of Eudragit® E may be manufactured as follows: a Hot Melt Extrusion machine is set to for example about 130° C. Eudragit® E powder is fed into the HME machine for example by a gravimetric feeder at a rate of 1 kg/hr. The HME machine snail speed is set to 100 rpm. The melted material is drawn from the HME machine, it is forwarded as strands onto a conveyor belt to cool. Once cooled, the strand is chopped by a chopping machine to a pin shape of about 1.5 mm diameter and 2 mm length.

In some embodiments, the support elements 42, 44 may be at least partially made of a material dissolving in standard ICV region environmental conditions, such as hydroxypropylmethylcellulose (HPMC-AC), and coated with a material dissolving at the predetermined pH threshold, such as Eudragit® E PO. Such pin-shaped coated support elements may be manufactured as follows: Powder of HPMC AC is premixed with Dibutyl sebacate (DBS) in ratio of 8:1 in DIOSNA mixer for 5 minutes at 500 rpm. After premixing, the mixture is placed at room temperature for 24 hr so that the polymer and plasticizer settle together. After 24 hr, the mixture is fed into the HME machine. The HME machine is preheated to for example about 150° C. The HME machine snail speed is set to 100 rpm. As the melted material is drawn from the HME machine, it is forwarded as strands onto a cooling machine to cool on a conveyor belt. Once cooled, the strand is chopped by a chopping machine to pin shape of about 1.5 mm diameter and 2 mm length. The pins are then placed in a coating system (e.g., vector coater) and coated with Eudragit® E PO coating with a total of for example about 10% of weight gain.

In some embodiments, at least one of the support elements 42, 44 is configured to be disabled after the device is exposed to standard ICV environmental conditions for a predetermined time period and at least one of the support elements 42, 44 is configured to be disabled after the device is exposed to a predetermined set of activation environmental conditions, for example a surrounding pH reaching below pH 5.

The support elements 42, 44 may be arranged to form keystones of the device in the trapping configuration so as to provoke a collapse of the device into the emptying configuration after the device is exposed to the predetermined activation signal. In other words, the support elements 42, 44 are arranged to form one or more structural weak points. When the support elements 42, 44 are disabled, the one or more structural weak points cause the device to fall apart in the emptying configuration. The support elements 42, 44 are arranged so that a transfer duration of the device from the trapping configuration into the emptying configuration is substantially smaller (e.g., equal or less than ½, ⅓, ¼, ⅕, ⅙, ⅐, ⅛, ⅑, ⅒, ¹⁄₁₀₀, ¹⁄₁₀₀₀) than a standard residence time period (e.g., equal or more than 1, 2, 3, 4, 5, 6, 7 or 8 weeks). This provides an improved control of the device in in-vivo conditions. In particular, in embodiments in which the trigger assembly is activated by external means, this enables to quickly empty the device on-demand without requiring a colonoscopy procedure even in urgent cases.

In the trapping configuration, the device 100 may have substantially an ovoid or spherical shape. A diameter of the device in the trapping configuration may be of about 15 mm to 35 mm, preferably of about 20 to 30 mm, or of about 25 to 30 mm. In the closed configuration, the device 100 may have substantially an elongated shape. A length of the device 100 may be of about 10 mm to 45 mm, preferably of about 30 mm. A diameter of the device 100 in the closed configuration may be of about 5-15 mm, preferably of about 9-12 mm.

The device 100 may further comprise a locking element (not shown) arranged to temporary maintain the device in the closed configuration to facilitate oral administration. The locking element may be configured to temporarily overcome the biasing assembly 30. The locking element may be configured to release the device in the small intestine into the trapping configuration. In some embodiments, the locking element may be at least partially made of a material dissolving at small intestine environmental conditions while not dissolving at standard stomach environmental conditions. For example, the locking element may be at least partially made of an enteric polymer. In some embodiments, the locking element may be a container (e.g., a capsule) made of an enteric polymer.

In some embodiments, the device may include a labelling element enabling detection by external detection means. For example, the device may include a barium (or a metal) labelling element which can be detected by detection methods like X-ray imaging.

The device 100 may be configured to transit from the small intestine until the ICV in the trapping configuration without damaging the patient tissue. The device 100 may have an external envelope configured to contact the patient tissue. In particular, the device 100 may be flexible to avoid damaging the patient tissue. The external envelope of the device 100 may be blunt (unsharpened). A maximum diameter of the device in the trapping configuration may be below about 35 mm and preferably below about 30 mm.

The device may operate according to the general operation described below. As explained, the device in the closed configuration may be temporarily maintained in the closed configuration by an enteric coated capsule as locking element. Following oral administration, the enteric coated capsule may dissolve in the small intestine thereby releasing the device into the trapping configuration. The device in the trapping configuration may transit to the ICV region due to GI motility and position itself at the ICV. Alternatively, the device may be positioned in the trapping configuration at the ICV by upper/lower endoscopy. Once positioned at the ICV of the patient, the device described herein may be used in cooperation with a cooperating object in the form of an oral dosage form. An oral dosage form for cooperation with the device may have dimensions so as to enable trapping by the device when reaching the ICV after oral administration. The dosage form (e.g., a tablet) may comprise a therapeutic payload (i.e., an active pharmaceutical ingredient (API)) for local release and/or topical treatment of a patient condition at the ICV region. The dosage form may advantageously comprise a protective cover (e.g., a coating) so as to remain functional (and optionally substantially intact) until it reaches the ICV region. For example, the dosage form may have a protective cover such that less than a predetermined ratio of the API (e.g., less than 10%, 20%, 30%, 40%) is released prior to reaching the ICV.

Following oral administration, the cooperating dosage form transits along the GI until reaching the ICV region where it is trapped by the trapping assembly of the device. At the ICV, the API is then released from the cooperating dosage form for a predetermined time. The release of the API progressively downsizes the cooperating dosage form until it passes through the trapping assembly of the device. Subsequent cooperating dosage forms can be administered similarly. The device enables frequent administration of a cooperating oral dosage form while lowering the risk of obstruction and enabling tissue relaxation. For example, the cooperating dosage form may be daily administered for a period of 2-8 weeks for example for treating UC.

Once positioned, in some embodiments, the device may also be used in cooperation with a cooperating object in the form of an emptying dosage form that is configured to cause transfer of the device into the emptying configuration (i.e., to activate the trigger assembly 40). In some embodiments, as described above, the trigger assembly may be activated by the device being exposed to a predetermined set of activation environmental conditions. The emptying dosage form may be configured to cause the ICV environmental conditions to reach the activation environmental conditions. Basically, in these embodiments, an emptying dosage form for cooperation with the device may have external dimensions enabling the emptying dosage form to be blocked by the trapping assembly of the device when reaching the ICV after oral administration and may comprise a payload (in the form of an emptying agent) enabling to cause the environmental conditions of the ICV to reach the predetermined set of activation environmental conditions. For example, the trigger assembly may be activated when a surrounding pH reaches below a predetermined threshold (e.g., pH 5) and the emptying dosage form may be configured with an acidic payload. Advantageously, the emptying dosage form may comprise a protective cover (e.g., a coating) for enabling the emptying dosage form to remain functional (and optionally remain substantially intact) until it reaches the ICV.

Following oral administration, the cooperating emptying dosage form transits along the GI until reaching the ICV where it is trapped. At the ICV, the payload of the emptying dosage form is released so as to cause the trigger assembly of the device to activate thereby causing transfer of the device into the emptying configuration.

With reference to FIGS. 3A-3B and 4A-4B, more details regarding an arrangement of the biasing assembly 30 and the trigger assembly 40 of the device shown in FIG. 1 are provided.

The biasing assembly 30 may comprise two coupling hooks 32, 34 and an elastic member 35. The coupling hooks 32, 34 may each be arranged to sit on the four flexible arm 11-14 ends. The elastic member 35 may be arranged between the arms 11-14 and configured to force the coupling hooks 32, 34 together thereby bending the arms 11-14 into the trapping configuration. In other words, each of the coupling hooks 32, 34 may be configured to hook respectively four flexible arms ends and the elastic member 35 may be configured to pull the coupling hooks 32, 34 together to bend the arms into a rounded shape.

The elastic member 35 may be releasably secured to the coupling hooks 32, 34 by the support elements 42, 44 of the trigger assembly 40. In some embodiments, the support elements 42, 44 are erodible elements configured to degrade when the device is exposed to an activation signal, and the erosion of the support elements releases the arm coupling hooks 32, 34 from the elastic member 35 so that the device irreversibly returns into the closed configuration in which it may be capable of being emptied through the ICV. The elastic member 35 may comprise extension straps 352, 354. The extension straps 352, 354 may or not be unitary with the elastic member 35.

For the sake of conciseness, a detailed description of the arrangement of support element and coupling hook is given only for one of the two coupling hook 32, 34, support elements 42, 44 and extension straps 352, 354. It is understood that a similar arrangement may be foreseen for the other coupling hook 34, support element 44 and extension strap 354. The coupling hook 32 may include a hollow shank 321 and a head 323 forming a circumferential ledge at an upper end of the hollow shank 321. The hollow shank 321 may be positioned concentric to the four arms 11-14. The circumferential ledge of the head 323 may be seated on the arm 11-14 ends. A lower end of the shank 321 may comprise an inner plate 325 protruding radially from an inner surface of the shank 321. The inner plate 325 may include a through opening 327 which can be formed as a slot. The shank 321 may further comprise one or more piercing holes 326 configured to enable liquid entering the hollow shank 321. The support element 42 may be supported on the inner plate of the coupling hook 32. The extension strap 352 may form a loop passing through the opening 327 in the inner plate 325 of the shank 321 and wrapping around the support element 42 thereby securing between the coupling hook 32 and the elastic member 35.

Figure 5B:
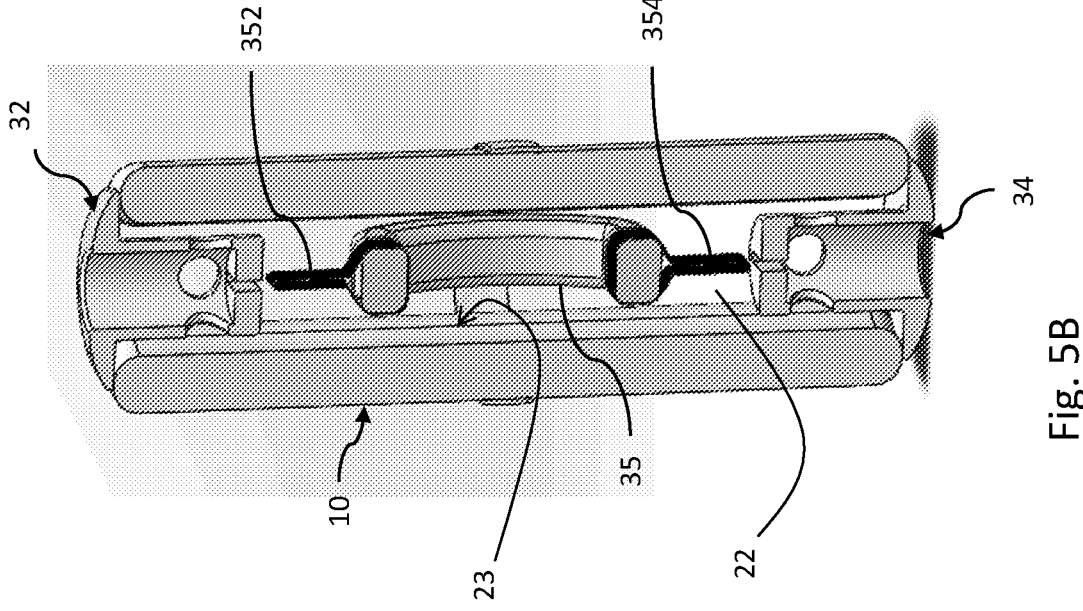
FIGS. 5A-5B show a perspective view and a cross section view of the device of FIG. 1 in an emptying configuration.
Figure 5A:
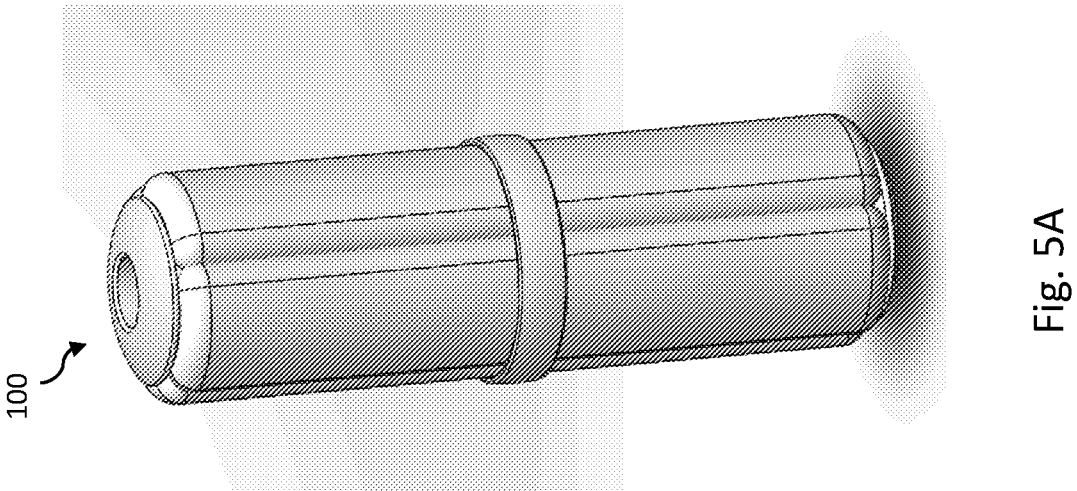

FIGS. 5A-5B illustrate the device shown in FIG. 1 but in the emptying configuration. As can be seen, the emptying configuration can resemble the closed configuration. In some embodiments, the emptying configuration can even be identical to the closed configuration. As shown in FIG. 5A, an external envelope of the device in the emptying configuration may be identical to an external envelope of the device in the closed configuration. However, as shown in FIG. 5B, the elastic member 35 is in a relaxed state and the extension straps 352 and 354 are free. The support elements 42, 44 have degraded and are not visible on FIG. 5B since the emptying configuration follows activation of the trigger assembly.

An assembly method of a device 100 as shown on FIG. 1 is now described. In a first step, a silicone high shore (80 A) tube having 30 mm length and 8 mm external diameter and 3 mm internal diameter is cut symmetrically with four central longitudinal slits of 26 mm leaving about 2 mm of each side not cut. This provides the four flexible arms 11-14 coupled to each other at both end by a top and a bottom coupling portion. Then, in a second step, a circular string ring made of elastic shore 40 A silicone string having 0.7 mm thickness and 1.2 mm width and diameter of 10 mm is connected on the four arms of the tube at a longitudinal middle portion of the four arms. This provides for the circumferential belt 15. Connecting of the circular string to the arms can be done with silicone glue. The thickness, width and arrangement of the circumferential belt 15 and flexible arms 11-14 result in a meshwork having eight openings 20. The eight openings 20 may have a surface area of about 24.8 mm$^2$ each when the trapping device is in the trapping configuration using the biasing assembly described hereinbelow.

The coupling hooks 32, 34 are made of aluminum. An external diameter of the circumferential ledge of head 323 may be of about 8 mm. An internal diameter of the shank 321 is of about 3.5 mm. The elastic member 35 is made of an elastic band ring of 6 mm external, 4 mm internal diameter having 1 mm thickness, 3 mm width made of silicone shore 50 A. In a third step, the elastic member 35 is fixed at two diametrically opposed points to extension straps 352, 354 made of a non-ductile material. The extension strap 352, 354 are then pulled through the openings 327 in the inner plates 325 of the shanks 321 of the coupling hook 42, 44. Eudragit E pins of 1.6 mm diameter and 2.5 mm length as support elements 42, 44 are then sandwiched between the extension straps 352, 354 and the openings 327 in such a way that upon erosion of the pins 42, 44, the extension straps 352, 354 freely detach from the coupling hooks 32, 34. This provides the device in the unfolded configuration. Such four-arm spherical trapping device in the folded configuration has dimensions enabling efficient encapsulation into a 31 mm length and 11 mm diameter capsule. Based on this principle, various alternative spherical shapes could be made, e.g., having different number of arms, arm length, materials composition (e.g., corners made of hard polymer such as polyurethane) enabling for example to tune up the device dimensions and mechanical properties to meet different targets (for example specific human population or for veterinary purposes. For example a device made of six arms having a length of 33 mm and a circumferential belt of 1 mm width will result in meshwork having 12 holes, that can be encapsulated into a 35 mm by 11 mm capsule. Each hole may have an external surface area of about 26.7 mm$^2$ each.

Optionally, the device 100 may carry a load of an API, and the device 100 may be configured for releasing at least partially the API while allowing chyme flow, when the device is positioned at the ileocecal valve and in the trapping configuration.

The load may be solid and/or further contain one or more pharmaceutically acceptable excipients. The solid load may comprise a therapeutic payload of the API for local release and/or topical treatment of a patient condition at the ICV region or for systemic absorption. The API may be any one of the APIs mentioned earlier, and/or for the treatment of any disease or medical condition mentioned earlier. The API may be the same API as the one in the cooperating therapeutic oral dosage from (e.g., in the same or in a different dosage), or a different API. The solid load may comprise no protective cover (e.g., a coating), as the device may comprise a locking container for delivery at the ICV, thereby ensuring that the load remains functional (and optionally substantially intact) until it reaches the ICV region. Alternatively, the solid load may have a coating, so as to release the API only when desired. In variations, the API may be carried by the device in a semi-solid or gel form, or in (any combination of) a solid, semi-solid, powder, gel, and/or liquid form (i.e., partly in one form, and partly in one or more other forms).

For example, the device 100 may comprise an inner space 22 in the closed configuration formed between the arms 11-14 and the elastic member 35 (see FIG. 5B), and the inner space 22 may contain a load of an API. Alternatively of additionally, the device 100 may comprise a coating on the inner surfaces 23 of the arms 11-14 (see FIGS. 2A and 5B), and the coating may contain a load of an API. Optionally, the device 100 may comprise a support tube (not shown), and the elastic member 35 may be arranged inside the support tube. The support tube may be as later described with reference to FIGS. 8A-8) and/or FIGS. 11A-11G, and notably (further optionally) carry a load of an API inside or thereon. When the device 100 expands from the closed configuration of FIG. 1B or 5A-5B into the trapping configuration of FIG. 1A or 2A-2B, the load is exposed to chyme flow through the openings 20 and thereby releases the API.

Figures 6A, 6B, 7:
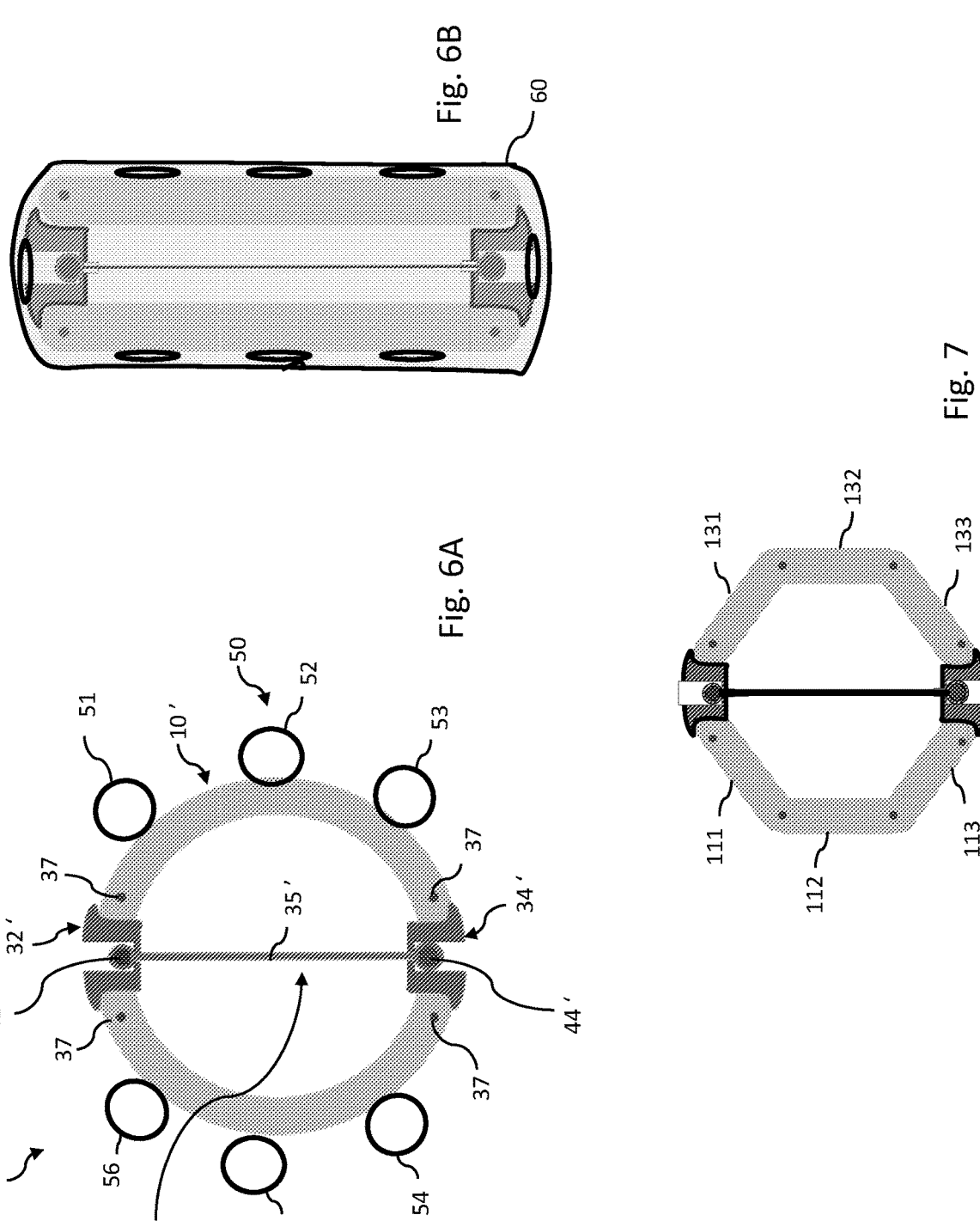
FIGS. 6A-6B show cross section views of another example of a device according to embodiments of the present disclosure.
FIG. 7 shows a cross section view of another example of a device according to embodiments of the present disclosure.

FIGS. 6A and 6B show another example of a device 100' for temporary ICV retention according to the present disclosure respectively in an open configuration and in a closed configuration.

The device 100' resembles the device 100 discussed above in many aspects. Accordingly, numerals used to identify features of the device 100 are appended a single quotation mark ' to identify like features of the device 100'. It is understood that the features which are similar to device 100 and combinable with device 100' are not all repeated in details below.

The device 100' may comprise a body 10', a biasing assembly 30', a trigger assembly 40' and optionally a padding assembly 50.

The body 10' may comprise several (e.g., four) flexible arms and a circumferential belt (not shown) disposed around the flexible arms. The circumferential belt 15 may be flexible to allow the flexible arms to bend into the trapping configuration without substantial restriction. For example, the circumferential belt 15 may be made of an elastic material. In the open configuration, the body defines openings which enable trapping of cooperating objects while allowing chyme flow when the device is positioned at the ICV. As shown on FIG. 7, one or more of the flexible arms may also be composed of a set of rigid arm sections 111-113,

131-133. The set of rigid arm sections may be coupled end to end so that the arm shape can vary. For example, the rigid arm sections 111-113, 131-133 may be coupled end to end with a pivot-type coupling.

The biasing assembly 30' may be configured to resiliently hold (bias) the device 100' in the trapping configuration. In other words, the biasing assembly 30' may be configured to cause the device to tend to resiliently return from the closed configuration into the trapping configuration. The biasing assembly 30' may comprise an elastic member 35' and coupling hooks 32', 34'. A first end of each flexible arm may be coupled to the first coupling hooks 32' and a second hand of each flexible arm may be coupled to the second coupling hook 34'. The coupling hooks 32', 34' may each be arranged to sit on the four flexible arm ends. Optionally, the arm ends and the coupling hooks may be coupled by pivot pins 37 thereby forming hinged connections between the arm ends and the coupling hooks. The elastic member 35' may be arranged between the arms and configured to force the coupling hooks 32', 34' together thereby biasing the device in the trapping configuration.

The elastic member 35' may be releasably secured to the coupling hooks 32', 34' by the support elements 42', 44' of the trigger assembly 40'. The elastic member 35' may be configured to be irreversibly released from the coupling hooks 32', 34' when the device 100' is exposed to an activation signal, so that the device irreversibly returns into the closed configuration in which it may be capable of being emptied through the ICV.

The padding assembly 50 may comprise a plurality of pads 51-56. The pads 51-56 may be disposed around the device 100'. The pads 51-56 may be made of a resilient material so as to be reversibly compressible. The pads 51-56 may be shaped as circles and/or as hollow cylinders. For example, the pads 51-56 may be made of silicone. The padding assembly 50 may enable the device 100' in the open configuration to have an increased cross section area so as to facilitate trapping of cooperating objects while not compromising the capacity of the device 100' to fit into a capsule as shown in FIG. 6B. Further, the padding assembly may be configured for lowering pressure on the patient tissue when the device 100' is in the open configuration.

Figures 8A, 8B, 8C:
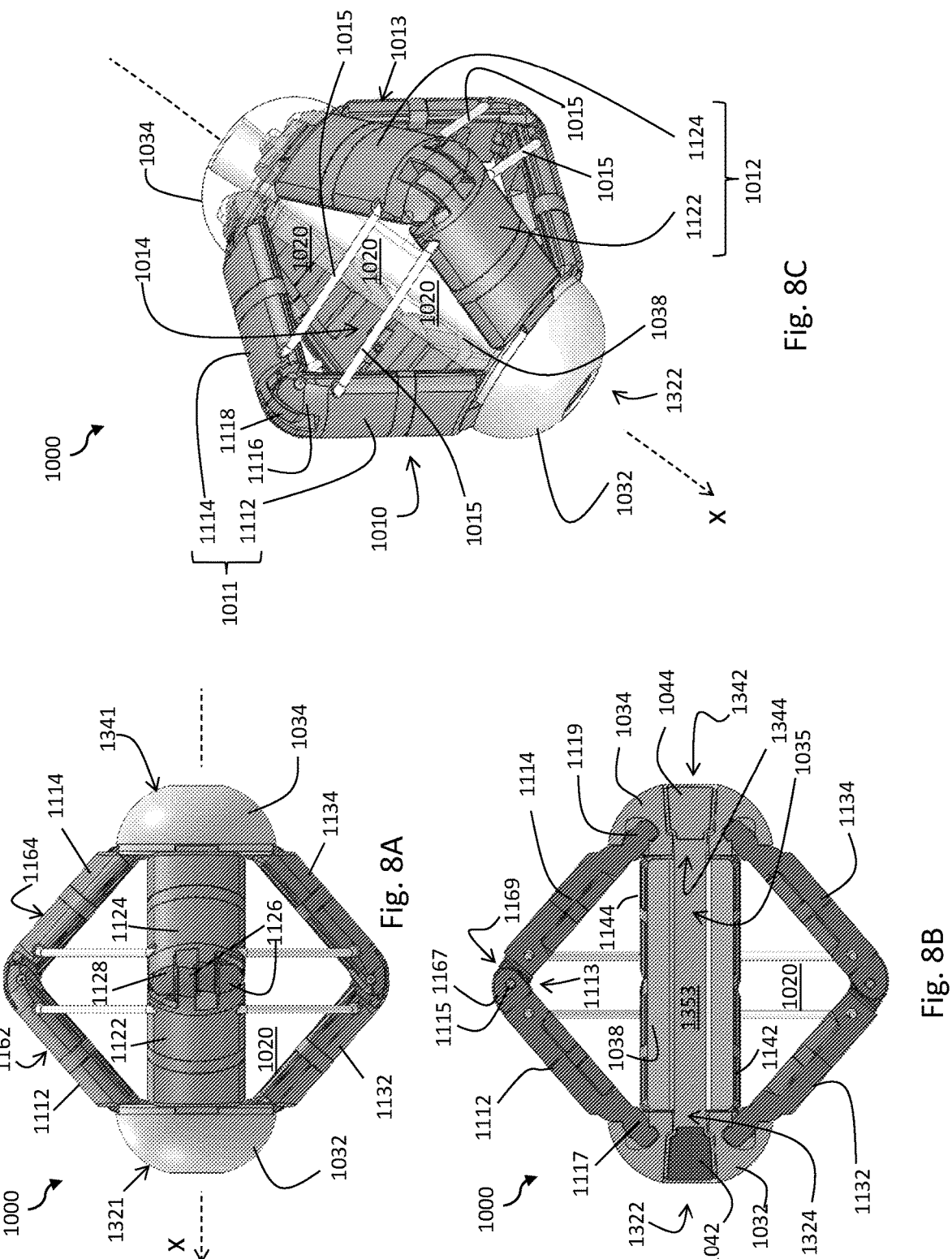
FIGS. 8A-8F illustrate another example of a device according to embodiments of the present disclosure.
Figures 8D, 8E, 8F:
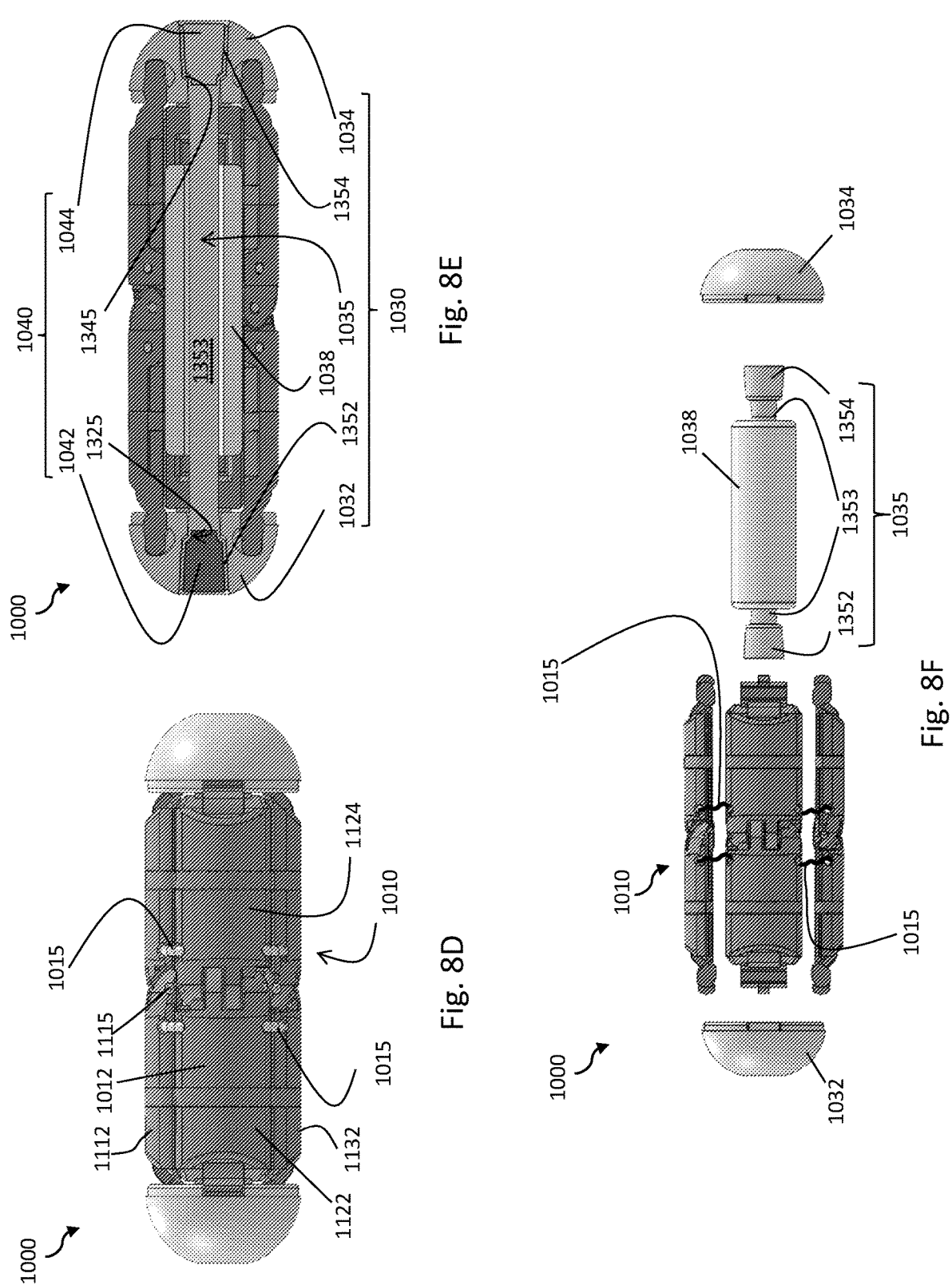

FIGS. 8A-8C, FIGS. 8D-8E, and FIG. 8F show another example of a device 1000 for temporary ICV retention according to the present disclosure, respectively in a trapping (open) configuration (FIGS. 8A-8C), in a closed (swallowing) configuration (FIGS. 8D-8E), and in a disassembled configuration which may form an emptying configuration and/or a pre-assembling configuration during manufacturing (FIG. 8F). FIGS. 8A, 8D, and 8F show a front view of the device 1000. FIG. 8C shows a perspective view of the device 1000 in the same configuration as in FIG. 8A. FIGS. 8B and 8E show a longitudinal cross-section view (along axis X) of the device 1000 in the same configuration respectively as in FIGS. 8A and 8D, the cross-section being taken in a median plane of the device 1000 parallel to the view plane of respectively FIGS. 8A and 8D.

The device 1000 resembles the device 100 discussed above in many aspects. Accordingly, numerals used to identify features of the device 100 are incremented by a factor 1000 to identify like features of the device 1000. It is understood that the features which are similar to device 100 and combinable with device 1000 are not all repeated in details below.

The device 1000 may be deformable from the closed configuration of FIGS. 8D-8E into the trapping configuration of FIGS. 8A-8C, and the device 1000 may be irreversibly disassembled from the trapping configuration of FIGS. 8A-8C into an emptying configuration identical or similar to the disassembled configuration of FIG. 8F.

The device 1000 may comprise at least three (e.g., four) articulated arms 1011-1014 arranged (e.g., longitudinally) alongside each other (e.g., along longitudinal axis X) and forming a body 1010 of the device (see FIG. 8C). An articulated arm is an elongated structure that includes at least one articulation between two sections or segments, allowing bending during which the two sections substantially maintain their shape. The articulated arms 1011-1014 may provide a high ratio of trapping volume (i.e., drug loading capacity between the arms) relative to compactness of the closed configuration (e.g., easiness of swallowing), while maintaining trapping capacity (i.e., capability of the device to retain objects of a certain size).

Each articulated arm may be composed of a set of (e.g., two) (e.g., rigid) arm sections. For example, the articulated arm 1011 may be composed of a first arm section 1112 and a second arm section 1114, the articulated arm 1012 may be composed of a first arm section 1122 and a second arm section 1124, the articulated arm 1013 may be composed of a first arm section 1132 and a second arm section 1134, and the articulated arm 1014 may be composed of a first arm section 1142 and a second rigid section 1144.

Each arm section 1112, 1114, 1122, 1124, 1132, 1134, 1142, 1144 may comprise one or more (e.g., one or two) integrally formed components. Each such integrally formed component may be rigid, meaning that is has no or low resilience (in particular, a substantially zero resilience or a resilience significantly lower than the resilience of the resiliently deformable member 1035). Each integrally formed component may be made of any rigid material, such as plastic (e.g., a resin), metal, or ceramic. Each integrally formed component may be 3D printed or (e.g., injection) molded. This facilitates manufacturing. Each integrally formed component may be made of a biocompatible material. The biocompatible material may optionally be biodegradable, and further optionally be configured for being retained at the ICV for a predetermined time and for a partial or complete erosion/softening before emptying from the body. For example, each integrally formed component may be made of MEDIC® rigid material manufactured by Stratasys® 3D printer or for example made of cellulose acetate manufactured by molding. The rigidity of the articulated arms may provide high structural rigidity and retention capability of the device (capacity of the device to be retained at the ICV), while maintaining trapping capacity and achieving a particularly high ratio of trapping volume relative to compactness of the closed configuration, thanks to allowed thinness of the arms. In variations, each arm section may be semi-rigid or made in a flexible material (e.g., silicone). In yet other variations, each arm section may comprise any combination of one or more rigid components, one or more semi-rigid components, and/or one or more flexible components. In further variations, the arm sections may be made in different materials one from another.

Each articulated arm 1011-1014 may have a first end (e.g., 1117) and a second end (e.g., 1119). The first end 1117 and the second end 1119 of articulated arm 1011 only are given a numeral reference on the figures (see FIG. 8B), for the sake of conciseness. Each first end (e.g., 1117) may be an end of the first arm section (e.g., 1112) of the articulated arm (e.g., 1011), while each second end (e.g., 1119) may be an end of the second arm section (e.g., 1114) of the articulated arm (e.g., 1011).

The device 1000 may comprise a first coupling head 1032 and a second coupling head 1034. The first and second coupling heads 1032 and 1034 may be substantially identical, each substantially centered on longitudinal axis X, and/or arranged substantially symmetrically one relative to another with respect to a median plane (not shown) of the device 1000 substantially perpendicular to axis X.

Each coupling head may be integrally formed and/or made of any material (identical to or different from the arm sections), for example a rigid material, such as plastic (e.g., a resin), metal, or ceramic, or a semi-rigid or flexible material. Each coupling head component may be 3D printed or (e.g., injection) molded. This facilitates manufacturing. Each coupling head may be made of a biocompatible material. The biocompatible material may optionally be biodegradable, and further optionally be configured for being retained at the ICV for a predetermined time and for a partial or complete erosion/softening before emptying from the body. For example, each coupling head may be made of MEDIC® rigid material manufactured by Stratasys® 3D printer or for example made of cellulose acetate manufactured by molding. The rigidity of the coupling heads may provide high structural rigidity of the device.

In the trapping configuration (see FIGS. 8A-8C), the first end (e.g., 1117) of each articulated arm (e.g., 1011) is coupled to (i.e., connected to, cooperating with) the first coupling head 1032, and the second end (e.g., 1119) of each articulated arm (e.g., 1011) is coupled to the second coupling head 1034. Thus, the first and second coupling heads 1032 and 1034 are configured to join the (e.g., four) articulated arms 1011-1014 to each other by both ends, such that the arms 1011-1014 are secured alongside each other in the trapping configuration.

In the closed configuration (see FIGS. 8D-8E), the first end (e.g., 1117) of each articulated arm (e.g., 1011) may also be coupled to the first coupling head 1032, and the second end (e.g., 1119) of each articulated arm (e.g., 1011) may be coupled to the second coupling head 1034. Thus, the arms 1011-1014 are secured alongside each other in the closed configuration as well.

The first end (e.g., 1117) of each articulated arm (e.g., 1011) may be rotatably coupled to the first coupling head 1032, and the second end (e.g., 1119) of each articulated arm (e.g., 1011) may be rotatably coupled to the second coupling head 1034. In other words, each articulated arm 1011-1014 may be connected to the first coupling head 1032 and/or to the second coupling head 1034 but with freedom in rotation relative thereto.

The respective arm sections 1112 and 1114, 1122 and 1124, 1132 and 1134, and 1142 and 1144 of each articulated arm 1011-1014 may further be coupled end to end with a pivot-type coupling (e.g., 1113). For each articulated arm (e.g., 1011) consisting of two arm sections (e.g., 1112 and 1114), each arm section may be coupled (e.g., rotatably) at one end to the first or second coupling head 1032 or 1034 and coupled (e.g., rotatably) at the other end to the other arm section. For example, the first arm section 1112 of the articulated arm 1011 is coupled (e.g., rotatably) at its one end 1117 (i.e., first end of the articulated arm 1011) to the first coupling head 1032 and at its other end 1167 to the other (i.e., second) arm section 1114 of the articulated arm 1011 with a pivot-type coupling 1113. Similarly, the second arm section 1114 of the articulated arm 1011 is coupled (e.g., rotatably) at its one end 1119 (i.e., second end of the articulated arm 1011) to the second coupling head 1034 and at its other end 1169 to the other (i.e., first) arm section 1112 of the articulated arm 1011 with the pivot-type coupling 1113. The pivot-type coupling 1113 of the articulated arm 1011 only is given a numeral reference on the figures (see FIG. 8B), for the sake of conciseness.

The device 1000 may thus form a (e.g., rigid) mobile (e.g., Sarrus) mechanism deformable from the closed configuration of FIGS. 8D-8E into the expanded configuration of FIGS. 8A-8C, optionally reversibly deformable between from the trapping configuration of FIGS. 8A-8C into the closed configuration of FIGS. 8D-8E, by converting relative rotations into a relative motion (e.g., a translation along axis X) between the first coupling head 1032 and the second coupling head 1034. The converted relative rotations are the relative rotation of each pair of coupled arm sections one with respect to the other, and the relative rotation of each arm section coupled to a coupling head 1032 or 1034 with respect to said head. Such motion conversion achieves bending (e.g., respectively, straightening) of the articulated arms to (e.g., reversibly) deform the device from (e.g., respectively, into) the closed configuration into (e.g., respectively, from) the expanded configuration. Indeed, the articulated arms are bent in the expanded configuration (see FIGS. 8A-8C), whereas the articulated arms are substantially straight in the closed configuration (see FIGS. 8D-8E). In examples, due to their rigidity, the rigid arm sections 1112, 1114, 1122, 1124, 1132, 1134, 1142, 1144 maintain their shape during the whole motion conversion, and thereby each present a substantially identical shape between the trapping configuration and the closed configuration. In other words, no rigid arm section is deformed during its relative rotation with another component.

The articulated arms 1011-1014 may be structurally identical one to another. The device 1000 may present a symmetry of revolution with respect to axis X. The arm sections 1112, 1114, 1122, 1124, 1132, 1134, 1142, 1144 may be arranged in one or more (e.g., two) layers between the coupled heads 1032 and 1034. When each articulated arm consists of two arm sections, the first arm sections 1112, 1122, 1132, 1142 may form a first layer while the second arm sections 1114, 1124, 1134, 1144 may form a second layer. The two layers may be separated by the median plane (not shown) of the device 1000 substantially perpendicular to axis X. In other words, pivot-type couplings (e.g., 1113) between the first arm sections 1112, 1122, 1132, 1142 and the second arm sections 1114, 1124, 1134, 1144 may all lie on said plane. The device 1000 may be symmetrical with respect to said median plane.

Each arm section 1112, 1114, 1122, 1124, 1132, 1134, 1142, 1144 may be of a generally prism shape (i.e., generally straight). The device 1000 may itself be of a generally prism (e.g., cylindrical) shape in the closed configuration (see FIG. 8D). Each arm section 1112, 1114, 1122, 1124, 1132, 1134, 1142, 1144 may maintain its shape (i.e., not be deformed) during use of the device 1000, for example during transfer from the closed configuration into the trapping configuration, and/or during transfer from the trapping configuration into the emptying configuration.

Each arm section 1112, 1114, 1122, 1124, 1132, 1134, 1142, 1144 may be substantially of a same length, optionally structurally identical. The device may thus have a generally (e.g., regular) bipyramidal shape in the trapping configuration, preferably a generally (e.g., regular) octahedral shape (i.e., when, the number of articulated arms 1011-1014 is exactly four). Each arm section may correspond to an edge of the bipyramidal shape, while each pivot-type coupling (e.g., 1113) and each coupling head 1032 and 1034 may correspond to a vertex of the bipyramidal shape. The device 1000 is thus configured to (e.g., reversibly) switch the generally compact prism/straightened shape of the closed configuration (with a relatively small volume occupancy) into the generally hollow bipyramidal shape of the expanded configuration (with a relatively large volume occupancy). Components of the device 1000 may be rounded at edges and/or vertices of the bipyramidal (e.g., octahedral) shape, such that the device 1000 may present in the (unfolded) trapping configuration a generally spherical convex hull 3D structure.

The rigidity of the articulated arms 1011-1014 allows the device 1000 to present a relatively high structural rigidity while making it easy to achieve an optimize use of space. In particular, a 3D structure with a high sphericity (e.g., above 0.8, e.g., measured by the Hakon Wadell sphericity equation of the convex hull of an object) and/or a low ratio between a maximal circumference and a minimal circumference (e.g., below 1.5, e.g., each circumference being the length of a planar curve traced on a periphery of an object) allows a high retention at the ICV, while enabling optimal tissue pressure distribution, e.g., when device is in the trapping configuration, and small size when in closed configuration to enable swallowing.

In examples, the volume occupied by the device in the trapping configuration may be larger than a sphere of a diameter of 17 mm, and optionally larger than a sphere of a diameter of 20 mm. In examples, the assembly consisting of the articulated arms 1011-1014 and the coupling heads 1032, 1034 in the closed configuration may present dimensions (also referred to as "folded dimensions" or "dimensions of the device when folded" or the like), such that it may be capable of being fitted into a cylinder of less than about 35 mm and of less than about 12 mm diameter. In particular, said assembly in the closed configuration may be capable of being fitted into a cylinder of length less than 32 mm, 31 mm, 30 mm, or 29 mm, and/or of diameter equal to or less than 11 mm, 10.5 mm or 10.2 mm, for example a cylinder of length less than 29 mm and/or of diameter less than 10.2 mm, such as a cylinder of length equal to 28.8 mm and a diameter equal to 9.8 mm.

Thus, an optional (e.g., particularly easy to swallow) container (resistant to standard gastric environmental conditions and configured to degrade in small intestine environmental conditions, e.g., at least partially made of an enteric polymer, not shown on the figures) configured to temporarily at least partially enclose the device in the closed configuration (e.g., a capsule), may present a length of about 35 mm or less and/or of diameter of about 12 mm or less, for example a length equal to or less than 32 mm, 30 mm or 29 mm and/or a diameter equal to or less than 11, 10.5 mm or 10.2 mm, such as length equal to 29 mm and a diameter equal to 10.2 mm.

Such a container may form a locking element and/or be resistant to standard gastric environmental conditions and configured to degrade in small intestine environmental conditions (e.g., the container is at least partially coated with or made of an enteric polymer). In variations, the container may merely form a capsule to enable swallowing, and/or the device may comprise another and separate component forming such a locking element arranged to temporary maintain the device in the closed configuration for facilitating administration and/or at least partially made of a material degrading at standard small intestine environmental conditions and resistant at standard stomach environmental conditions (e.g., the locking element is at least partially coated with or made of an enteric polymer).

Yet, even with such dimensioning, the device 1000 may present appropriate trapping capabilities. For example, the device in the trapping configuration may be configured to block cylindrical or other commonly shaped tablet dosage forms. Particularly, the device in the trapping configuration may be configured to block spherical beads of a diameter larger than a trapping threshold diameter of e.g., 7 mm, 8 mm, 9 mm, 10 mm, 11 mm or 12 mm. In the following, the predetermined dimensions of the ingested objects may refer to the dimensions of said ingested objects when reaching the ileocecal valve region i.e., after transit through the GI tract. In some embodiments, the capability of the device 1000 to block cooperating objects (such as dosage forms with specific dimensions when reaching the ileocecal valve region after GI transit) while allowing chyme flow may be defined in accordance with methods described in details herein below with reference to FIGS. 12 and 13. In some embodiments, the device 1000 may be configured so as to allow passage of spherical beads of a diameter lower than a passage threshold diameter of e.g., 3 mm, 4 mm, 5 mm or 6 mm. In some embodiments, the frame of the device is configured to form the trapping assembly.

Still, even with such dimensioning, the dimensions of the device in the trapping configuration may be such that the device cannot pass through an orifice of about 17 mm diameter and preferably of about 20 mm and even achieves high retention. Generally, the device 1000 may have a shape and/or a size and/or a structural rigidity enabling the device to be retained at the ileocecal valve. The capability of the device 1000 to be retained at the ICV may be defined in accordance with methods described in details herein below with reference to FIG. 12.

In embodiments, each pivot-type coupling (e.g., 1113) may comprise, for each pair of arm sections coupled end to end (by said pivot-type coupling), transversal hinge holes of the arm sections of the pair and a hinge pin passing through the transversal hinge holes. The hinge pin may be made of any rigid material, such as any plastic or any metal or any rigid biocompatible material. The hinge pin may be made, e.g., of nylon or Nitinol. The hinge pin may alternatively be made of an erodible polymer, so as to enable disassembly of the arms upon its erosion to facilitate emptying of the device after retention in the ICV. For example, the pivot-type coupling 1113 may comprise a hinge pin 1115 (see FIG. 8B) passing through both transversal hinge holes (no numeral reference) formed on the end 1167 of the first arm section 1112 and transversal hinge holes (no numeral reference either) formed on the end 1169 of the second arm section 1114. In examples, the end 1167 of the first arm section 1112 may comprise a first set of one or more (e.g., two) fingers 1126 and the end 1169 of the second arm section 1114 may comprise a second set of one or more (e.g., two) fingers 1128 (see FIGS. 8A and 8C). The fingers 1126 and 1128 may extend longitudinally from their respective arm sections and be dimensioned for the first and second sets of fingers to engage one with another, thereby reaching alignment of all the transversal hinge holes, thus allowing passage of the hinge pin 1115.

The device 1000 may comprise one or more (e.g., one or two) circumferential threads 1015 circumferentially linking the articulated arms (see FIGS. 8C, 8D and 8F). Each thread 1015 may be made of an elastic or a flexible material so as to allow the articulated arms 1011-1014 to open into the trapping configuration without substantial restriction. For example, each thread 1015 may be made of silicone or fabric, synthetic polymer such as nylon, polyurethane. Each thread 1015 may pass through transversal threading holes (no numeral reference) formed on the articulated arms. Each thread 1015 may be pulled through transversal threading holes and tied at the end. The transversal threading holes may comprise one or more (e.g., one or two) layers of transversal threading holes, each layer being on a respective plane perpendicular to axis X. For example, each first arm section 1112, 1122, 1132, 1142 may comprise a respective transversal threading hole forming together a first layer of transversal threading holes perpendicular to the axis X, and each second arm section 1114, 1124, 1134, 1144 may comprise a respective transversal threading hole forming together a second layer of transversal threading holes perpendicular to the axis X (thus parallel to the first layer of transversal threading holes). A same thread 1015 may be pulled through each respective layer of transversal threading holes and tied at the end. Optionally, a same unique thread may pass through the optional different layers, or alternatively one single thread may be pulled per layer. In variations, the device 1000 may comprise one or more (e.g., one) circumferential belts instead of, or in addition to, the one or more circumferential threads. In variations, a thread 1015 may be pulled through the hinge holes of the pivot-type couplings (e.g., 1113) and serve for both circumferentially linking together the articulated arms and as a hinge connector (i.e., for achieving the hinge mechanism of the pivot-type couplings). In other words, the thread serves as both a belt and in place of a hinge pin.

The body 1010 may form the frame of the device 1000. The device 1000 may be configured to bend the articulated arms 1011-1014 in an angular shape (in the trapping configuration). When not bent, the arms 1011-1014 may substantially extend in the direction of the longitudinal axis X. In the trapping configuration, the device 1000 is configured, when the device is positioned at the ileocecal valve, to be retained at the ileocecal valve of the subject, and to block a cooperating ingestible object while allowing chyme flow.

When the device 1000 is in the open (trapping) configuration, the body 1010 and the one or more (e.g., one or two) circumferential threads 1015 may form a tridimensional meshed structure. The openings 1020 formed between the articulated arms 1011-1014 and the circumferential threads 1015 in the open configuration may define a mesh of said meshed structure. The openings 1020 may be configured to enable trapping of cooperating objects. In other words, the device 1000 may be configured so that in the trapping configuration, the openings 1020 formed between the arms 1011-1014 and the circumferential threads 1015 are dimensioned so as to trap cooperating objects.

The circumferential threads 1015 may further have a structural function, for example stabilize the platform formed by the device 1000 in the expanded configuration. This improves ICV retention.

The device 1000 in the trapping configuration has an external envelope configured to contact the subject tissue (see FIG. 8A). The external envelope comprises the external surface 1321 of the first coupling head 1032, the external surface 1341 of the second coupling head 1034, and the external surface (e.g., 1162, 1164) of each articulated arm (e.g., 1011). The external surfaces 1162, 1164 of the first and second arm sections 1112, 1114 of articulated arm 1011 only are given a numeral reference on the figures, for the sake of conciseness. The external envelope of the device 1000 may be blunt to avoid damaging the subject tissue. In particular, the coupling heads 1032, 1034 may be made of a smooth material (e.g., plastic, such as resin, or polyurethane, or other biocompatible material) and/or of an externally smooth (e.g., rounded) shape, for example of a general shape of a section of a sphere or ovoid (e.g., semi-sphere or semi-ovoid). Also, the articulated arms 1011-1014 may be made of a smooth material (e.g., plastic, such as resin) and/or of an externally smooth shape, for example of a general shape of a longitudinal section of a cylinder or a prism having an elliptical base. In addition, the external surface (e.g., 1162, 1164) of the ends (e.g., 1167, 1169) of the arm section (e.g., 1112, 1114), for example the external surface of the fingers 1126 and 1128, may be longitudinally rounded. Thus, even when they are bent, the articulated arms 1011 present a smooth vertex at the pivot-type coupling region between the arm sections, to avoid damaging tissue.

The device 1000 may further comprise a resiliently deformable (biasing) member 1035 arranged between the articulated arms 1011-1014 and configured to force the coupling heads 1032 and 1034 together to bend the arms thereby biasing the device in the trapping configuration. Thus, the coupling heads 1032 and 1034 come close one to another in the trapping configuration thanks to retraction of the resiliently deformable member 1035 (i.e., the coupling heads 1032 and 1034 are closer one to another in the trapping configuration than in the closed configuration). The resiliently deformable member 1035 may further be arranged inside an optional support tube 1038. The coupling heads 1032 and 1034 may thus form, with the resiliently deformable member 1035 and with the optional support tube 1038, a biasing assembly 1030 configured to resiliently hold (bias) the device 100 in the trapping configuration. In other words, the biasing assembly 30 may be configured to cause the device to tend to resiliently return (unfold) from the closed configuration into the trapping configuration.

The resiliently deformable member 1035 may be configured to be stretched (along longitudinal axis X, into the closed configuration). For example, the resiliently deformable member 1035 may be elastic (i.e., made of an elastic material, such as silicone). For example, the resiliently deformable member 1035 may be made of silicone shore 55 A, for example as a section of a silicone tube having a cross section area of about 3 mm². In variations, the resiliently deformable member may be a spring, for example made of metal (such as stainless steel or Nitinol).

The resiliently deformable member 1035 may be secured to both the first and second coupling heads 1032 and 1034. The resiliently deformable member 1035 may comprise a first extension 1352 and a second extension 1354 at its extremities (i.e., edges), and a central resiliently deformable portion 1353 therebetween (see FIG. 8F). The first extension 1352 may be secured to the first coupling heads 1032, and the second extension 1354 may be secured to the second coupling heads 1034. The first and second extensions 1352, 1354 may or not be unitary with the central resiliently deformable portion 1353. In the latter case, the central resiliently deformable portion 1353 may be secured at its two extremities to the first and second extensions 1352, 1354. The first and second extensions 1352, 1354 may or not be resiliently deformable. The first and second extensions 1352, 1354 may form extension straps.

The first coupling head 1032 may comprise a first longitudinal hollow portion formed along axis X between a first external opening 1322 and a first base opening 1324, and/or the second coupling head 1034 may comprise a second longitudinal hollow portion formed along axis X between a second external opening 1342 and a second base opening 1344 (see FIG. 8B). The resiliently deformable member 1035 may be configured to have the first and second extensions 1352 and 1354 inserted and secured into the first and second hollow portions, for example by the first and second extensions 1352 and 1354 being pulled through the first and second base opening 1324 and 1344 and then secured in the first and second hollow portions.

The resiliently deformable member 1035 may be secured to at least one (e.g., only one, or alternatively, both) of the first and second coupling heads 1032 and 1034 releasably. When the resiliently deformable member 1035 is released from the first coupling head 1032 and/or from the first coupling head 1034, the resiliently deformable member 1035 stops to force the coupling heads together 1032 and 1034. Thus, the resiliently deformable member 1035 stops forcing the bending of the articulated arms 1011-1014. This causes transfer from the trapping configuration into an emptying configuration, the device being thereby configured to pass through the ileocecal valve.

The support tube 1038 may be a hollow tube made of any material, such as a rigid material (e.g., plastic, metal, ceramic) or an elastic material. The surrounding intestinal tissue (e.g., in ICV) may press (compress) the device 1000. Such pressure when applied from the X-axis on the external surface of head 1032 and head 1034 inwards might move the two heads towards each other. A significant movement would result in deformation of the device's structure and even collapse. The support tube 1038 may resist this collapse and maintain the device unfolded and maintains the structural dimensions of the device in the trapping configuration, thus a high retention force of the device (also referred to as "emptying force"), thus allowing a safe retention of the device at the ICV. When made of material having elastic properties, the support tube 1038 may have a safety shock absorption element enabling partial limited movement of the heads towards each other. This enables the device to be compliant with the tissue, e.g., when high pressure applied by tissue, e.g., in abnormal conditions. The support tube 1038 may be made for example of silicone shore 55 A, for example as a section of a silicone tube having an external diameter of about 4 mm and an internal diameter of about 2 mm. The support tube 1038 may present a length corresponding to that of a maximal authorized diameter for the device 1000 in the trapping configuration. The support tube 1038 thus allows maintaining a minimal distance (corresponding to the length of the support tube 1038) between the two coupling heads 1032 and 1034, thereby preventing the device 1000 from expanding beyond the maximal authorized diameter (e.g., in the Y axis when pressure is applied from the X axis on the two coupling heads). This improves safety of the device 1000, by reducing risks of tissue damage.

The device 1000 may comprise a trigger assembly 1040 (see FIG. 8E), forming an opening assembly with the biasing assembly 1030. The trigger assembly 1040 may be configured, when the device in the trapping configuration is exposed to any respective activation signal from a predetermined set of one or more activation signals, to trigger release of the resiliently deformable member 1035 from the first and/or second coupling heads 1032, 1034. The device 1000 may be configured to transfer into an emptying configuration in which it can pass through the ICV under standard GI motility conditions. In some embodiments, the capability of the device 1000 to pass through the ICV in the emptying configuration may be defined in accordance with methods described in details herein below with reference to FIG. 12.

The trigger assembly 1040 may include a first support element 1042 configured for securing the first extension 1352 to the first coupling head 1032, and/or a second support element 1042 configured for securing the second extension 1354 to the second coupling head 1034.

In some embodiments, the support elements 1042, 1044 may have a pin shape. The first and second extensions 1352, 1354 may for example be shaped as socks in which the support elements 1042, 1044 can be inserted via the first and second external openings 1322, 1342. The pin-shaped support elements 1042, 1044 may be inserted in the first and second extensions 1352, 1354 while press-fitted inside the first and second hollow portions (of the first and second coupling heads 1032, 1034). The press-fitting may maintain the first and second extensions 1352, 1354 securely attached to the first and second coupling heads 1032, 1034. Alternatively or additionally, the first and second hollow portions of the first and second coupling heads 1032, 1034 may comprise locking corners 1325, 1345, that cooperate with an extremal portion of the pins-shaped support elements 1042, 1044, to locally increase the press-fitting force and improve retention of the resiliently deformable member 1035 by the support elements 1042, 1044.

In some embodiments, the support elements 1042, 1044 may be erodible elements configured to degrade when the device is exposed to an activation signal, and the erosion of the support elements releases the coupling heads 1032, 1034 from the resiliently deformable member 1035 so that the device is irreversibly allowed to go into the emptying configuration in which it may be capable of being emptied through the ICV. The support elements 1042, 1044 may be erodible layer-by-layer starting from the first and second external openings 1322, 1342, which are exposed to the environment of the device 1000, and going toward the first and second base openings 1324, 1344. As long as there remains at least a layer of a support element 1042 or 1044 with a diameter higher than a diameter of the first or second base opening 1324 or 1344, the support element 1042 or 1044 maintains its supporting function. As soon as the erosion reaches a (triggering) point where no such layer remains in the support element 1042 and/or 1044, the resiliently deformable member 1035 is free to retract and detach from the respective coupling head 1032 and/or 1034. Such a triggering point may be said to activate the trigger assembly 1040, and each support element 1042, 1044 may be referred to as a "timer".

Thanks to the first and second external openings 1322, 1342 being formed on top of the coupling heads 1032, 1034 (i.e., opposite to the base of the coupling heads 1032, 1034 where the articulated arms are coupled), the first and second external openings 1322, 1342 are oriented longitudinally (on axis X), with no element of the device 1000 forming an obstruction. This arrangement allows a particularly fine control of the support element or timers 1042, 1044, thereby, when at least one of the timers 1042, 1044 is triggered, the deformable resiliently deformable member 1035 may shrink backwards, thus releasing 1354 from the corresponding head openings 1322 or 1342 and the device unfolds.

Pin-shaped support elements 1042, 1044 may be made of any material and/or manufactured as described in reference to the device 100.

For example, pin-shaped support elements 1042, 1044 may be made of Eudragit® E may be manufactured as follows: a Hot Melt Extrusion machine is set to for example about 130° C. Eudragit® E powder is fed into the HME machine for example by a gravimetric feeder at a rate of 1 kg/hr. The HME machine snail speed is set to 100 rpm. The melted material is drawn from the HME machine, it is forwarded as strands onto a conveyor belt to cool. Once cooled, the strand is chopped by a chopping machine to a pin shape of about 1.5 mm diameter and 2 mm length.

For example, the support elements 1042, 1044 may be configured to be disabled after the device 1000 is exposed to standard ICV region environmental conditions for a predetermined residence time period, for example of one day, two days, three days or more and/or twelve weeks or less (e.g., any time period from 1 to 12 weeks, such as one month, one week, two weeks, three weeks, or even one day or two days). In other words, the trigger assembly 1030 may activate after the device is positioned at the ICV for a predetermined time period or after a predetermined time period elapsed subsequent to swallowing of the device.

The support elements 1042, 1044 may also or alternatively be configured to be disabled after the device is exposed to a predetermined set of activation environmental conditions. For example, the support elements 1042, 1044 may be configured to be disabled when a surrounding environment reaches (e.g., below) a predetermined pH threshold (e.g., pH 3, 4 or 5). For this purpose, the support elements 1042, 1044 may be erodible elements at least partially made of a material configured to dissolve (or degrade) when the surrounding pH reaches the predetermined pH threshold. In some embodiments the support elements 1042, 1044 may be at least partially made of a material dissolving at (i.e., when the pH reaches) the predetermined pH threshold. For example, the support elements may be made of an acid-soluble polymer. For example, the support elements 1042, 1044 may be at least partially made of a material soluble at pH below 5 such as Eudragit® E PO).

In some embodiments, the support elements 1042, 1044 may be at least partially made of a material dissolving in standard ICV region environmental conditions, such as hydroxypropylmethylcellulose (HPMC-AC), and coated with a material dissolving at the predetermined pH threshold, such as Eudragit® E PO. Such pin-shaped coated support elements may be manufactured as follows: Powder of HPMC AC is premixed with Dibutyl sebacate (DBS) in ratio of 8:1 in DIOSNA mixer for 5 minutes at 500 rpm. After premixing, the mixture is placed at room temperature for 24 h so that the polymer and plasticizer settle together. After 24 h, the mixture is fed into the HME machine. The HME machine is preheated to for example about 150° C. The HME machine snail speed is set to 100 rpm. As the melted material is drawn from the HME machine, it is forwarded as strands onto a cooling machine to cool on a conveyor belt. Once cooled, the strand is chopped by a chopping machine to pin shape of about 1.5 mm diameter and 2 mm length. The pins are then placed in a coating system (e.g., vector coater) and coated with Eudragit® E PO coating with a total of for example about 10% of weight gain.

The support elements 1042, 1044 may be arranged to form keystones of the device in the trapping configuration so as to provoke a collapse of the device into the emptying configuration after the device is exposed to the predetermined activation signal. In other words, the support elements 1042, 1044 are arranged to form one or more structural weak points. When the support elements 1042, 1044 are disabled, the one or more structural weak points cause the device to fall apart in the emptying configuration. The support elements 1042, 1044 are arranged so that a transfer duration of the device from the trapping configuration into the emptying configuration is substantially smaller (e.g., equal or less than ½, ⅓, ¼, ⅕, ⅙, ⅐, ⅛, ⅑, ¹⁄₁₀, ¹⁄₁₀₀, ¹⁄₁₀₀₀) than a standard residence time period (e.g., equal or more than 1, 2, 3, 4, 5, 6, 7 or 8 weeks). This provides an improved control of the device in in-vivo conditions. In particular, in embodiments in which the trigger assembly is activated by external means, this enables to quickly empty the device on-demand without requiring a colonoscopy procedure even in urgent cases.

In embodiments, the support elements 1042, 1044 may be configured to be disabled upon the device in the trapping configuration being exposed to a different activation signal. This provides flexibility in the manner of transferring the device 1000 into the emptying configuration. For example, the support elements 1042, 1044 may be made of different materials. For example, the support element 1042 may be made of a type A material, while the support element 1044 may be made of a type B material.

In specific implementations of the timer, the type A timer 1042 may be made of HPMC AS HG:MG:DBS ratio 8:2:1 by hot-melt extrusion. HPMC AS HG and HPMC AS MG powders may be placed in a (e.g., DIOSNA) mixer and mixed together. Then while mixing, a DBS solution may be added. After mixing, the granulate may be emptied from the mixer, transit through hot melt extrusion conveyed through a cooling system and chopped to pin beads. The type B timer 1044 may be made of Eudragit EPO by hot melt extrusion. The powder may transit through hot melt extrusion conveyed through a cooling system and chopped to pin beads. The chopped beads can be optionally be used as a raw material for injection molding to manufacture specific pin mold designs.

The device 1000 may be configured for the disassembling of the body 1010, formed by the articulated arms, from the first and second coupling heads 1032, 1034 upon activation of the trigger assembly 1040 (see FIG. 8F). Such exploding of the device 1000 from the trapping configuration into the emptying configuration facilitates the emptying when the trigger assembly 1040 activates, thus increasing safety of use. FIG. 8F shows an emptying configuration where not only the body 1010 is disassembled from both the first and second coupling heads 1032, 1034, but also the resiliently deformable member 1035 is disassembled from both the first and second coupling heads 1032, 1034. This is because both support elements 1042, 1044 have been degraded to an activation point. In embodiments, the device 1000 may achieve one or more other emptying configurations. For example, the resiliently deformable member 1035 may remain attached to one of the coupling heads 1032, 1034 and detach only from the other one, when only one of the support elements 1042, 1044 has been degraded to the activation point. This is likely to occur when different support elements/timers 1042, 1044 configured to degrade under different activations signals are used. Still, the body 1010 is disassembled from both the first and second coupling heads 1032, and this may be enough for a secure emptying.

In reference to FIGS. 8G-8J, the disassembling of the body 1010 from both the first and second coupling heads 1032 is now discussed in more details.

Figures 8G, 8H, 8I, 8J:
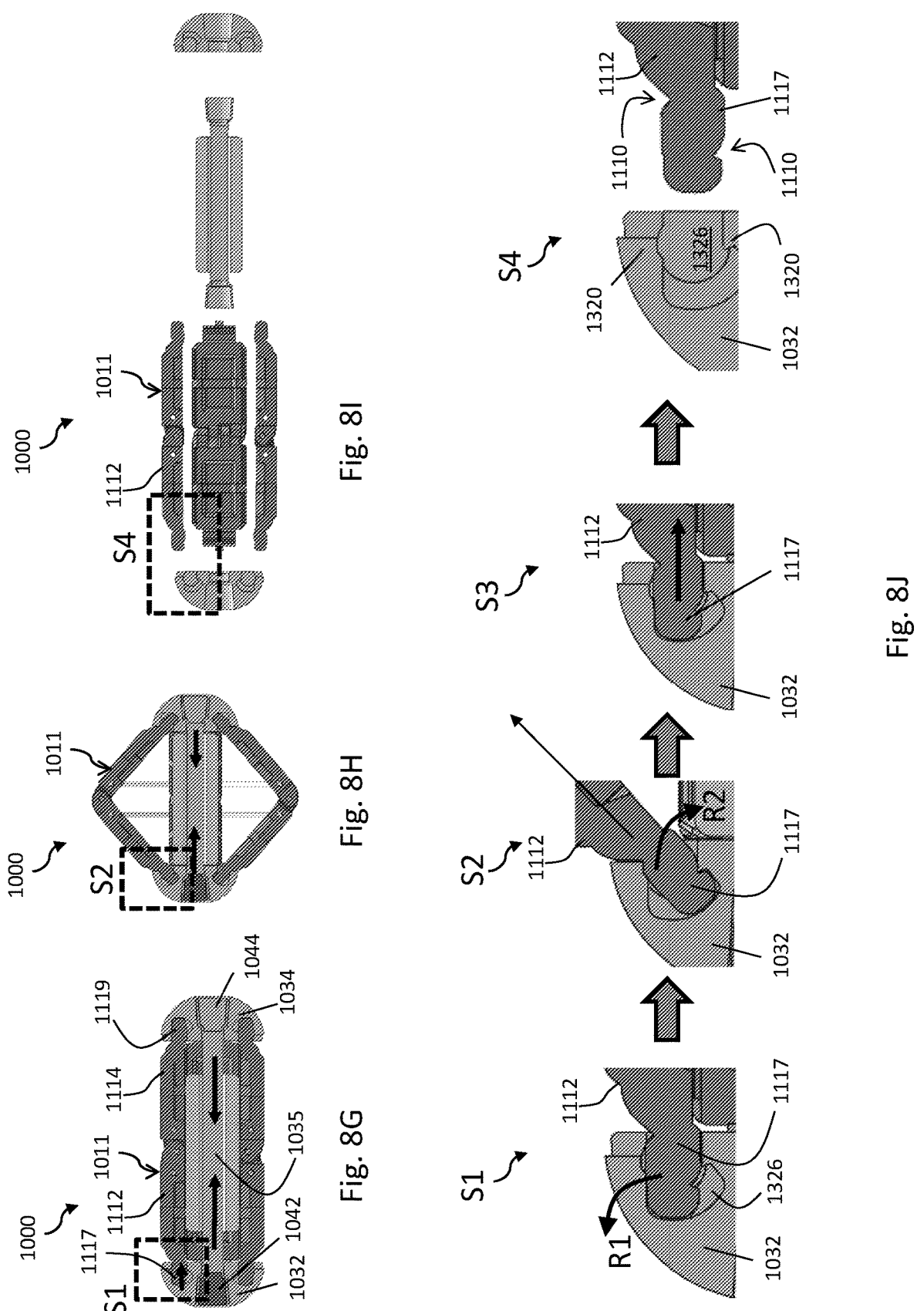
FIGS. 8G-8J illustrate a disassembling of the device according to embodiments of the present disclosure.

FIGS. 8G-8I show the device 1000 respectively in the closed, trapping, and emptying configuration, corresponding to a standard sequence of use of the device 1000. FIG. 8J further illustrates the sequence of use by showing close-up views of a zone S1-S4 of the device where the first arm section 1112 of the articulated arm 1011 is coupled to the first coupling head 1032.

As shown, the first end (e.g., 1117) of each articulated arm (e.g., 1011) is coupled to the first coupling head 1032 releasably, and the second end (e.g., 1119) of each articulated arm (e.g., 1011) is coupled to the second coupling head 1034 releasably. In the trapping configuration (see FIG. 8H), said first end 1117 is inserted in a respective cavity 1326 of the first coupling head 1032 (see FIG. 8J, last step, i.e., close-up S4), and said second end 1119 is inserted in a respective cavity of the second coupling head 1034 (not shown). Indeed, the resiliently deformable member 1035 maintains said first end and second end 1117 and 1119 each secured inside the respective cavities. This is thanks to the resiliently deformable member 1035 being securely attached to the first and second coupling heads 1032-1034 by the support elements 1042, 1044, thus pulling the first and second coupling heads 1032-1034 together when transferring from the closed configuration (FIG. 8G) into the trapping configuration (FIG. 8H), thereby exerting a pressure maintaining the articulated arms 1012-1014 therebetween in the trapping configuration. The retraction of the resiliently deformable member 1035 and the movement of the first and second coupling heads 1032-1034 one toward the other is represented by arrows on FIGS. 8G-8H.

The respective cavity 1326 of the first coupling head 1032 may be dedicated to the coupling of the articulated arm 1011, and each other articulated arm 1012-1014 may cooperate with a different other cavity of the first coupling head 1032. Such arm head cooperation increases the stability of the assembled device when in open unfolded configuration while exposed to external forces (e.g., when a force is applied on arm couplings, e.g., 1113) Similarly, the second coupling head 1034 may comprise a single cavity per articulated arm 1011-1014. Alternatively, any or both the first and second coupling heads 1032 and 1034 may comprise a circumferential cavity (e.g., 1326) configured to receive a respective end of each articulated arm 1011-1014.

Referring to FIG. 8J in particular, the discussion now focuses on the coupling and release of the first arm section 1112 of the articulated arm 1011 with respect to the first coupling head 1032. But the discussed coupling and release may identically apply to the first arm section of each other articulated arm 1012-1014 with respect to the first coupling head 1032, and/or to the second arm section (e.g., 1114) of each articulated arm 1011-1014 with respect to the second coupling head 1034.

The first end 1117 (and thus the first arm section 1112) may be rotatable in the respective cavity 1326. Thus, when the device 1000 transfers from the closed configuration (close-up S1) into the trapping configuration (close-up S2), the first end 1117 makes a rotation R1 relative to the first coupling head 1032, due the resiliently deformable member 1035 pulling the coupling heads 1032 and 1034 together. Similarly, when the device 1000 transfers from the trapping configuration (close-up S2) into the emptying configuration, the first end 1117 initially makes an inverse rotation R2 relative to the first coupling head 1032 (close-up S3), due to the resiliently deformable member 1035 being detached and thus stopping exerting its force, thus allowing the GI mechanical forces to apply on the device 1110 (e.g., due to chyme flow and tissue-induced pressures), thereby straightening the articulated arm 1011. Afterwards, when the device continues to transfer from the trapping configuration into the emptying configuration, the first end 1117 may be dimensioned to move out of the respective cavity 1326, due again to the GI mechanical forces. Thus, the first arm section 1112 and the first coupling head 1032 form a hinge disassembly mechanism.

As best seen on close-up S2, the first arm section 1112 may transit in an angle to the first coupling head 1032 and then be locked in head. The first coupling head 1032 may comprise for that a stopper mechanism. The stopper mechanism may comprise dents 1320 of the first coupling head 1032 cooperating with recesses 1110 of the first end 1117

(see close-up S4). Surfaces forming the recesses 1110 may engage surfaces forming the dents 1320, thereby preventing disassembly of the arm from the coupling head in the trapping configuration, even if GI mechanical forces increase.

In embodiments, in the folded configuration, the arm and head are orientated in a same axis while the arm is forced forward into the head cavity by the biasing member. During unfolding, the arm transits in an opposite angle to the head, and this positions the arm in a locking position within the head. After the timer is released, the biasing member is detached, the arm returns in a backward movement back into the folding position. As the biasing member is now detached, the arm is no longer forced into the head, and thus can be disassembled from the head when a mild external force is applied.

In specific implementations of the device 1000, preparation and assembly of the rigid device may be performed as follows. Device arms and may be made by Stratasys 3D printer rigid VERO or MEDIC medical grade material. Each two arms may be hinged together with a nylon pin. The biasing member may be made out of a silicone tube 55 A shore of about 3 mm² cross section may be pulled through one of the heads. The first end may be locked by a timer of type A (made of HPMC AS HG:MG:DBS ratio 8:2:1 by hot-melt extrusion). The second end may be pulled through a support tube made out of a silicone 55 a shore tube of 4 mm external diameter and 2 mm internal, and then through the second head and locked by a timer of type B (made of Eudragit EPO by hot-melt extrusion). The arms may be then hinged to the heads via the above-illustrated arm-head locking structure. A circumferential thread may be pulled through designated threading holes in the arms, and tied at the end.

FIGS. 9A-9C, FIGS. 9D-9E, and FIG. 9F show another example of a device 2000 for temporary ICV retention according to the present disclosure, respectively in a trapping (open) configuration (FIGS. 9A-9C), in a closed (swallowing) configuration (FIGS. 9D-9E), and in a disassembled configuration which may form an emptying configuration and/or a pre-assembling configuration during manufacturing (FIG. 9F). FIGS. 9A, 9D, and 9F show a front view of the device 2000. FIG. 9C shows a perspective view of the device 2000 in the same configuration as in FIG. 9A. FIGS. 9B and 9E show a longitudinal cross-section view (along axis X) of the device 2000 in the same configuration respectively as in FIGS. 9A and 9D, the cross-section being taken in a median plane of the device 2000 parallel to the view plane of respectively FIGS. 9A and 9D.

The device 2000 resembles the device 1000 discussed above in many aspects. Accordingly, numerals used to identify features of the device 1000 are incremented by a factor 1000 to identify like features of the device 2000. It is understood that the features which are similar to devices 100 and 1000 and combinable with device 2000 are not all repeated in details below.

The device 2000 may be deformable from the closed configuration of FIGS. 9D-9E into the expanded configuration of FIGS. 9A-9C, and the device 2000 may be irreversibly disassembled from the expanded configuration of FIGS. 9A-9C into an emptying configuration identical or similar to the disassembled configuration of FIG. 9F.

The device 2000 differs from the device 1000 mainly in that in the device 2000, at least one (e.g., all eight) of the arm sections 2112, 2114, 2122, 2124, 2132, 2134, 2142, 2144 comprises an exposed cavity (no numeral reference on the figures).

The cavity allows embedding any desired product inside the arm section. As the cavity is exposed, the embedded product is in fluid communication with the surrounding environment of the device 2000, notably when the device 2000 is in the trapping configuration. In examples, rigid arm sections may easily comprise such cavities thanks to their rigidity. In specific, because of said rigidity, the presence of the cavities does not prevent from having a sufficient structural rigidity of the device 2000, such that it better remains functional and open in the trapping configuration so as to be retained at the ICV location.

In particular, the cavity may contain an active pharmaceutical ingredient (API). The API may be provided within a solid form 2502 such as a tablet, which may optionally further contain one or more pharmaceutically acceptable excipients. The solid form 2502 may comprise a therapeutic payload of the API for local release and/or topical treatment of a patient condition at the ICV region or for systemic absorption. The API may be any one of the APIs mentioned earlier, and/or for the treatment of any disease or medical condition mentioned earlier. The API may be the same API as the one in the cooperating therapeutic oral dosage from (e.g., in the same or in a different dosage), or a different API. The solid form 2502 may comprise no protective cover (e.g., a coating), as the device 2000 may comprise a locking container for delivery at the ICV, thereby ensuring that the solid form 2502 remains functional (and optionally substantially intact) until it reaches the ICV region. Alternatively, the solid 2502 may have a coating and/or the exposure apertures 2508, 2510, 2512 (discussed hereinbelow) in the cavity may be coated, so as to expose the inner solid form 2502 only when desired. In variations, the API may be carried by the device in a semi-solid, powder, gel, or liquid form/texture, or in (any combination of) a solid, semi-solid, powder, gel, and/or liquid form (i.e., partly in one form, and partly in one or more other forms).

At least one (e.g., all eight) of the arm sections 2112, 2114, 2122, 2124, 2132, 2134, 2142, 2144 may comprise two components (e.g., recipient or body component 2504 and a cover component 2506) attached one to another and forming the exposed cavity therebetween. Numeral references are provided only for the arm section 2112 and its two components 2504 and 2506 (see FIG. 9F), for the sake of conciseness. Each such component (e.g., 2504 and 2506) may be rigid, and optionally integrally formed, for example made by injection molding or 3D printing or any other known way, from any material such as plastic, a biocompatible polymer such as cellulose acetate, resin, metal, or ceramic, as discussed with reference to the device 1000. The two components of each pair may be attached in any manner, for example snapped (i.e., clicked) one to another, e.g., after insertion of the solid form (e.g., tablet) 2502 between the two components. This facilitates manufacturing.

The at least one arm section (e.g., 2114) may comprise a peripheral wall. Each component of the at least one arm section (e.g., 2114) may comprise one or more respective walls, and said respective walls may compose the peripheral wall. The peripheral wall may have apertures 2508, 2510, 2512 (i.e., openings or holes) formed thereon, providing exposure of the cavity and thereby drug release at the ICV (see FIGS. 9B and 9C). The apertures 2508, 2510, 2512 connect the cavity with the environment of the device, thus putting the cavity into fluid communication with said environment.

One or more (e.g., all) recipient components (e.g., 2504) may comprise such drug release apertures 2508, and/or one or more (e.g., all) cover components (e.g., 2506) may comprise such drug release apertures 2510, 2512. This provides for drug release on one or both sides of each such arm section, thereby achieving a uniform diffusion of the solid form 2502. Alternatively, the apertures may present a design which provides a predetermined release rate.

As shown for the arm section 2114 (see FIGS. 9B and 9C), the recipient component may comprise one or more (e.g., exactly one) ranges of drug release apertures 2508, formed on an external envelope of the device 2000. Each range of drug release apertures 2508 may be linear, straight, and/or evenly distributed. Alternatively or additionally, the cover component may comprise one or more (e.g., exactly two) ranges of drug release apertures 2510, 2512. Each range of drug release apertures 2510 and/or 2512 may be linear, straight, and/or evenly distributed. Each arm section 2114 may present a generally prism shape with a triangle or trapeze cross-section. The drug release apertures 2508 may be formed on a face of the prism corresponding to the base of the triangle or trapeze (i.e., respective wall of the recipient component), and the drug release apertures 2510, 2512 may be formed each on a respective face of the prism to the sides of the triangle or trapeze (i.e., respective walls of the cover component). This achieves an even more uniform diffusion of the solid form 2502, by ensuring exposure everywhere of the cavities inside the arm sections.

The device 2000 may comprise no support tube surrounding the resiliently deformable member 2035. In turn, the arm sections 2112, 2114, 2122, 2124, 2132, 2134, 2142, 2144 may be dimensioned to encounter each other when the device 2000 reaches the trapping configuration (as best seen on FIG. 9C), thus maintaining a minimal distance between the two coupling heads 2032 and 2034, thereby preventing the device 2000 from expanding beyond the maximal authorized diameter. For example, the arm sections (e.g., 2132, 2134) of each articulated arm (e.g., 2013) may comprise each a sloped surface (e.g., 2532, 2534), and each such pair of sloped surfaces may be configured to abut one onto another, so as to block the relative rotation of the two arm sections of the pair (e.g., 2132 and 2134), beyond a predetermined abutment angle (see FIG. 9F). Thanks to the presence of the cavities (e.g., already embedding an API), the device 2000 may authorize a relatively reduced trapping volume (while allowing sufficient drug loading), thus allowing space occupancy induced by said abutting sloped surfaces (e.g., 2532, 2534). In variations, the device 2000 may comprise a support tube.

The device 2000 may comprise a unique thread 2015 located in a single plane. The thread 2015 may lie on a median plane (not shown) of the device 2000 substantially perpendicular to axis X. The hinge pins 2115 part of the pivot-type coupling between the arm sections may be hollow, and the thread may pass through said hinge pins 2115. In variations, the device 2000 may comprise several threads (e.g., in several planes) and/or a unique thread in several planes. Alternatively, the thread 2015 may be pulled through the hinge holes of the pivot-coupling hinge before the hinge pins are inserted, or threads may be glued to the hinge pins. Alternatively, the thread can serve as both a circumferential belt and a hinge pin The thread may be composed of two sections, including a more flexible sections and a more rigid and less flexible section (optionally also wider, designed to be retained by pressure in the hinges cavities). The thread may be pulled through the hinge hole while the rigid section may be placed and retained into the arm hinge as a pin.

In specific implementations of the device 2000, the device may include drug, placed in the arms. Device preparation and assembly may be according to the earlier-described first specific implementations of the device 1000, with the following difference. Before the arms are hinged together with a nylon pin, a tablet containing an API (a model tablet made by 3D printing VERO is used in experimental 2 discussed later) may be placed in each of the arm body cavities. Then, the arm cover may be clicked on the arm body/recipient to lock the tablet inside. Apertures may be designed in both arm body/recipient and the arm cover to allow drug release from arms.

Figures 10A, 10B, 10C, 10D, 10E, 10F:
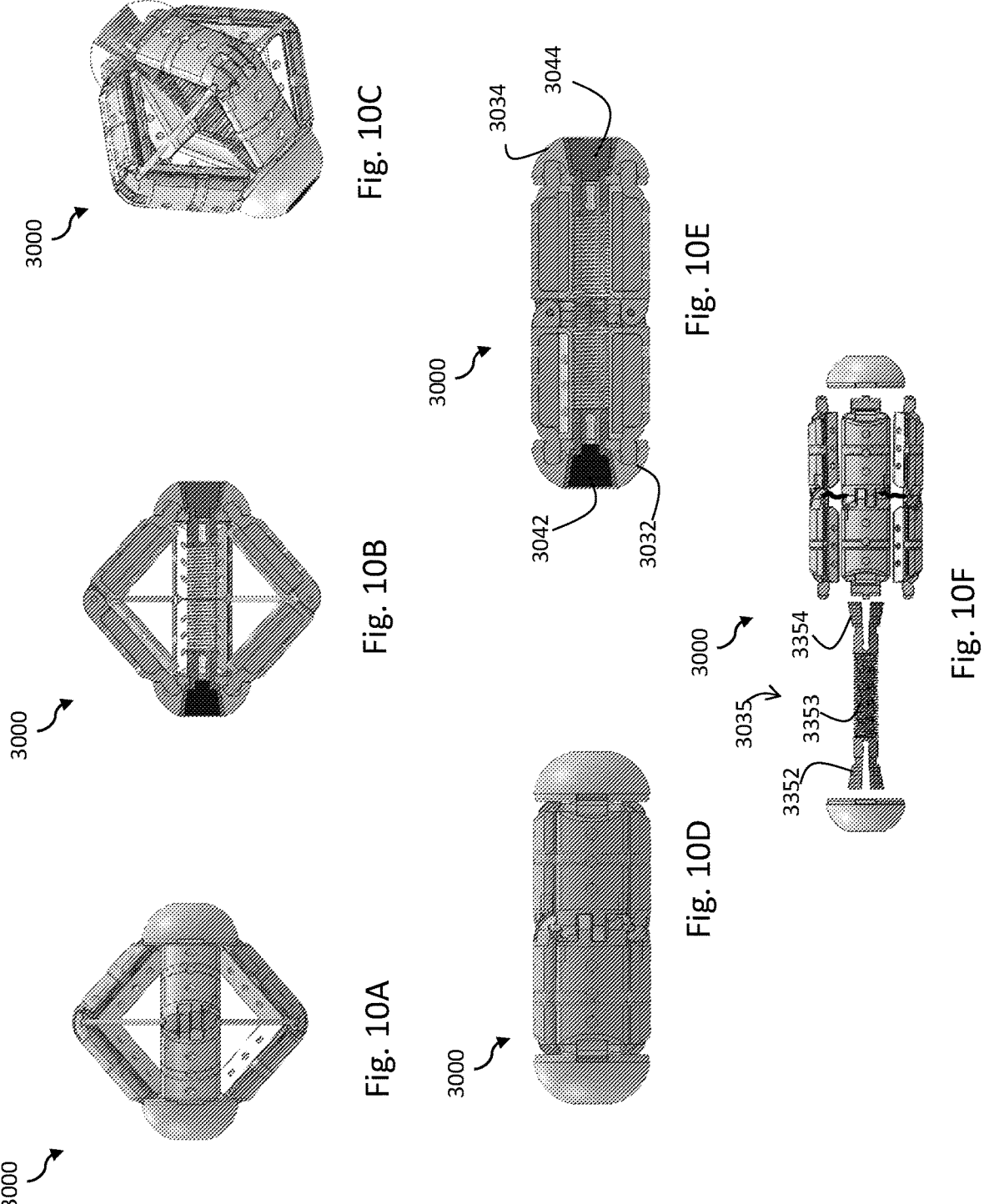
FIGS. 10A-10F illustrate another example of a device according to embodiments of the present disclosure.

FIGS. 10A-10C, FIGS. 10D-10E, and FIG. 10F show another example of a device 3000 for temporary ICV retention according to the present disclosure, respectively in a trapping (open) configuration (FIGS. 10A-10C), in a closed (swallowing) configuration (FIGS. 10D-10E), and in a disassembled configuration which may form an emptying configuration and/or a pre-assembling configuration during manufacturing (FIG. 10F). FIGS. 10A, 10D, and 10F show a front view of the device 3000. FIG. 10C shows a perspective view of the device 3000 in the same configuration as in FIG. 10A. FIGS. 10B and 10E show a longitudinal cross-section view (along axis X) of the device 3000 in the same configuration respectively as in FIGS. 10A and 10D, the cross-section being taken in a median plane of the device 3000 parallel to the view plane of respectively FIGS. 10A and 10D.

The device 3000 resembles the device 2000 discussed above in many aspects. Accordingly, numerals used to identify features of the device 1000 are incremented by a factor 2000 to identify like features of the device 3000. It is understood that the features which are similar to the devices 100, 1000, and 2000 and combinable with device 3000 are not all repeated in details below.

The device 3000 may be deformable from the closed configuration of FIGS. 10D-10E into the expanded configuration of FIGS. 10A-10C, and the device 3000 may be irreversibly disassembled from the expanded configuration of FIGS. 10A-10C into an emptying configuration identical or similar to the disassembled configuration of FIG. 10F.

The device 3000 differs from the device 2000 mainly in that in the device 3000, the resiliently deformable member is a spring 3035 configured to be stretched (e.g., traction spring), for example made of metal (such as stainless steel or Nitinol). A metal spring has little creep (low compression set) and at the same time a relatively high tension modulus (spring constant). This allows achieving a particularly high emptying force.

In embodiments, the spring 3035 allows achieving an emptying force higher than 500 gr (examples table 6). This may allow particularly long shelf life. Still, as the spring is further stretched when device is transit from open to closed configuration, the tension obtained during closed configuration may be substantially higher (e.g., 1000 gr).

The spring 3035 may comprise hinges 3352 and 3354 at its two ends (see FIG. 10F). The hinges 3352 and 3354 may be integrally formed with the stretchable central portion 3353 of the spring 3035. Once the timer 3042 and/or 3044 is eroded, the respective integral hinge 3352 and/or 3354 collapses, enabling the spring 3035 to detach from the respective coupling head 3032 and/or 3034 and disassembly to occur (see FIG. 10E).

In specific implementations of the device 3000, the device may be prepared as the device 2000, only replacing the elastic member by a stainless steel or Nitinol or the like having hinges as described above.

FIGS. 11A-11C, and FIGS. 11D-11E show another example of a device 1000' for temporary ICV retention according to the present disclosure, respectively in a trapping (open) configuration (FIGS. 11A-11C), and in a closed (swallowing) configuration (FIGS. 11D-11E). FIGS. 11A and 11D show a front view of the device 1000'. FIG. 11C shows a perspective view of the device 1000' in the same configuration as in FIG. 11A. FIG. 11B shows a longitudinal cross-section view (along axis X) of the device 1000' in the same configuration respectively as in FIGS. 11A and 11D, the cross-section being taken in a median plane of the device 1000' parallel to the view plane of respectively FIGS. 11A and 11D.

The device 1000' resembles the device 1000 discussed above in many aspects. Accordingly, numerals used to identify features of the device 1000 are appended a single quotation mark ' to identify like features of the device 1000'. It is understood that the features which are similar to device 1000 and combinable with device 1000' are not all repeated in details below.

Referring additionally to FIGS. 11G-11H, the device 1000' differs from the device 1000 mainly in that it does comprise a support tube 1038' in which the resiliently deformable member 1035' is arranged (see FIGS. 11B and 11G), but the support tube 1038' is different from the optional support tube 1038 of the device 1000.

The support tube 1038' has similarities with the optional support tube 1038, and in particular may be made of any material, such as a rigid material (e.g., plastic, metal, ceramic) or an elastic material. Also, the support tube 1038' may function as the optional support tube 1038. However, the support tube 1038' additionally has one or more (e.g., two) peripheral grooves 1382' (see FIG. 11G), each forming an exposed recess. Each exposed recess allows embedding any desired product. As the cavity is exposed, the embedded product is in fluid communication with the surrounding environment of the device 1000', notably when the device 1000' is in the trapping configuration.

In particular, the peripheral grooves 1382' may each lodge a ring-shaped form 1502' containing an active pharmaceutical ingredient (API). The forms 1502' may be solid and/or further contain one or more pharmaceutically acceptable excipients. The forms 1502' may comprise a therapeutic payload of the API for local release and/or topical treatment of a patient condition at the ICV region or for systemic absorption. The API may be any one of the APIs mentioned earlier, and/or for the treatment of any disease or medical condition mentioned earlier. The API may be the same API as the one in the cooperating therapeutic oral dosage from (e.g., in the same or in a different dosage), or a different API. The forms 1502' may comprise no protective cover (e.g., a coating), as the device 1000' may comprise a locking container for delivery at the ICV, thereby ensuring that the form 1502' remains functional (and optionally substantially intact) until it reaches the ICV region. Alternatively, the form 1502' may have a coating, so as to release the API only when desired. In variations, the API may be carried by the device in a semi-solid or gel form, or in (any combination of) a solid, semi-solid, powder, gel, and/or liquid form (i.e., partly in one form, and partly in one or more other forms).

The support tube 1038' may present a narrowed central section 1384' (see FIGS. 11F and 11G), to provide compactness to the device 1038', while the extremities of the support tube 1038' may have a larger diameter so that the peripheral grooves 1382' presents enough space to lodge the ring-shaped API. In turn, the articulated arms 1011'-1014' may comprise inner recesses 1380' (see FIG. 11B) to receive the extremities of the support tube 1038' (as best seen on FIG. 11E). These inner recesses 1380' (relative to the periphery of the device), allow compactness of the device 1000'. The rigidity of the arms facilitates the constructions of the inner recesses 1380', with reduced risks in terms of structural rigidity loss.

In addition, the device 1000' further differs from the device 1000 in that it comprises only one layer of circumferential threading 1015, similarly to device 2000.

In the above-discussed examples of the device, the device is configured to transfer from the trapping configuration into the emptying configuration upon the resiliently deformable member stopping to force the coupling heads together (e.g., due to release of the resiliently deformable member from one or both the coupling heads), for example when the device in the trapping configuration is exposed to a predetermined activation signal. In variations, the device may be configured to transfer from the trapping configuration into the emptying configuration upon the coupling heads or hooks stopping to compress and bend the arms, for example due to release of the coupling between the arms and the coupling heads. In examples, the coupling between the arms and the coupling heads may integrate one or more support elements constituting fixations between the arms and the coupling heads, while having triggering capabilities as described in the examples, and notably configured to degrade (e.g., when exposed to the predetermined activation signal) and thereby disassemble the arms from the coupling heads, while optionally the resiliently deformable member stays assembled to both the couplings heads (and may continue to force the coupling heads together).

In the above-discussed examples of the device, the resiliently deformable member (e.g., elastic or spring) is arranged between the arms. In variations, the resiliently deformable member may be arranged elsewhere. For example, the resiliently deformable member may be arranged on the sides of the arms, or inside the arms. In yet another example, the resiliently deformable member may form an arm of the device itself.

In the above-discussed examples of the device, the support elements (e.g., timers) are located inside the coupling heads or hooks, in particular in a hollow portion thereof. In variations, one or more support elements may be located elsewhere. For example, a resiliently deformable member (e.g., elastic or spring) may be made of two separate (i.e., initially disconnected) halves, the two halves being connected by a support element. When the support element degrades, the two halves disconnect, thereby the resiliently deformable member stops forcing the two coupling heads together and thus triggers transfer into the emptying configuration.

In the above-discussed examples of the device, the arms are each arranged longitudinally (on axis X) alongside each other. In variations, one or more of the arms may be arranged differently. For example, the arms may be twisted together.

In the above-discussed examples where the device carries a load of an API, the load of API may be distinct and separate from the support elements (e.g., timers). Each support element may be integrally formed, and the load of the API may be elsewhere. Notably, the support elements are located inside the coupling heads or hooks, while the discussed load of the API is located between the coupling heads or hooks and the arms. Optionally, the support element may comprise none of the API. In variations, the device may comprise one or more integrally formed blocks both forming a support element and carrying at least part of the load of the API. While releasing the API, the blocks erode to a point of degradation, thus triggering emptying of the device.

The above-discussed device may be adapted for a method of treating a condition which benefits from local dispensing of an active pharmaceutical ingredient in small intestine and at the ileocecal valve of a subject suffering from said condition, comprising administering to said subject the device, and subsequently administering the oral dosage form as discussed above, thereby treating said condition in said subject.

In examples where the device carries a load of an API, the treatment may combine the administration of an oral dosage form (to be trapped by the device) comprising an API and the release of a carried API (carried by the device, e.g., same API as the oral dosage form or different one), when the device is positioned at the ileocecal valve and in the trapping configuration, all while allowing chyme flow.

FIG. 12 illustrates retention testing equipment 200 that can be used in a method for assessing the capability of a device to pass through the ileocecal valve using retention testing equipment. Basically, a method for assessing the capability of a device to pass through the ICV comprises: providing a retention test device configured to simulate the geometry of a standard ICV region; placing a device in the retention test device upstream of a simulated ICV; applying sequentially on the device increasing forces (e.g., substantially constant forces), each forces being preferably applied for a predetermined test time period (e.g., about 10 seconds), wherein said forces tend to pull the device out of the simulated ICV, until an extraction force which is sufficient for extracting the device from the simulated ICV within the test time period is reached; comparing the extraction force to a predetermined threshold (e.g., about 1.5 N) defining a minimal retention capability.

The retention test equipment 200 may include a retention test device 210 (also referred to as simulated ICV) and a mounting support 250 for maintaining the retention test equipment vertically so that gravity tends to extract the device 100 through the simulated ICV.

The retention test device 210 for simulating the geometry of standard ICV region may generally include a funnel portion reproducing the narrowing of the ICV. In more details, the test device 210 may comprise a first tubing portion 211 of a first diameter D1 joined at its connecting end to a narrowing truncated conical portion 212. An end of the truncated conical portion 212 opposed to the connecting end may be of a second diameter D2 smaller than D1. The narrowing conical portion 212 may be concentric to a second tubing portion 213 surrounding the narrowing conical portion 212. The second tubing portion 213 may be joined to the connecting end of the first tubing portion 211. In some embodiments, as illustrated, the first and second tubing portions 211 and 213 may be of same diameter D1 and form a single tube. In some embodiments, the inner surface of the retention test device may be lubricated, for example with an edible oil, for example corn oil. In the following, the first tubing portion 211 and the narrowing portion 212 are also referred together as donor chamber and the second tubing portion 213 is also referred to as acceptor chamber. The first tubing portion 211 may be configured to simulate the small intestine geometry, more particularly the terminal ileum region of the small intestine while the second tubing portion 213 to simulate the cecum in the large intestine. The first diameter D1 of the first tubing portion 211 may be of about 20 to 35 mm, preferably of about 30 mm. A length of the first tubing portion 211 may be of about 100 mm. The conical narrowing portion 212 may be configured to simulate the ICV geometry. A length of the narrowing conical portion may be of about 12 mm. The second diameter D2 may be of about 10 to 20 mm, preferably of 16 mm. A length of the second tubing portion 213 may be of about 70 mm. The retention test device 210 may be made out of a rigid material.

The device 100 may be positioned at the connecting end of the first tubing portion 211 i.e., at the enlarged part of the funnel. The device 100 may be wrapped into a foil 230 on which increasing weights may be attached so as to pull the device out of the donor chamber into the acceptor chamber. The foil 230 may be preferably made of low density polyethylene with a thickness of about 10 microns. The foil may preferably have a rectangular shape of about 19 cm by 25 cm. An external surface of the foil 230 in contact with the test device 210 may be lubricated, preferably with corn oil.

The foil 230 may be sequentially attached to increasing weights in order to apply increasing forces on the device. The weights may be between about 10 gr to 400 gr or 500 gr. A predetermined extraction force threshold may correspond to a predetermined extraction weight threshold. The predetermined extraction weight threshold defining a (minimal) satisfying retention capability may be of about 100 gr, 150 gr or 200 gr, 250 gr, 300 gr, 400 gr or 500 gr.

In some embodiments, the previously described method may be repeated several times and an average extraction force needed to extract the device out of the simulated ICV may be determined.

The previously described method may advantageously be used to determine the capability of a device in the trapping configuration to be retained at the ICV i.e., to not pass through the ICV. In these embodiments, the device in the trapping configuration is considered to satisfy the retention capability if the measured extraction force is above the predetermined minimal retention threshold. In some embodiments, the method previously described may also be used to determine the capability of a device in the emptying configuration to be emptied i.e., to pass through the ICV. In these embodiments, the comparing step may instead be: comparing the extraction force to a predetermined threshold defining a maximum acceptable retention capability. In these embodiments, the device in the emptying configuration is considered to satisfy the emptying capability if the measured extraction force is below the predetermined maximal retention threshold.

In particular, a method for determining the retention capability of a device includes: providing a retention test device mounted vertically, wherein the retention device includes a first tubing portion of a first diameter of about 30 mm joined at its connecting end to a narrowing truncated conical portion, an end of the truncated conical portion opposed to the connecting end being of a second diameter of about 16 mm, a length of the first tubing portion being of about 100 mm, a length of the narrowing truncated conical portion being of about 12 mm, the first tubing portion and narrowing truncated conical portion may be of rigid plastic; placing a device on the narrowing truncated conical portion; applying sequentially on the device increasing forces (e.g., substantially constant forces), each forces being preferably applied for about 10 seconds, wherein said forces tend to pull the device out of the narrowing truncated conical portion, until an extraction force which is sufficient for extracting the device from the narrowing truncated conical portion within 10 seconds is reached; comparing the extraction force to a predetermined threshold of about 1.5 N or 2.0 N.

FIG. 13 shows a trapping test equipment 300 useful in a method for assessing the capability of a device to block corresponding objects while allowing chyme flow when the device is positioned at the ICV.

Basically, a method for assessing the capability of a device to block predetermined corresponding objects while allowing chyme flow may comprise: providing a trapping test device configured to simulate the geometry of a standard ICV region; placing the device in the trapping test device at a position upstream of a simulated ICV; placing at least one corresponding object (or an object substantially geometrically similar to the corresponding object) upstream of the device; placing at least one chyme representative object configured to simulate standard maximal chyme elements at the ICV region upstream of the device; exposing the trapping test device to simulated standard GI motility conditions for a predetermined trapping test time period; determining how much of the at least one corresponding object and of the at least one chyme imitator object have passed through the simulated ICV after the predetermined trapping test period.

The trapping test equipment 300 may include a trapping test device 310 and a rotating system 350.

The trapping test device 310 resembles the retention test device 210 discussed above in that it is configured to simulate the geometry of an ICV. Accordingly, numerals used to identify features of the device 100 are incremented by a factor 100 to identify like features of the retention test device 210.

As previously described with reference to the simulated ICV in the retention test device 210, the trapping test device 310 includes a simulated ICV comprising: a first tubing portion 311, a narrowing truncated conical portion 312 and a second tubing portion 313. Additionally, the trapping test device 310 includes a proximal cover 314 for sealing an upstream end of the first tubing portion (i.e., an end opposed to the connecting end of the first tubing portion 311) and a distal cover 315 for sealing a downstream end of the second tubing portion (i.e., an end opposed to the end of second tubing portion 312 connected to the first tubing portion 311). The distal cover 315 may include a valve mechanism to allow objects passing through the narrowing portion 212 to be captured at the bottom of the acceptor chamber. A length of the distal cover may be of about 14 mm.

The device 100 may be positioned at the connecting end of the first tubing portion 311 i.e., resting upwards of the enlarged part of the funnel.

In order to test the capability of a device to block corresponding objects while allowing chyme flow, at least a corresponding object 500 and at least a chyme representative object 400 may be placed upstream of the device 100.

In order to test the capability of the device to block a predetermined corresponding object, the corresponding object 500 may optionally be replaced in the trapping test method by a spherical bead of a diameter equal to a relevant extension (e.g., in some embodiments a minimal cross sectional diameter) of the corresponding object intended to be trapped on the device. For example, the corresponding object may be a dosage form having a capsule shape (roughly similar to a cylindrical shape) of diameter D and height h, and the spherical bead may be of diameter D. For example, such spherical beads substantially similar geometrically to the dosage forms intended to be trapped on the device may be of about 12 mm. The spherical beads may optionally be made of glass.

The at least one chyme representative object 400 may be spherical beads of a diameter of about 6 mm. Such size is representative of standard maximal chyme elements at the ICV region. It is understood that such standard maximal chyme element size is referring to standard ingested food i.e., provided that the subject does not ingest food with large non-edible elements e.g., fruit pits from dates, plums, apricot, etc.

The rotating system 350 may enable to simulate GI motility. For example, the rotating system may enable to rotate the trapping test equipment 300 together with the device 100, the at least one corresponding object 500 and the at least one chyme representative object 400 at a rate of between about 2 to 20 rpm. A diameter of the rotation movement may be between about 250 mm to 350 mm. Additionally, in order to simulate standard GI motility conditions, a weight 330 may be placed upstream of the device 100 so as to push the device through the simulated ICV (donor chamber). The weight may be of about 30 to 100 g. The weight may have a first cylindrical portion prolonged by a second narrowing truncated conical portion intended to be in contact with the device 100 and to enable the weight to push the device into the second tubing portion 313. The first cylindrical portion may have a diameter of about 28 mm or 30 mm and a length of about 75 mm to 100 mm, more preferably 85 mm. The second truncated conical portion may be 10 mm long and a diameter at the end of the truncated conical portion may be of about 14 mm. Additionally, in order to simulate standard human GI motility conditions, a solution of sodium phosphate buffer at concentration of 0.015M, pH 6.8 may be added in the test device 310. Alternatively a sodium phosphate buffer solution 0.015 to 0.035 M, having a pH of 6.5 to pH 7.5 can be used. Additionally, the temperature of the solution may be maintained at about 37° C. For example, the rotating system 350 may include a bath at 37° C. in which the rotation is performed.

Following exposure of the device to simulated GI motility conditions for the predetermined trapping test time period, for example by rotation in the rotating system 350 at 5 rpm for 30 minutes, a ratio between the amount of cooperating objects having passed through the simulated ICV (i.e., captured by the distal cover 315) and the amount of cooperating placed initially upwards of the device can be determined. The ratio can be compared with a predetermined threshold representative of a maximal expected trapping failure rate.

Similarly, a ratio between the amount of chyme representative objects having passed through the simulated ICV (i.e., captured by the distal cover 315) and the amount of chyme representative objects placed initially upstream of the device can be determined. The ratio can be compared with a predetermined threshold representative of a minimal expected trapping success rate.

In particular, a method for testing the capability of a device to block predetermined cooperating objects while allowing chyme flow when the device is positioned at the ICV includes:

providing a trapping test device;

wherein the trapping test device includes a first tubing portion of a first diameter of about 30 mm joined at its connecting end to a narrowing truncated conical portion, an end of the truncated conical portion opposed to the connecting end being of a second diameter of about 16 mm, a length of the first tubing portion being of about 100 mm, a length of the narrowing truncated conical portion being of about 12 mm, the first tubing portion being further connected at its connecting end to a second tubing portion of diameter 30 mm, the second tubing portion being 96 mm long and comprising a distal cover sealing a distal end of the second tubing portion, the distal cover including valve mechanism to allow objects passing through the narrowing portion to be captured at a distal end of the second tubing portion, the first tubing portion comprising a proximal cover sealing the proximal end of the first tubing portion, the first tubing portion, second tubing portion and narrowing truncated conical portion being made of rigid plastic;

placing the device in the trapping test device over the narrowing truncated conical portion;

placing at least one (e.g., 3) corresponding object (or an object substantially geometrically similar to the corresponding object) upstream of the device;

placing at least one (e.g., 3) glass spherical bead of about 6 mm diameter upstream of the device;

adding a solution of buffer phosphate 0.015N, pH 6.8 at 37° C. in the trapping test device;

placing a weight of 100 g upstream of the device;

rotating the trapping test device and its content at 5 rpm for 30 minutes in a bath maintained at 37° C.;

determining how many of the at least one corresponding object and of the glass spherical beads have passed through the simulated ICV after the 30 minutes period.

This invention will be better understood by reference to the experimental details, which follow, but those skilled in the art will readily appreciate that the specific experiments detailed are only illustrative.

Experimental 1

1. In Vitro Testing of a Device According to the Present Disclosure

Test results obtained with a device having a structure as shown in FIG. 1 and manufactured according to the assembly method detailed hereinabove (four arm device with support elements as Eudragit E pins i.e., degradable at pH below 5) is now described.

Shelf Life Test

The device was subject to shelf life tests. The device was placed in the closed configuration within a capsule container of 30 mm height by 11 mm diameter. After respectively 1 day, 7 days, the device was extracted from the capsule and subject to the test described with reference to FIG. 13 to determine if it maintained its properties of blocking 12 mm spherical glass beads (representative of the dosage forms intended to be blocked by the device) while allowing passage of 6 mm spherical glass beads (representative of standard maximal chyme elements present at the ICV). The device was also subject to the test described with reference to FIG. 12 to determine if it maintained its property of not passing through the ICV in the trapping configuration.

The results are listed in table 1 below:

TABLE 1

| | Shelf life test results | | |
|---|---|---|---|
| Days | % of 12 mm glass beads blocked * | % of 6 mm glass beads blocked ** | Emptying force (D 2 = 16 mm) |
| 0 | 100% | 0% | 1.5N |
| 1 | 100% | 0% | 1.5N |
| 7 | 100% | 0% | 1.5N |

* 5 beads tested 4 times
** 2 beads tested 4 times

Drug Release Test

The device was placed within a drug release test device similar to the trapping test device described on FIG. 13 with the difference that the drug release test device has a donor chamber of a diameter D1 of 30 mm, a second diameter of the truncated conical narrowing portion being of about 15 mm and the weight being of 50 g. An API carrying drug (ACD) was prepared by mixing mesalamine, Kollidon SR, Polyox WSR N60K, Avicel 102, Carbopol 71G, crosspovidone XL together for 10 minutes. Magnesium stearate was then added followed by additional 5 minutes mixing. The mixture was then compressed in an oval die by 2 ton press into an oval shape tablet of a weight of about 1070 mg and dimensions of 9.7 length by 19.65 mm width and 8.05 mm thickness. The tablets were then coated by 9% weight gain of Eudragit® L coating (Eudragit L coating composition: 6.5 mg Dibutyl Sebacate, 12.6 mg Talc USP extra fine, 2 mg Ferric oxide red, 75 mg Eudragit® L-100, 855 mg IPA and 215 mg acetone per tablet).

An API tablet (i.e., therapeutic oral dosage form) was then placed into the drug release test device described above without the trapping device. A solution to simulate the GI conditions was added into the chamber and replaced every hour according to the characteristics listed in the table below. The system was placed on a rotating system in a bath at 37° C. and rotation set to 5 rpm. Every hour, the amount of drug in the intestinal simulating solution was measured. At time 1 hr, 2 hr (representing tablet transit from stomach till ICV) after the simulated solution was replaced the tablet was placed again into the release test device. At 3 hr, after addition of intestinal simulation solution, the trapping device was first placed in donor chamber and then the tablet was placed above it. Then, every hour, before simulation solution was replaced, the location (donor chamber/acceptor chamber) of the tablet was recorded.

The results are listed in the table 2 below.

TABLE 2

| | Drug release test results | | |
|---|---|---|---|
| Time (h) | Solution | % tabs in donor chamber * | Accumulated API release (%) ** |
| 0 | HCl 0.1M | N/A | 0 |
| 1 | Buffer phosphate 0.015M, pH 6 | N/A | 0 |
| 2 | Buffer phosphate 0.015M, pH 6.5 | N/A | 0 |
| 3 | Buffer phosphate 0.03M, pH 7.2 | N/A | 1.1 |
| 4 | Buffer phosphate 0.03M, pH 7.2 | 100% | 2 |
| 5 | Buffer phosphate 0.03M, pH 7.2 | 100% | 8.7 |
| 6 | Buffer phosphate 0.03M, pH 7.2 | 100% | 26.1 |
| 7 | Buffer phosphate 0.03M, pH 7.2 | 100% | 51.7 |
| 8 | Buffer phosphate 0.03M, pH 7.2 | 66% | 88.1 |
| 9 | Buffer phosphate 0.03M, pH 7.2 | 0% | 100 |
| 10 | Buffer phosphate 0.03M, pH 7.2 | 0% | 100 |
| 11 | Buffer phosphate 0.03M, pH 7.2 | 0% | 100 |
| 12 | Buffer phosphate 0.03M, pH 7.2 | 0% | 100 |
| 24 | Buffer phosphate 0.03M, pH 7.2 | 0% | 100 |

* average on 10 tests performed
** of all collected samples

The API tablet shows accumulated drug release of less than 10% within first 3 hr (time when ACD would—in vivo—transit from stomach to ICV), while above 60% between 3-10 hr (time when ACD would—in vivo—in the ICV region).

Emptying Test

An emptying tablet (i.e., oral dosage form for cooperation with the device to trigger emptying when the trigger assembly is configured to activate when the device in the trapping configuration is exposed to a surrounding environment of a pH being below a predetermined threshold of, for example pH 5) is designed to withstand gastric acidic pH, transit along the small intestine, being retained at the ICV by being blocked on the device, release its acidic payload (emptying agent) thereby lowering the surrounding environment pH, enabling activation of the trigger assembly (i.e., in the case of the device tested: erosion of the Eudragit E pins as support elements) and causing transfer of the device into the emptying configuration.

An exemplary emptying tablet composition is presented in the table below. The emptying tablet can be obtained as follows: Citric acid, Methocel® K100LV, Lactose SD and Avicel® 101 are mixed together for 10 min. Magnesium stearate is then added followed by additional 5 min mixing. The mixture is then compressed in an oval die by 2 Ton press into oval shape tablet weight of about 1600 mg and dimensions of 21.9 mm length by 10.9 mm width by 9.3 mm thickness. The tablets are then coated with 13% by weight of Eudragit® L coating (composition described below), in vector coater (inlet 25° C., 1250 nBar automizing pressure, Pan speed 15 RPM).

TABLE 3

Exemplary composition of emptying tablet

| core tablet | mg | coating | mg |
|---|---|---|---|
| Citric acid | 648.0 | Talc USP extra fine | 27.9 |
| Methocel K100LV | 180.0 | Ferric oxide red | 4.4 |
| Lactose SD | 360.0 | Eudragit L-100 | 166.3 |
| avicel | 396.0 | IPA | 1895.8 |
| MgS | 14.4 | ACETONE | 476.7 |
| SUM | 1598.4 | SUM (solids) | 206.5 |

The test device was tested to ensure transfer into the emptying configuration and emptying using the above described emptying tablet.

The device was first placed in a system for testing collapse and emptying of the device (an "emptying tablet test device") similar to the trapping test device described on FIG. 13 with the difference that the emptying tablet test device has a donor chamber of a diameter D1 of 30 mm, a second diameter D2 of the truncated conical narrowing portion being of about 15 mm and the weight being of 50 gr. A solution to simulate GI conditions was added into the chamber and replaced every hour according to the following pattern: 0-1 h, HCl 0.1M; 1-2 h Buffer phosphate pH 6; 2-3 h buffer phosphate pH 6.5; 3-24 h buffer phosphate pH 7.2 0.03M. Two emptying tablets as described above were placed in the donor chamber, the test device was then sealed and fixed onto a rotating system in a bath at 37° C. at 5 rpm. At 3 hr, after addition of intestinal simulation solution, the trapping device was first placed in donor chamber and then the tablet was placed above it. From then on, every hour, the device configuration (trapping configuration or emptying configuration) and location (donor or acceptor chamber) were documented. Upon hourly check, a new acidic tablet was added in case the first tablet had passed into the acceptor chamber. The test was repeated four times. For the four times, the trapper transferred into the emptying configuration and was found in the acceptor chamber within 9 hr. Two acid tablets (i.e., emptying dosage forms) were used.

2. Exemplary Pre-Clinical In Vivo Study

An exemplary device is administered to animals to test performance (administration, maintenance of the device at the ICV and emptying through body) of the device. The device features, including trapper dimensions, timer pin, API containing tablet and emptying tablet are based on the principles described in the disclosure, and adapted for administration to pigs. Exemplary features are provided in table 4 below.

TABLE 4

Device features for preclinical in vivo study

| | Platform 1 | Platform 2 | Platform 3 |
|---|---|---|---|
| Trapping configuration diameter (mm) | 23 | 26 | 26 |
| Padding system | No | No | Yes |
| Meshwork (mm$^2$) | 160-200 | 160-200 | 160-200 |
| length/diameter (mm) | <35/12 | <35/12 | <35/12 |
| Timer pin material | Eudragit EPO | Eudragit EPO | Eudragit EPO |
| API releasing tablet: 12 hr release profile | Placebo/ barium | Placebo/ barium | Placebo/ barium |
| Emptying tablet | Citrate/ barium | Citrate/ barium | Citrate/ barium |

The trapping device as well as the API and emptying tablets are labeled with barium to enable detection by X-ray imaging.

Animals: 2-6 domestic pigs, each weighing 40-70 kg are acclimated in pens for 2-7 days before dosing. The animals are weighed and food consumption is assessed at baseline.

Study procedures (dosing and monitoring) are performed as described below.

Dosing is carried out every morning under fasted conditions.

Optionally right before dosing, 5-10 cc of lubricating oil is given to the animals to smooth the transit of the device and or tablets dosed. X-ray imaging is performed based on study protocol (e.g., every 6-12 hr)

A summary of the study protocol is provided in table 5 below.

TABLE 5

Exemplary in vivo study protocol in domestic pigs.

| Step | Test | Goal | Days |
|---|---|---|---|
| 1 | Control labeled tablet + 10 labeled 5 mm beads + optionally labeled food | Show transit through GI and passage through ICV within <12 hr (of controlled tablet and at least 50% of the beads) | 1 |
| 2 | TICS dosing (platform 1) | Show transit and retention <48 hr (12 hr retention > control tablet) | 1-3 |
| 3 | Placebo labeled tablet + 10 labeled 5 mm beads + optionally labeled food | Retention of tablet at least 6-12 hr, while beads pass | 1-2 |
| 4 | Emptying tablet | <7 days to disassembly of trapping device (dosing every 12 hours) | 1-5 |
| 5 | Animal health | Weight, food consumption, general health | Entire study |
| 6 | Macro tissue status and gross pathology | Evaluate tissue any possible tissue damage. | |

Control tablet is labeled and has same dimensions as a therapeutic tablet but is non erodible (or has low erodibility) and does not downsize in the GI. This enables to check how a tablet transits along the GI.

Step 1: The control low erodible tablet (>48 hr to disintegration) sized about 8 mm×20 mm and about 10 barium beads, each about 4 mm-6 mm (e.g., 5 mm) is delivered into duodenum by endoscope through animal's mouth and X-ray imaging is performed every 6-12 hr to evaluate transit. The method shows that the control tablet and beads pass through the ICV into the large intestine within 24 hr.

Step 2: Delivery of trapping device platform 1, directly into the duodenum by upper endoscopy. X-ray imaging is performed every 6-12 hr up to 48 hours post administration, to evaluate transit and retention of the trapping device at the ICV. The trapping device transits within 48 hr to the ICV in a closed configuration, converts to a trapping configuration at or near the ICV and is retained proximal to the ICV for at least 12 hr longer than retention of the dummy tablet.

Trapper platforms 2 or 3 (26 mm) are tested as alternatives.

Step 3: Following retention of the trapper at the ICV for at least 12 hr longer than the dummy tablet, a placebo barium labeled tablet and about 10 barium beads of 4-6 mm are dosed into the duodenum (orally with endoscope). The placebo tablet has dimensions enabling it to be blocked by the trapping device and is configured to release a placebo formulation at the ICV. Release of the formulation causes the placebo tablet to downsize as for a therapeutic dosage form according to the present disclosure. The placebo tablet is retained for at least 6-12 hr longer than the control tablet, while emptying within 48 hr from dosing whereas the beads pass through the trapper within ±6 hr of the beads tested in step 1. This shows that standard chyme is able to pass through the trapper.

Step 4: Following step 3, 1 to 4 barium labeled emptying tablets (comprising citric acid) are dosed into the duodenum (orally with endoscope). The emptying tablet has dimensions enabling it to be blocked by the trapping device and is configured to release the citric acid at the ICV. Release of the citric acid causes the emptying tablet to downsize. Every 6-24 hr, X-ray imaging is performed to assess transit of the tablet(s) and progression of trapper transfer into the emptying configuration. If the trapper does not transfer into the emptying configuration, an additional 1 to 4 tablets will be given (e.g., every 12 hr). This procedure is repeated until the trapper empties (i.e., exits) the ICV to the large intestine. The trapper transfers into the emptying configuration and empties from the ICV within less than 14 days, less than 10 days and preferably less than 7 days.

Step 5: Throughout the study, animal health, food consumption and weight are monitored.

Step 6: At 0 hr to 96 hr after emptying of the trapper through the ICV, the animal is sacrificed and gastrointestinal tissue taken for macro gross pathology examination Study Success Criteria
1. Trapper transits to ICV within about 72 hr or less;
2. Trapper is retained at the ICV (proximal to ICV in ileum) for at least 12 hr longer than the dummy tablet;
3. Retention of objects (e.g., API releasing tablet) for at least 6 hr longer than the dummy tablet;
4. Passage of beads when trapper is positioned at the ICV is similar to passage of when no trapper present.
5. TICS transfers into the emptying configuration and emptying occurs within 14 days, preferably within 7 days from administration of acid tablets (trapper emptying tablets)

Safety:
a) No significant adverse events are observed by the veterinarian.
b) Acceptable health status and acceptable food consumption and weight observed.
c) Food transit (e.g., labeled food or as simulated by beads) is not obstructed by trapper.

Pathology:
a) Acceptable gross pathology of ICV at all times from 0 hr to 96 hr after TICS is emptied
b) No macro hemorrhages at ICV region
c) None to minimal effect of ICV functions—e.g., no backward flow from colon into ileum.

Experimental 2

1. In Vitro Testing of Devices 1000, 2000 and 3000
Device 1000
A device was prepared in accordance with the implementations of device 1000. The assembled device was then subjected to the two in vitro retention (emptying) tests, as described in reference to FIGS. 12-13 (with D1=30 mm, and D2=16 mm or 18 mm). Test results were acceptable. 100% of the 12 mm glass beads were blocked, 0% of the 6 mm glass beads were retained, the emptying force was 3.5N (D2=16) and 2.5N mm (D2=18 mm). Results are summarized in table 6 below.
Device 2000
A device was prepared in accordance with the implementations of device 2000. The assembled device was then subjected to the two in vitro retention (emptying) tests, as described in reference to FIGS. 12-13 (with D1=30 mm, and D2=16 mm or 18 mm). Test results were acceptable. 100% of the 12 mm glass beads were blocked, 0% of the 6 mm glass beads were retained, the emptying force was 3N (D2=16 mm) and about 2N (D2=18 mm). Results are summarized in table 6 below.
Device 3000
A device was prepared in accordance with the implementations of device 3000. The assembled device was then subjected to two in vitro retention test, as described in reference to FIGS. 12-13 (D1=30 mm, D2=16 mm or 18 mm). Test results where acceptable. 100% of the 12 mm glass beads were blocked, 0% of the 6 mm glass beads were retained, the emptying force was >5N (D2=16 mm) and about 4N (D2=18 mm). Results are summarized in table 6 below.

Summary

The rigid structure of the tested devices enables significant achievements. While maintaining trapping capabilities (12 mm beads retention, 6 mm beads transit), it achieves higher device retention (in-vitro emptying force test), higher volume void enabling drug loading in trapper and small capsule size, enabling easy swallowing.

TABLE 6

| | | | | | emptying force, (grF) * (D2 = 16 mm) | emptying force (grF) * (D2 = 18 mm) | % of 12 mm glass beads blocked | % of 6 mm glass beads blocked |
|---|---|---|---|---|---|---|---|---|
| device | biasing system | folded dimension (Ø, length in mm) | unfolded dimensions (Ø in mm) | potential capsule dimension | | | | |
| 1000 | silicone | 9.8, 28.8 | 24 | 10.2, 29 | 350 | 250 | 100% | 0% |
| 2000 | silicone | 9.8, 28.8 | 24 | 10.2, 29 | 350 | 250 | 100% | 0% | results of in-vitro testing

TABLE 6-continued

| | | | | | emptying force, (grF) * (D2 = 16 mm) | emptying force (grF) * (D2 = 18 mm) | % of 12 mm glass beads blocked | % of 6 mm glass beads blocked |
|---|---|---|---|---|---|---|---|---|
| device | biasing system | folded dimension (Ø, length in mm) | unfolded dimensions (Ø in mm) | potential capsule dimension | | | | |
| 3000 | stainless steel spring | 9.8, 28.8 | 24 | 10.2, 29 | >500 | >500 | 100% | 0% |
| 4000 | stainless steel spring | 10.2, 29 | 24.5 | 10.5, 29.5 | >500 | >500 | 100% | 0% |

* emptying test applied right after assembly, based on FIGS. 12-13 D1 = 30 mm

2. Pre-Clinical In Vivo Study

Rigid Device Preparation for Pre-Clinical In Vivo Study

Figures 14A, 14B, 14C, 14D, 14E, 14F, 14G:
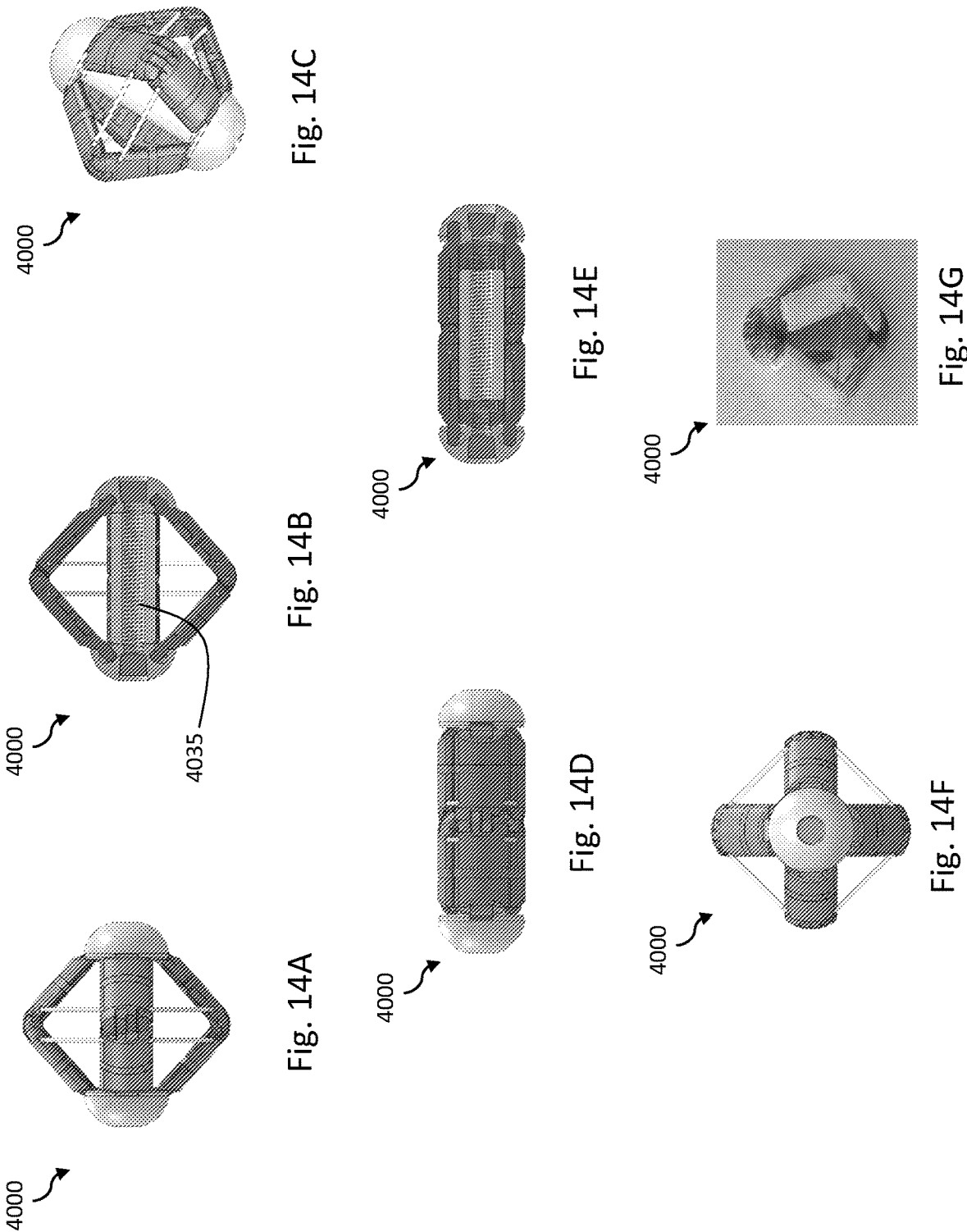
FIGS. 14A-14G illustrate an example of a device of trapping a predetermined cooperating object while allowing chyme flow of which capability may be determined in vivo on a pig.

With reference to FIGS. 14A-14G, in order to test performance of the device in vivo, a rigid device 4000 based on the principles of devices 1000, 2000 and 3000, adapted for administration to pig was prepared. FIGS. 14A-14C and FIGS. 14D-14E show schematically the device 4000 for temporary ICV retention in a pig, respectively in a trapping (open) configuration (FIGS. 14A-14C) and in a closed (swallowing) configuration (FIGS. 14D-14E). FIGS. 10A, 9D, and 10F show a front view of the device 3000. FIG. 14F shows a top view of the device 4000 and FIG. 14F shows a photograph of the prepared device.

Device preparation and assembly was done as follows: device arms and head were made by stratasys 3D printer rigid VERO material. Each of the arms was labeled with a barium thread to enable identification in X-ray imaging. Each two arms were hinged together with a nylon pin. A stainless steel biasing spring 4035 of 1.9 mm diameter was pulled through one of the heads. The first end was locked by a stainless steel locking element. The second end was pulled through a support silicone 55 A shore tube of 4 mm external diameter and 2 mm internal diameter and then through the second head, and locked by a second locking element. Arms were then hinged to the heads via a designated arm-head locking structure (as described in reference to device 1000). A circumferential thread was pulled through designated holes in the arms and tied at the end. Device dimensions in the folded configuration were about 29 mm in length and 10.2 mm in diameter, while in the unfolded configuration the diameter was of about 24.5 mm.

The assembled device was then subjected to an in vitro retention test, as described in reference to FIGS. 12-13 (D1=30 mm, D2=16 mm). Test results were acceptable. 100% of the 12 mm glass beads were blocked, 0% of the 6 mm glass beads were retained, the emptying force was >5N (D2=16 mm). Results are summarized in table 6 discussed earlier. #

Dosing System Preparation for Pre-Clinical In Vivo Study

Figures 15A, 15B:
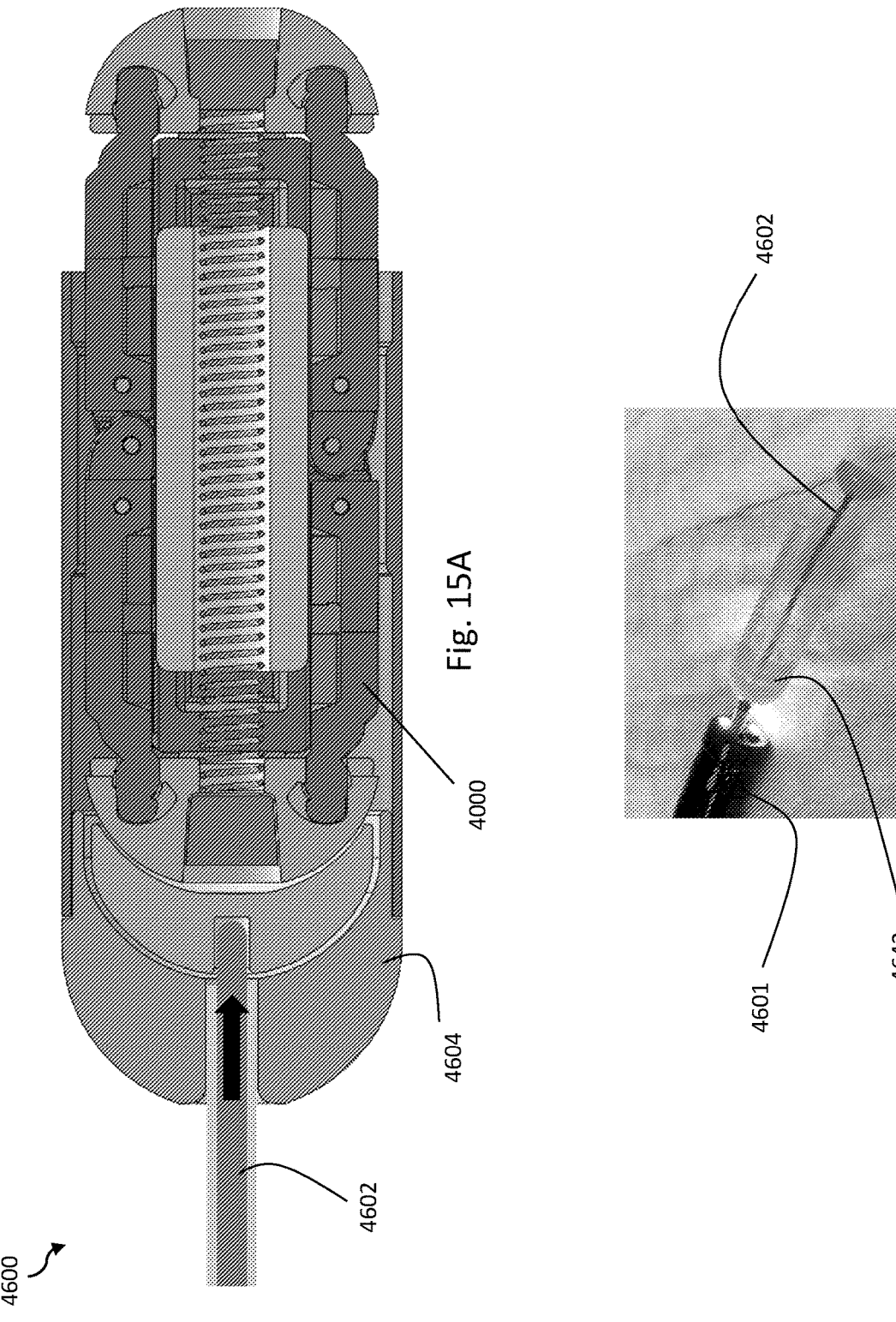
FIGS. 15A-15B illustrate a dosing system prepared for an in vivo study on a pig.

With reference to FIGS. 15A-15B, in order to dose the device into a pig's GI tract via a gastroscope 4601, a dosing system 4600 was prepared. FIG. 15A shows schematically the dosing system, and FIG. 15B shows a photograph of the dosing system. A housing adaptor 4604 was made by a Stratasys 3D printer. The dosing adaptor was designed to house the device in the folded configuration in one end, and to be connected to an ejection lead 4602 (US endoscopy 00711144) on the other hand. The assembly of the dosing system was made as follows: the ejection lead 4602 was first pulled through the gastroscope 4601, the housing adaptor 4604 was then connected to the ejection lead 4602 and then, the device 4000 was placed in the housing adaptor 4604 so to enable ejection of the desired site in the animal GI.

Platforms Tested

The study was aimed to evaluate the performance of the tapering system in an animal model. The tested performance features included administration, unfolding of the device in small intestine, transit through GI, retention of the device in ICV, retention of the tablet on the device and safety. Deliberately, no emptying timer mechanism was tested (instead of timers in the device 4000, support members of non-dissolving rigid material were fixed).

The trapping device 4000 as well as the control tablet were labeled with barium to enable detection by X-ray and CT scan imaging to assess transit along the GI. Control tablet was not erodible and had a conventional size tablet was made of 20% barium and 79% of ethyl cellulose and 1% magnesium stearate. Tablet was compressed in conventional tableting machine and then coated with 6% cellulose acetate solution in acetone. The coat was left to dry. Tablet remained intact when placed in water for 48 hr. Features are provided in table 7 below:

TABLE 7

| features of the tested platform | |
|---|---|
| feature | platforms tested |
| Trapper # | 4000 |
| trapping config diameter (mm) | 24.5 |
| biasing member | stainless steel spring |
| meshwork (mm²) | 45 mm² (per opening) × 8 |
| length/diameter (mm) | 29/10.2 |
| timer pin materials | stainless steel |
| emptying test force (gr) (D 2 = 16 mm) | >500 |
| control tablet | non erodible, labeled with barium |
| tablet length/diameter (mm) | 24.5/9 |

Animals: 2 domestic pigs, weighing 40-45 kg were acclimated for 7 days before dosing. The animals were weighed and food consumption was assessed.

Study procedure: (dosing and monitoring) were performed as described below 12 hr prior to dosing, animals were fasted. On day 1 (t=0) animals were anesthetized and dosing was conducted. Dosing was conducted with the aid of a dosing system described in disclosure and a gastroscope.

Figure 16:
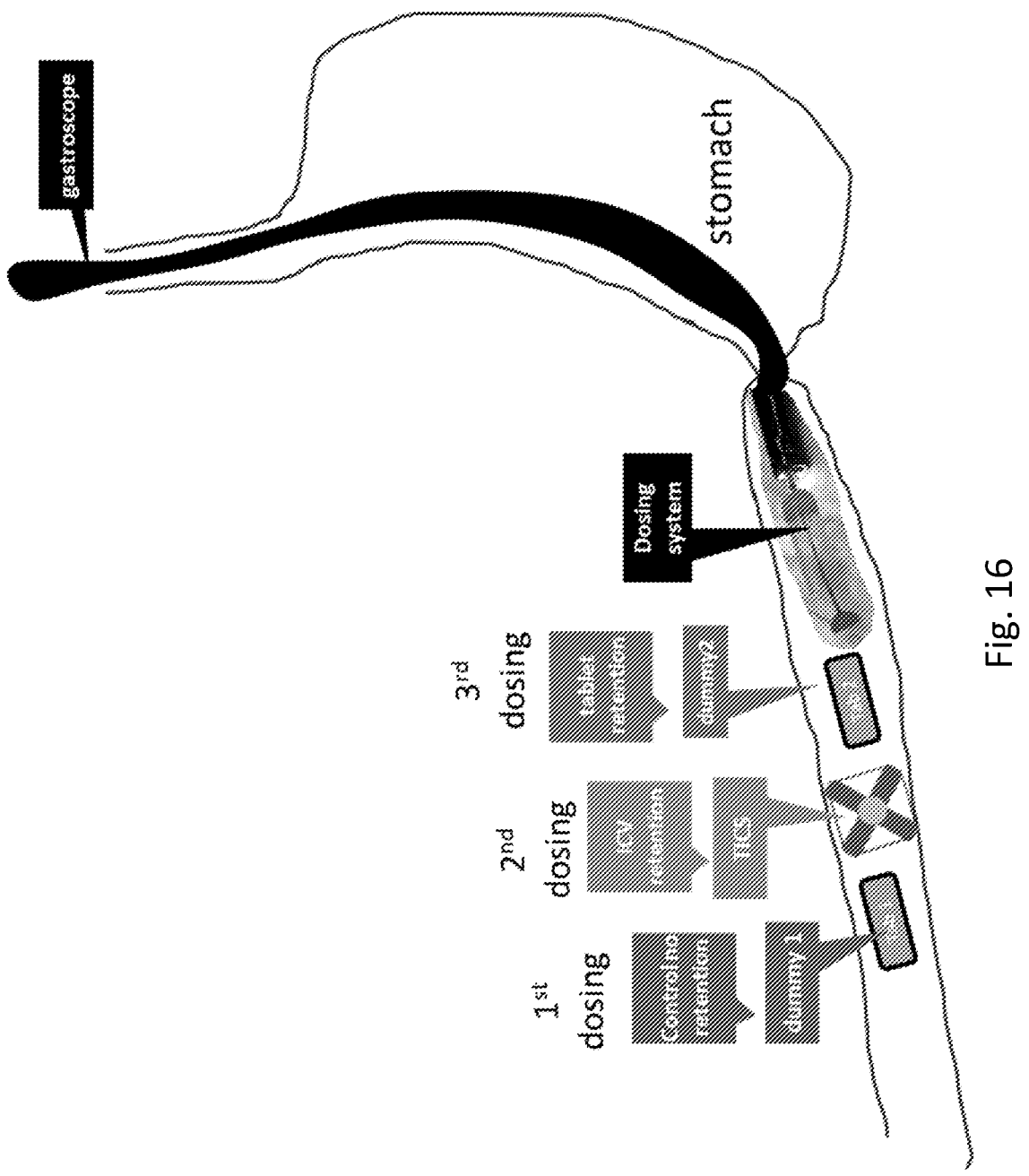

With reference to FIG. 16, a control tablet 1, then a prototype 1, then a control tablet 2 were dosed into the duodenum. Following dosing, and once every day after (day 1-11), X-ray was conducted to locate objects dosed. In day 4 and 5 in addition to X-ray, a CT imaging was conducted. Following dosing and every day after animals were given a daily conventional meal while water was ad libitum. Study protocol is summarized in table 8.

TABLE 8

| in vivo study protocol | | |
|---|---|---|
| day | test | food and water |
| 1 | dummy tab 1 > prototype A > dummy tab 2 dosing to duodenum, X-ray imaging | fast 12 hr before dosing regular meal every day, water ad libitum |
| 2-10 | X-ray imaging | conventional meal every day, water ad libitum |
| 4, 5 | X-ray imaging + CT | conventional meal every day, water ad libitum |
| 11 | X-ray imaging + euthanasia + autopsy | |

Objects Localization in GI During Study

To enable optimal detection of objects location in animal, the following was done:

1. PIG GI anatomy based on literature data
2. X-ray was conducted once every day, three coins were placed on pig belly in same position and distance while imaging was done in anterior-posterior and lateral imaging orientations.
3. Feces was collected and screened to detected emptied objects.
4. 3D full belly CT was conducted at day 4 and 5.
5. On autopsy the following was done:
   a. Verification of GI organs position was done (stomach, small intestine, ICV, cecum, colon).
   b. Verification of ICV location in X-ray-prototype A trapper was placed in the ICV, a cut made in ileum, 30 cm from ICV and prototype A was forwarded gently to ICV, and an X-ray image was done.

Study Success Criteria

Trapper transit to ICV within no more than 48 hr more than 1st control tablet;

Trapper retention at the ICV for least 24 hr more than control tablet 1 (which was dosed before the trapper);

2nd control tablet (dosed after the trapper) retention at the ICV for least 24 hr more than control tablet 1 (which was dosed before the trapper);

Safety

No significant adverse events are observed by veterinarian

Acceptable health status, food consumption, weight gain and feces (indication of food transit with no significant obstruction by trapper in ICV Acceptable gross pathology of GI (especially stomach, ileum, ICV) on autopsy (day 11), with no macro hemorrhage or segment deformation and no backflow from colon into ileum (indication of ICV malfunctioning)

Deliberately, emptying timer mechanism was not tested (instead of a timer element in the device, biasing member was fixed by non-dissolving rigid element).

Figure 17:
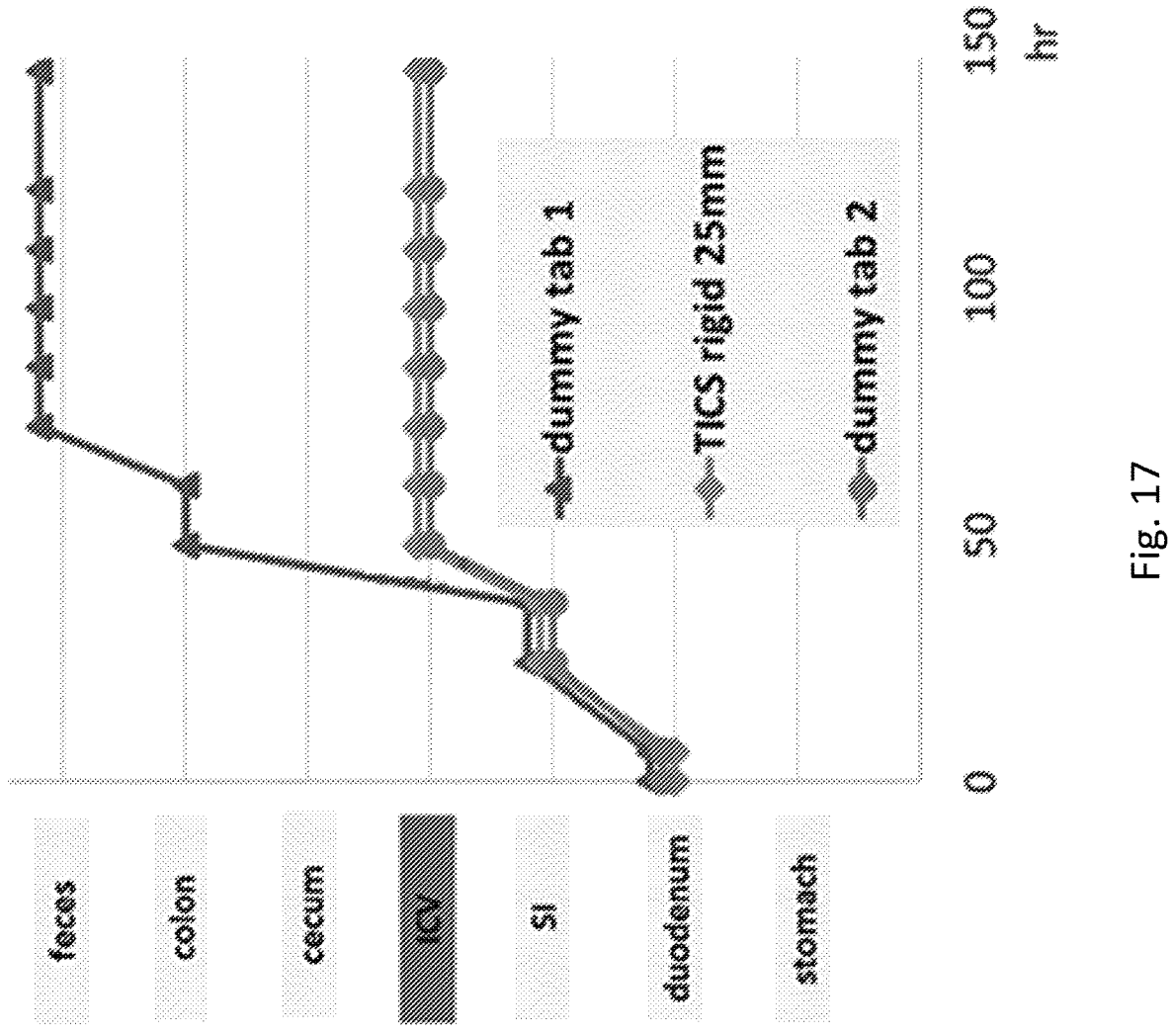

Study Results (See FIGS. 17-18):

Safety:

Safety Results Met Study Criteria

General health: animal health, food consumption, weight gain, feces were acceptable Gross pathology: No abnormalities were found in the abdomen cavity and the GI tract including stomach, small intestine, ICV, colon.

trapper transit, trapper retention, tablet retention results

Transit time to ICV, retention time in ICV and total GI transit were estimated based on the imaging described. Results are given in table 9 below. A graph demonstrating the results for pig 1 including representative X-ray and CT imaging from 94 hr are given in FIGS. 17-18.

The results obtained met study criteria: Trapper transit was less than 72 hr (36 and 24 hr in pig 1 and 2 respectively), Trapper retention in ICV was more than 24 hr, Tablet 2 was retained in ICV>24 hr more that tablet 1.

3. Type A and Type B Pin Emptying Test

Rigid devices according to specific implementations of device 1000 were prepared while the biasing member was made of straight silicone tube 55 A shore, 3/1 diameter (without the curved locking corners 1325, 1345 described with reference to FIG. 8E). Timer type A or type B were made according to the specific implementations provided with reference to device 1000.

A total of four trapper were prepared: two trappers with type A timer and two trappers with type B timer. An emptying test was applied as described in reference to FIGS. 12-13, while the medium used are as described in table 9 below. The results are given in table 9: Trapper with type A timer was retained unfolded at least 8 hr while found disassembled at 24 hr. Trapper with type B timer retained unfolded at least 24. At 24 hr, pH switched to 3.1 to activate the timer erosion and trapper disassembled within <4 hr.

TABLE 9

| type A and type B timer PIN emptying test | | | | |
|---|---|---|---|---|
| hr | medium | pH | HPMC AS TIMER (type A) | EUD EPO TIMER (Type B) |
| 0-1 | HCL 0.1M | 1 | retained unfolded | Retained unfolded |
| 1-3 | buffer phosphate, 0.015M | 6.8 | retained unfolded | retained unfolded |
| 3-24 | buffer phosphate, 0.02M | 7 | retained unfolded at least 8 hr | hold |
| 24-48 hr | buffer phosphate pH 7, 0.02M + 0.035M citric acid* | 3.1* | found disassembled at 24 hr | dis at 28 hr |

*pH obtained equal to that obtained with 2 acid tablets

The invention claimed is:

1. A device configured to be temporarily retained at an ileocecal valve of a subject in a trapping configuration, the device comprising:
   a trapping assembly configured to block a cooperating ingestible object while allowing chyme flow when the device is temporarily retained at the ileocecal valve,
   wherein the device is configured to transition from the trapping configuration into an emptying configuration in which the device is configured to pass through the ileocecal valve.

2. The device of claim 1, wherein the device is further configured to be reversibly deformable from a closed configuration into the trapping configuration.

3. The device of claim 2, wherein the dimensions of the device in the closed configuration are such that the device can fit in a cylinder of length of about 35 mm or less and/or of diameter of about 12 mm or less.

4. The device of claim 2, further comprising an opening assembly configured to deform the device from the closed configuration into the trapping configuration.

5. The device of claim 4, wherein the opening assembly comprises a biasing assembly configured to bias the device in the trapping configuration to resiliently return from the closed configuration into the trapping configuration.

6. The device of claim 5, wherein:

the trapping assembly comprises at least three flexible arms, each arm having a first end and a second end, and the biasing assembly comprises:

a first and second coupling heads, wherein the first end of each flexible arm is coupled to the first coupling head and the second end of each flexible arm is coupled to the second coupling head; and a resiliently deformable member configured to force the first and second coupling heads together to bend the arms thereby biasing the device in the trapping configuration.

7. The device of claim 6, wherein the trapping assembly further comprises one or more circumferential belts circling around the at least three flexible arms, and/or one or more circumferential threads circumferentially linking the at least three flexible arms.

8. The device of claim 6, further comprising a container to temporarily at least partially enclose the device in the closed configuration, wherein the container is resistant to standard gastric environmental conditions and configured to degrade in small intestine environmental conditions, the container being at least partially coated with or made of an enteric polymer.

9. The device of claim 6, wherein the first end of each flexible arm is coupled to the first coupling head releasably, and the second end of each flexible arm is coupled to the second coupling head releasably.

10. The device of claim 9, wherein, in the trapping configuration, said first and second ends are each inserted in a respective cavity of the first and second coupling heads, the resiliently deformable member maintaining said first and second end each secured inside the respective cavity.

11. The device of claim 6, further comprising a support tube, wherein the resiliently deformable member is arranged inside the support tube.

12. The device of claim 11, wherein the device carries a load of an active pharmaceutical ingredient inside or on the support tube.

13. The device of claim 12, wherein the support tube has one or more peripheral grooves each lodging a ring-shaped form containing the active pharmaceutical ingredient.

14. The device according to claim 12, wherein the device comprises an inner space in the closed configuration, the inner space containing at least part of the load of the active pharmaceutical ingredient.

15. The device of claim 6, wherein at least one flexible arm is made of an elastic material, and the resiliently deformable member is configured to bend the arms in a rounded shape.

16. The device of claim 6, wherein the arms are at least partially made of a material that gradually erodes in the intestine, so as to facilitate emptying.

17. The device of claim 2, further comprising a locking element configured to temporary maintain the device in the closed configuration for facilitating administration.

18. An oral dosage form for administering an emptying agent to a subject, the oral dosage form being used capable of use with the device of claim 1, when the device is positioned at the ileocecal valve of the subject in the trapping configuration, wherein the oral dosage form comprises:

an effective amount of the emptying agent sufficient to cause the ileocecal valve environment to reach at least one activation environmental condition thereby causing the device to transfer into the emptying configuration;

a coating inhibiting release of the emptying agent in the gastric environment and enabling release of the emptying agent in the ileocecal valve; and external dimensions enabling the oral dosage form to be blocked by said device when reaching the ileocecal valve.

19. A method of treating a condition by dispensing of an active pharmaceutical ingredient at the ileocecal valve of a subject suffering from said condition, the method comprising:

administering, to the subject, the device of claim 1; and subsequently administering the active pharmaceutical ingredient to the subject.

20. The method of claim 19, wherein the condition is an inflammatory bowel disease (IBD), ulcerative colitis (US), or Crohn's disease.

* * * * *